United States Patent
Garcia Rubio et al.

(10) Patent No.: US 11,299,472 B2
(45) Date of Patent: Apr. 12, 2022

(54) FUMARATE SALT OF (R)-3-(1-(2,3-DICHLORO-4-(PYRAZIN-2-YL)PHENYL)-2,2,2-TRIFLUOROETHYL)-1-METHYL-1-(1-METHYLPIPERIDIN-4-YL) UREA, METHODS OF PREPARATION, AND USES THEREOF

(71) Applicant: Helsinn Healthcare SA, Pazzallo-Lugano (CH)

(72) Inventors: Silvina Garcia Rubio, Princeton, NJ (US); Mauro Perseghini, Biasca (CH); Angelo Guainazzi, New York, NY (US); Claudio Pietra, Como (IT); Claudio Giuliano, Como (IT)

(73) Assignee: HELSINN HEALTHCARE SA, Pazzallo-Lugano (CH)

( * ) Notice: Subject to any disclaimer, the term of this patent is extended or adjusted under 35 U.S.C. 154(b) by 0 days.

(21) Appl. No.: 16/767,842

(22) PCT Filed: Dec. 7, 2018

(86) PCT No.: PCT/US2018/064512
§ 371 (c)(1),
(2) Date: May 28, 2020

(87) PCT Pub. No.: WO2019/118298
PCT Pub. Date: Jun. 20, 2019

(65) Prior Publication Data
US 2020/0299260 A1    Sep. 24, 2020

Related U.S. Application Data

(60) Provisional application No. 62/597,236, filed on Dec. 11, 2017.

(51) Int. Cl.
*C07D 401/12*  (2006.01)
*A61P 5/06*  (2006.01)

(52) U.S. Cl.
CPC .......... *C07D 401/12* (2013.01); *A61P 5/06* (2018.01); *C07B 2200/13* (2013.01)

(58) Field of Classification Search
CPC ...... C07D 401/12; A61P 5/06; C07B 2200/13
See application file for complete search history.

(56) References Cited

U.S. PATENT DOCUMENTS

| 9,546,157 B2 | 1/2017 | Giuliano et al. |
| 9,926,337 B2 | 3/2018 | Giuliano et al. |
| 10,577,384 B2 | 3/2020 | Giuliano et al. |
| 2005/0288316 A1 | 12/2005 | Crossley et al. |
| 2015/0252021 A1* | 9/2015 | Giuliano ............ A61P 3/06 514/232.2 |

FOREIGN PATENT DOCUMENTS

| WO | 2005048916 A3 | 6/2005 |
| WO | 2011060397 A1 | 5/2011 |
| WO | 2012113103 A1 | 8/2012 |
| WO | 2015134839 A1 | 9/2015 |

OTHER PUBLICATIONS

Berge et al., 66(1) Pharmaceutical Salts, p. 1-19 (1977) (Year: 1977).*
International Search Report and Written Opinion of PCT/US2018/064512 dated Jan. 25, 2019 (9 pages).

* cited by examiner

*Primary Examiner* — Timothy R Rozof
(74) *Attorney, Agent, or Firm* — McNeill Baur PLLC

(57) ABSTRACT

Provided are various embodiments relating to fumarate salt of (R)-3-(1-(2,3-dichloro-4-(pyrazin-2-yl)phenyl)-2,2,2-trifluoroethyl)-1-methyl-1-(1-methylpiperidin-4-yl) urea, and methods of producing and using the same to treat conditions and disorders associated with an increase of ghrelin level, such as food abuse, alcohol addiction, and other disorders (e.g., Prader-Willi syndrome). Also provided are various embodiments relating to crystalline HM04 free base, different crystalline forms of HM04 fumarate salt, and methods of producing the same.

22 Claims, 37 Drawing Sheets

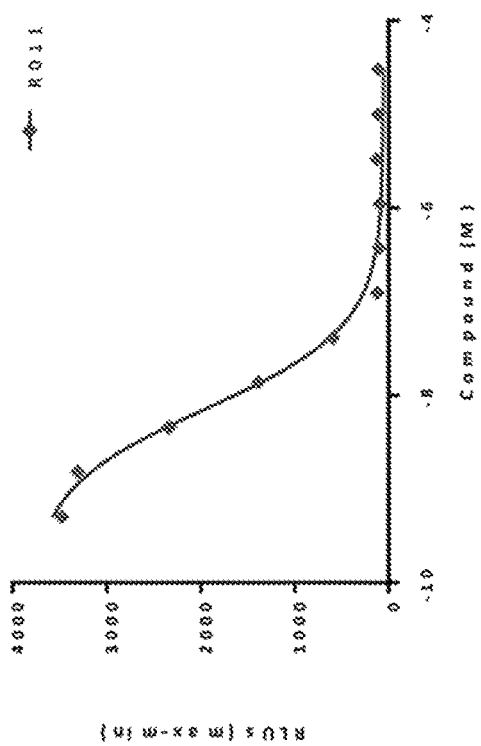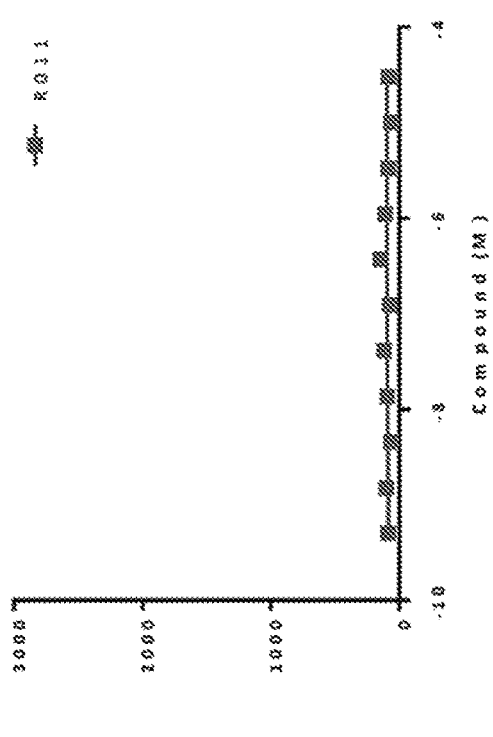
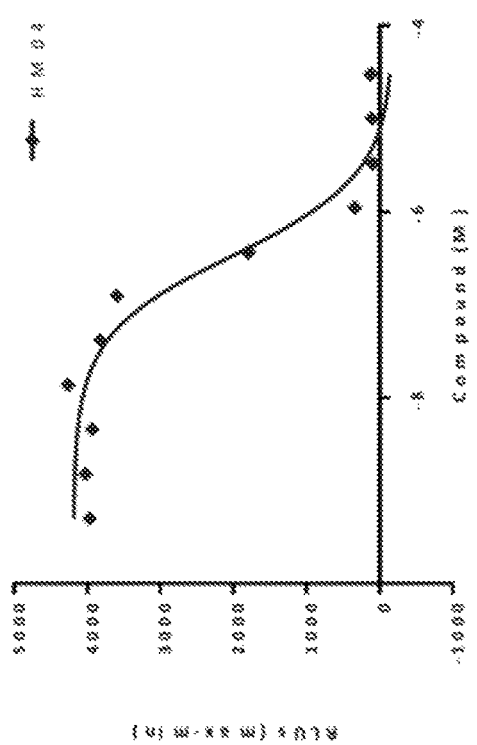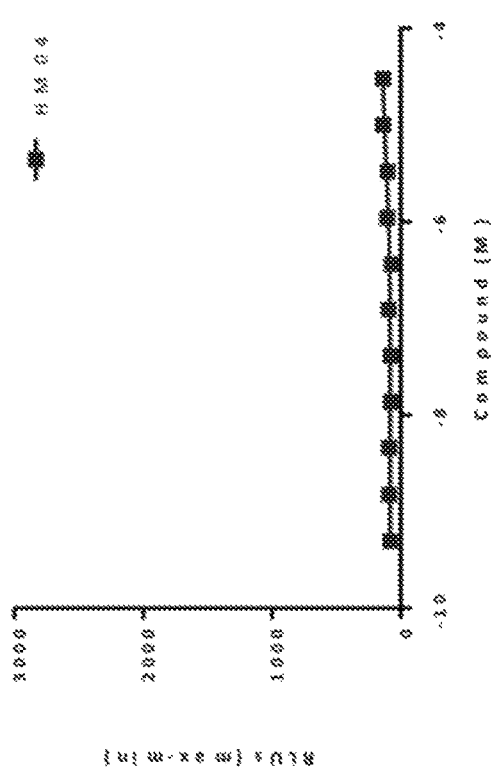
Figure 21A　　Figure 21B　　Figure 21C　　Figure 21D

FUMARATE SALT OF (R)-3-(1-(2,3-DICHLORO-4-(PYRAZIN-2-YL)PHENYL)-2,2,2-TRIFLUOROETHYL)-1-METHYL-1-(1-METHYLPIPERIDIN-4-YL) UREA, METHODS OF PREPARATION, AND USES THEREOF

This application is a national phase entry pursuant to 35 U.S.C. § 371 of International Application No. PCT/US2018/064512, filed Dec. 7, 2018, which claims the benefit of U.S. Provisional Application No. 62/597,236, filed Dec. 11, 2017, which is incorporated by reference herein in its entirety for any purpose.

FIELD

The present disclosure relates to fumarate salt of (R)-3-(1-(2,3-dichloro-4-(pyrazin-2-yl)phenyl)-2,2,2-trifluoroethyl)-1-methyl-1-(1- methylpiperidin-4-yl) urea (also referred to as HM04 or H0900), a potent ghrelin/growth hormone secretagogue receptor (GHS-R1a) antagonist useful in the treatment of diseases associated with an imbalance of ghrelin levels, such as binge eating, alcohol addiction, and other disorders (e.g., Prader-Willi syndrome). The present disclosure also relates to crystalline HM04 free base, different crystalline forms of HM04 fumarate salt, and methods of producing the same.

BACKGROUND

Ghrelin, a growth hormone-releasing peptide produced by ghrelinergic cells in the gastrointestinal tract, is understood to function as a neuropeptide that regulates energy metabolism by stimulating appetite. The modulation, for example inhibition, of ghrelin signaling, through the ghrelin/growth hormone secretagogue receptor (GHS-R1a), is an attractive target for pharmacological treatment of disorders associated with high ghrelin level. Potential disorders for treatment using ghrelin modulators include food abuse (such as binge eating, obesity, hyperphagia (or uncontrollable appetite), post-dieting body weight rebound (including post-dieting hyperphagia), alcohol addiction, and genetic diseases associated with increased ghrelin level (e.g., Prader-Willi syndrome (PWS)).

PWS occurs in approximately 1 in 10,000 births and is associated with deletion or lack of expression of region 15q11.2 of the paternal chromosome 15. Characteristics of PWS include short stature, low muscle tone, and hyperphagia. Growth hormone replacement is frequently used to treat growth deficiencies and hypotonia. However, treatment for the insatiable appetite is lacking and PWS children can mature into adults suffering from obesity and type 2 diabetes. Levels of ghrelin are generally elevated in PWS; however, the relationship with ghrelin signaling and food intake in PWS remains unclear. See Purtell L., et al., In adults with Prader-Willi syndrome, elevated ghrelin levels are more consistent with hyperphagia than high PYY and GLP-1 levels. *Neuropeptides*. 2011; 45(4):301-7; Cummings D. E., et al., Elevated plasma ghrelin levels in Prader Willi syndrome. *Nature Medicine*. 2002; 8(7):643-4; DelParigi A., et al., High circulating ghrelin: a potential cause for hyperphagia and obesity in Prader-Willi syndrome. *The Journal of Clinical Endocrinology and Metabolism*. 2002; 87(12): 5461-4.

Accordingly, it is desirable to find treatments that effectively inhibit GHSR1a, that are tolerable to the patient, and that do not interfere with other functions of the growth hormones. GHSR1a modulators, including inhibitors such as (R)-3-(1-(2,3-dichloro-4-(pyrazin-2-yl)phenyl)-2,2,2-trifluoroethyl)-1-methyl- 1-(1-methylpiperidin-4-yl)urea (HM04, H0900) depicted below, are reported in U.S. Pat. No. 9,546,157.

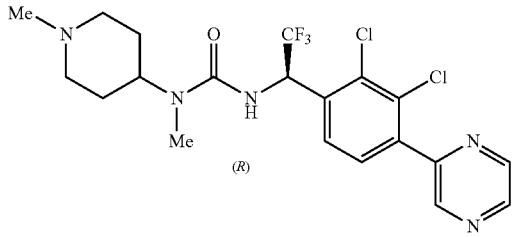 [SMILES: CN1CCC(N(C)C(=O)N[C@H](c2ccc(-c3cnccn3)c(Cl)c2Cl)C(F)(F)F)CC1 ; "(R)"]

However, stable salt forms, and crystalline forms thereof are not disclosed therein.

SUMMARY

Embodiment 1. A (R)-3-(1-(2,3-dichloro-4-(pyrazin-2-yl)phenyl)-2,2,2-trifluoroethyl)-1-methyl-1-(1-methylpiperidin-4-yl)urea fumarate salt.

Embodiment 2. The salt of embodiment 1, wherein the salt is 1:1 (R)-3-(1-(2,3-dichloro-4-(pyrazin-2-yl)phenyl)-2,2,2-trifluoroethyl)-1-methyl-1-(1-methylpiperidin-4-yl) urea:fumarate salt.

Embodiment 3. The salt of any one of the preceding embodiments, wherein the salt is at least 50% in crystalline form.

Embodiment 4. The salt of any one of the preceding embodiments, wherein the salt is at least 60%, at least 70%, at least 80%, at least 90%, at least 95%, at least 96%, at least 97%, at least 98%, at least 99%, or 100% in crystalline form.

Embodiment 5. The salt of any one of the preceding embodiments comprising at least one crystalline form chosen from Form 1, Form 2, Form 3, and Form 4.

Embodiment 6. The salt of any one of the preceding embodiments comprising Form 1 having an XRPD pattern substantially similar to the XRPD pattern of FIG. 12 as determined by XRPD using Cu K alpha radiation.

Embodiment 7. The salt of any one of embodiments 1 to 5 comprising Form 2 characterized by an XRPD pattern substantially similar to the XRPD pattern of FIG. 3 as determined by XRPD using Cu K alpha radiation.

Embodiment 8. The salt of any one of embodiments 1 to 5 comprising Form 3 characterized by an XRPD pattern substantially similar to the XRPD pattern of FIG. 15 as determined by XRPD using Cu K alpha radiation.

Embodiment 9. The salt of any one of embodiments 1 to 5 comprising Form 4 characterized by an XRPD pattern substantially similar to the XRPD pattern of FIG. 16 as determined by XRPD using Cu K alpha radiation.

Embodiment 10. The salt of any one of embodiments 1 to 5 comprising Form 1 characterized by an XRPD pattern, using Cu K alpha radiation, comprising peaks at 7.8±0.2, 9.5±0.2, 14.3±0.2, 16.7±0.2, 17.2±0.2, 18.5±0.2, 18.8±0.2, 19.3±0.2, 20.0±0.2, 20.7±0.2, 22.4±0.2, 23.2±0.2, 25.6±0.2, 27.2±0.2, 31.7±0.2, and 32.4±0.2 degrees 2 theta.

Embodiment 11. The salt of any one of embodiments 1 to 5 comprising Form 3 characterized by an XRPD pattern, using Cu K alpha radiation, comprising peaks at 7.2±0.2, 9.4±0.2, 9.7±0.2, 10.8±0.2, 14.3±0.2, 15.1±0.2, 16.2±0.2, 17.9±0.2, 18.7±0.2, 18.9±0.2, 19.6±0.2, 21.5±0.2, 22.7±0.2, 23.7±0.2, 24.3±0.2, 25.1±0.2, 27.4±0.2, 28.7±0.2, and 34.9±0.2 degrees 2 theta.

Embodiment 12. The salt of any one of embodiments 1 to 5 comprising Form 4 characterized by an XRPD pattern, using Cu K alpha radiation, comprising peaks at 12.2±0.2, 13.2±0.2, 15.0±0.2, 15.4±0.2, 17.6±0.2, 18.1±0.2, 19.5±0.2, 20.2±0.2, 20.9±0.2, 21.4±0.2, 23.0±0.2, 23.4±0.2, 24.4±0.2, 24.8±0.2, 25.9±0.2, 27.9±0.2, 28.9±0.2, 29.6±0.2, 30.7±0.2 degrees 2 theta.

Embodiment 13. Crystalline (R)-3-(1-(2,3-dichloro-4-(pyrazin-2-yl)phenyl)-2,2,2-trifluoroethyl)-1-methyl-1-(1-methylpiperidin-4-yl)urea having an XRPD pattern substantially similar to the XRPD pattern of FIG. 1A as determined by XRPD using Cu K alpha radiation.

Embodiment 14. A drug product comprising the salt of any one of embodiments 1 to 12 or the crystalline compound of embodiment 13.

Embodiment 15. A composition comprising the salt of any one of embodiments 1 to 12 or the crystalline compound of embodiment 13 and a pharmaceutically acceptable carrier.

Embodiment 16. A method of preparing the salt of any one of embodiments 1 to 12 comprising combining (R)-3-(1-(2,3-dichloro-4-(pyrazin-2-yl)phenyl)-2,2,2-trifluoroethyl)-1-methyl-1-(1-methylpiperidin-4-yl)urea with fumaric acid.

Embodiment 17. The method of embodiment 16, wherein the (R)-3-(1-(2,3-dichloro-4-(pyrazin-2-yl)phenyl)-2,2,2-trifluoroethyl)-1-methyl-1-(1-methylpiperidin-4-yl)urea is in solid form when combined with fumaric acid.

Embodiment 18. The method of embodiments 16, wherein the (R)-3-(1-(2,3-dichloro-4-(pyrazin-2-yl)phenyl)-2,2,2-trifluoroethyl)-1-methyl-1-(1-methylpiperidin-4-yl)urea is in solution when combined with fumaric acid.

Embodiment 19. The method of any one of embodiments 16 to 18, wherein the (R)-3-(1-(2,3-dichloro-4-(pyrazin-2-yl)phenyl)-2,2,2-trifluoroethyl)-1-methyl-1-(1-methylpiperidin-4-yl)urea is subjected to acid/base extraction prior to being combined with fumaric acid.

Embodiment 20. The method of any one of embodiments 16 to 18, wherein the (R)-3-(1-(2,3-dichloro-4-(pyrazin-2-yl)phenyl)-2,2,2-trifluoroethyl)-1-methyl-1-(1-methylpiperidin-4-yl)urea is not subjected to an acid/base extraction prior to being combined with fumaric acid.

Embodiment 21. A method of reducing ghrelin signaling activity in a cell comprising exposing the cell to a salt of any one of embodiments 1 to 12, the crystalline compound of embodiment 13, the drug product of embodiment 14, or the composition of embodiment 15.

Embodiment 22. The method of embodiment 21, wherein the cell is exposed to the salt, the crystalline compound, the drug product, or the composition in vitro.

Embodiment 23. The method of embodiment 21 or embodiment 22, wherein the ghrelin signaling activity is measured by level of intracellular calcium as detected by fluorescence imaging plate reader (FLIPR) assay.

Embodiment 24. The method of embodiment 23, wherein the level of intracellular calcium is reduced.

Embodiment 25. A method of reducing ghrelin signaling activity in a subject comprising administering to the subject any one of embodiments 1 to 12, the crystalline compound of embodiment 13, the drug product of embodiment 14, or the composition of embodiment 15.

Embodiment 26. A method of treating a subject having a condition or disorder associated with an increase in ghrelin level, comprising administering to the subject a therapeutically effective amount of the salt of any one of embodiments 1 to 12, the crystalline compound of embodiment 13, the drug product of embodiment 14, or the composition of embodiment 15.

Embodiment 27. The method of embodiment 26, wherein the condition or disorder is chosen from food abuse, alcohol addiction, and Prader-Willi syndrome.

Embodiment 28. The method of embodiment 26 or embodiments 27, wherein the condition or disorder is chosen from binge eating, obesity, post-dieting body weight rebound, and hyperphagia.

Embodiment 29. The method of any one of embodiments 25 to 28 comprising orally administering the salt, the crystalline compound, the drug product, or composition to the subject.

Embodiment 30. The method of any one of embodiments 25 to 29, wherein the subject's level of circulating growth hormone is modulated.

Embodiment 31. The method of any one of embodiments 25 to 30, wherein the subject's level of circulating growth hormone is reduced.

Embodiment 32. The method of any one of embodiments 25 to 31, wherein the subject's food intake is reduced.

Embodiment 33. The method of any one of embodiments 25 to 32, wherein the subject's body weight is reduced.

Embodiment 34. The method of any one of embodiments 25 to 32, wherein the subject's body weight is stabilized.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIG. 1B (top panel) shows a representative XRPD profile of HM04 free base crystalline Form 1 prepared as set forth in Example 1B.

FIG. 21A shows the concentration-response curve of HM04 in the antagonist fluorescence imaging plate reader (FLIPR) assay using HEK293 cells expressing human GHSR1a receptor.

FIG. 21B shows the concentration-response curve of R011 in the antagonist FLIPR assay using HEK293 cells expressing human GHSR1a receptor.

FIG. 21C shows the concentration-response curve of HM04 in the agonist FLIPR assay using HEK293 cells expressing human GHSR1a receptor.

FIG. 21D shows the concentration-response curve of R011 in the agonist FLIPR assay using HEK293 cells expressing human GHSR1a receptor.

DESCRIPTION OF THE EMBODIMENTS

As summarized above, and as set forth in detail below, the present disclosure relates to (R)-3-(1-(2,3-dichloro-4-(pyrazin-2-yl)phenyl)-2,2,2-trifluoroethyl)-1-methyl-1-(1-methylpiperidin-4-yl)urea fumarate salt, crystalline forms thereof, and a crystalline form of (R)-3-(1-(2,3-dichloro-4-(pyrazin-2-yl)phenyl)-2,2,2-trifluoroethyl)-1-methyl-1-(1-methylpiperidin-4-yl)urea free base. The present disclosure also relates to methods of making the fumarate salt and crystalline forms thereof, and methods of using same for inhibition of GHSR1a.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

One aspect of the present disclosure relates to (R)-3-(1-(2,3-dichloro-4-(pyrazin-2-yl)phenyl)-2,2,2-trifluoroethyl)-1-methyl-1-(1- methylpiperidin-4-yl)urea fumarate salt. In at least one embodiment of the present disclosure, the salt is 1:1 (R)-3-(1-(2,3-dichloro-4-(pyrazin-2-yl)phenyl)-2,2,2-trifluoroethyl)- 1-methyl-1-(1-methylpiperidin-4-yl)urea:fumarate salt.

The salt can be in a variety of forms such as an oil or a solid. The solid can be amorphous, crystalline, or a mixture of both. In at least one embodiment of the present disclosure, the salt is at least 50% in crystalline form. In further embodiments, the salt can be at least 60%, at least 70%, at least 80%, at least 90%, at least 95%, at least 96%, at least 97%, at least 98%, at least 99%, and 100% crystalline.

If the salt is at least partially crystalline, the crystalline form can be chosen from Form 1, Form 2, Form 3, and Form 4.

Figure 12:
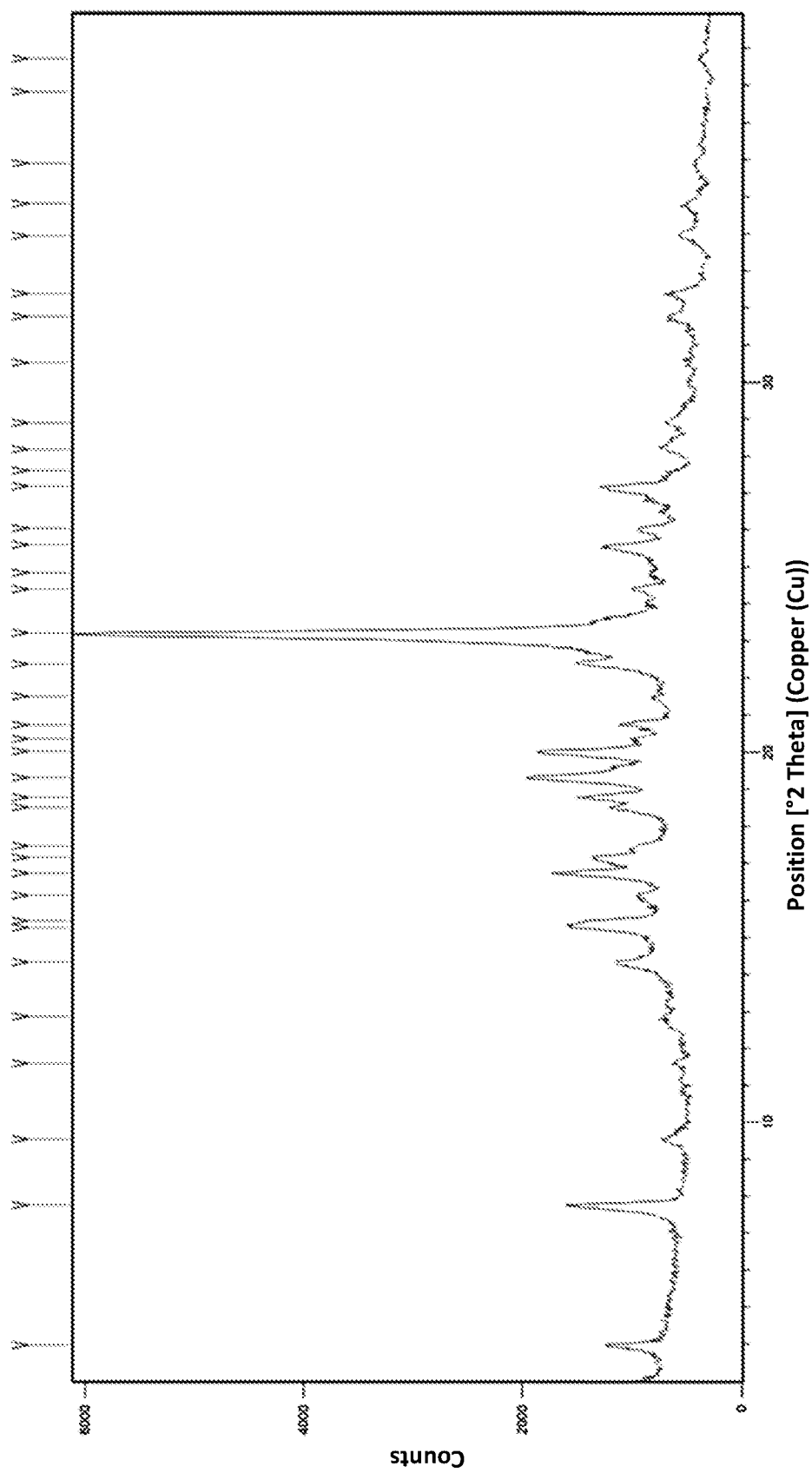
FIG. 12 provides a representative XRPD profile of HM04 fumarate salt crystalline Form 1 prepared as set forth in Example 6, Trial 2.

In at least one embodiment, the salt comprises crystalline Form 1 characterized by an XRPD pattern substantially similar to the XRPD pattern of FIG. 12 as determined XRPD using Cu K alpha radiation. In further embodiments, the salt can be at least 60%, at least 70%, at least 80%, at least 90%, at least 95%, at least 96%, at least 97%, at least 98%, at least 99%, and 100% crystalline Form 1.

In some embodiments, Form 1 can be characterized by an XRPD pattern, using Cu K alpha radiation, comprising peaks at 7.8±0.2, 9.5±0.2, 14.3±0.2, 16.7±0.2, 17.2±0.2, 18.5±0.2, 18.8±0.2, 19.3±0.2, 20.0±0.2, 20.7±0.2, 22.4±0.2, 23.2±0.2, 25.6±0.2, 27.2±0.2, 31.7±0.2, and 32.4±0.2 degrees 2 theta.

Figure 3:
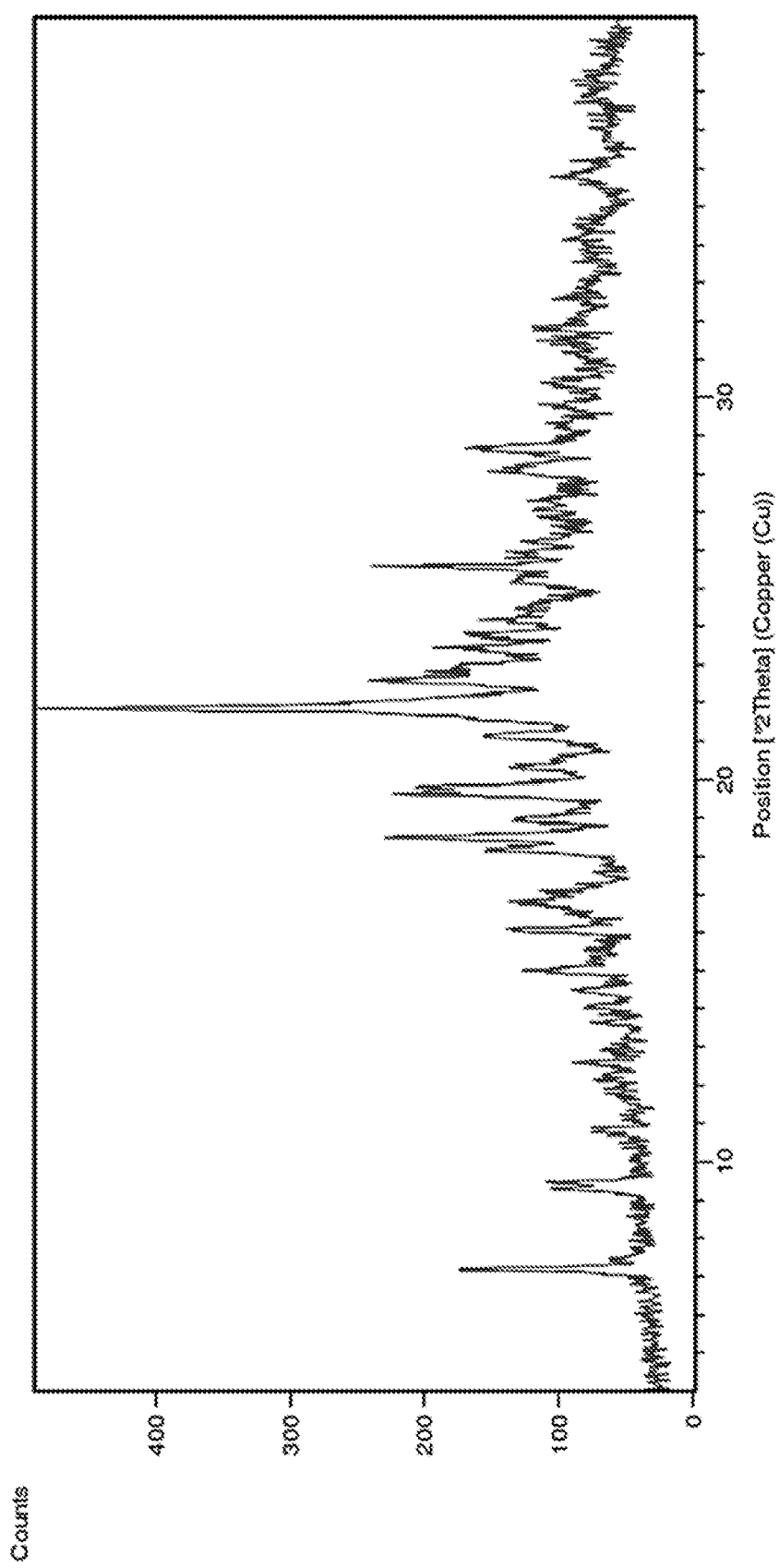
FIG. 3 shows a representative XRPD profile of HM04 fumarate salt crystalline Form 2 prepared as set forth in Example 3.

In at least one embodiment, the salt comprises crystalline Form 2 characterized by an XRPD pattern substantially similar to the XRPD pattern of FIG. 3 as determined by XRPD using Cu K alpha radiation. In further embodiments, the salt can be at least 60%, at least 70%, at least 80%, at least 90%, at least 95%, at least 96%, at least 97%, at least 98%, at least 99%, and 100% crystalline Form 2.

Figure 15:
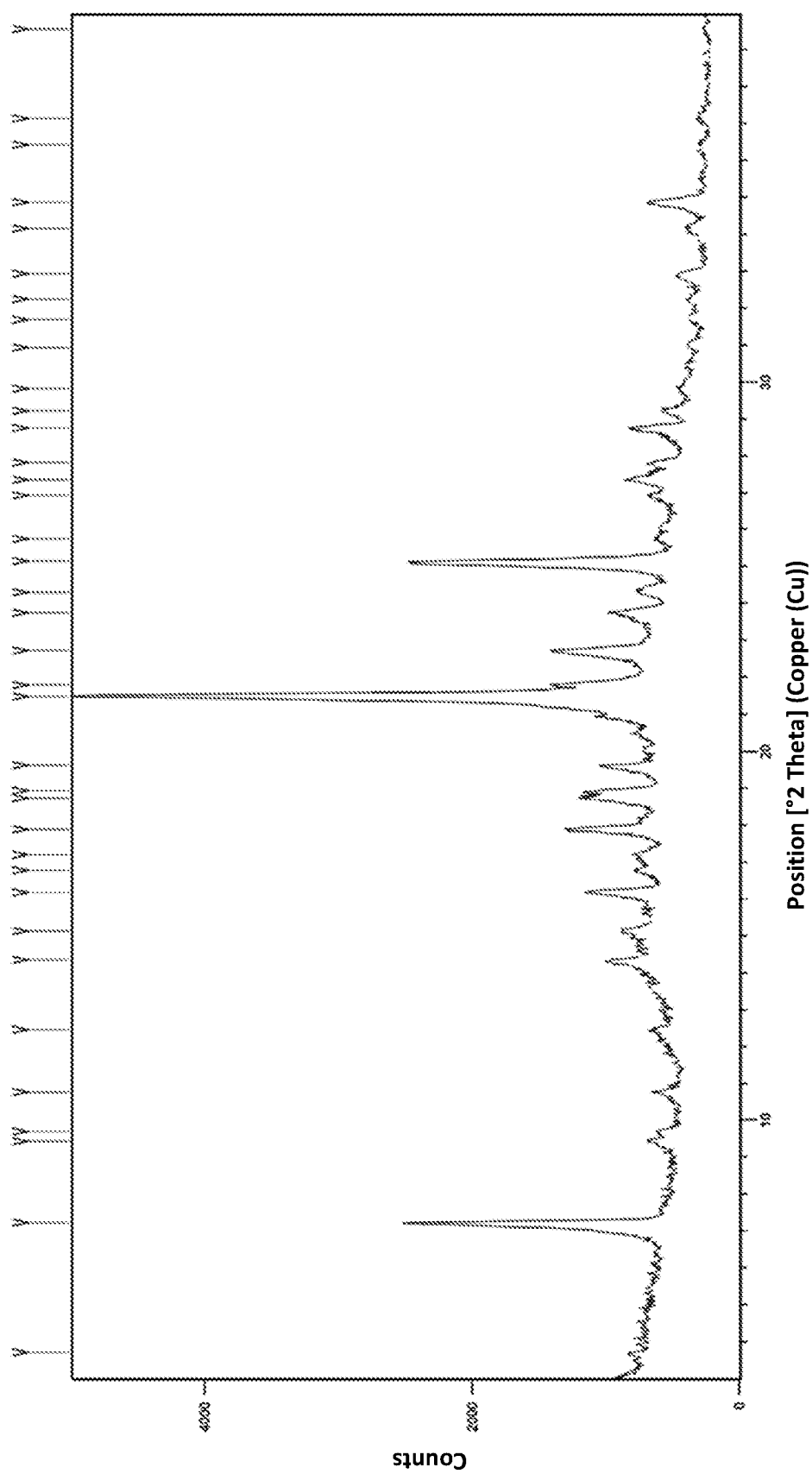
FIG. 15 provides a representative XRPD profile of HM04 fumarate salt crystalline Form 3 prepared as set forth in Example 7.

In at least one embodiment, the salt comprises crystalline Form 3 characterized by an XRPD pattern substantially similar to the XRPD pattern of FIG. 15 as determined by XRPD using Cu K alpha radiation. In further embodiments, the salt can be at least 60%, at least 70%, at least 80%, at least 90%, at least 95%, at least 96%, at least 97%, at least 98%, at least 99%, and 100% crystalline Form 3.

In some embodiments, Form 3 can be characterized by an XRPD pattern, using Cu K alpha radiation, comprising peaks at 7.2±0.2, 9.4±0.2, 9.7±0.2, 10.8±0.2, 14.3±0.2, 15.1±0.2, 16.2±0.2, 17.9±0.2, 18.7±0.2, 18.9±0.2, 19.6±0.2, 21.5±0.2, 22.7±0.2, 23.7±0.2, 24.3±0.2, 25.1±0.2, 27.4±0.2, 28.7±0.2, and 34.9±0.2 degrees 2 theta.

Figure 16:
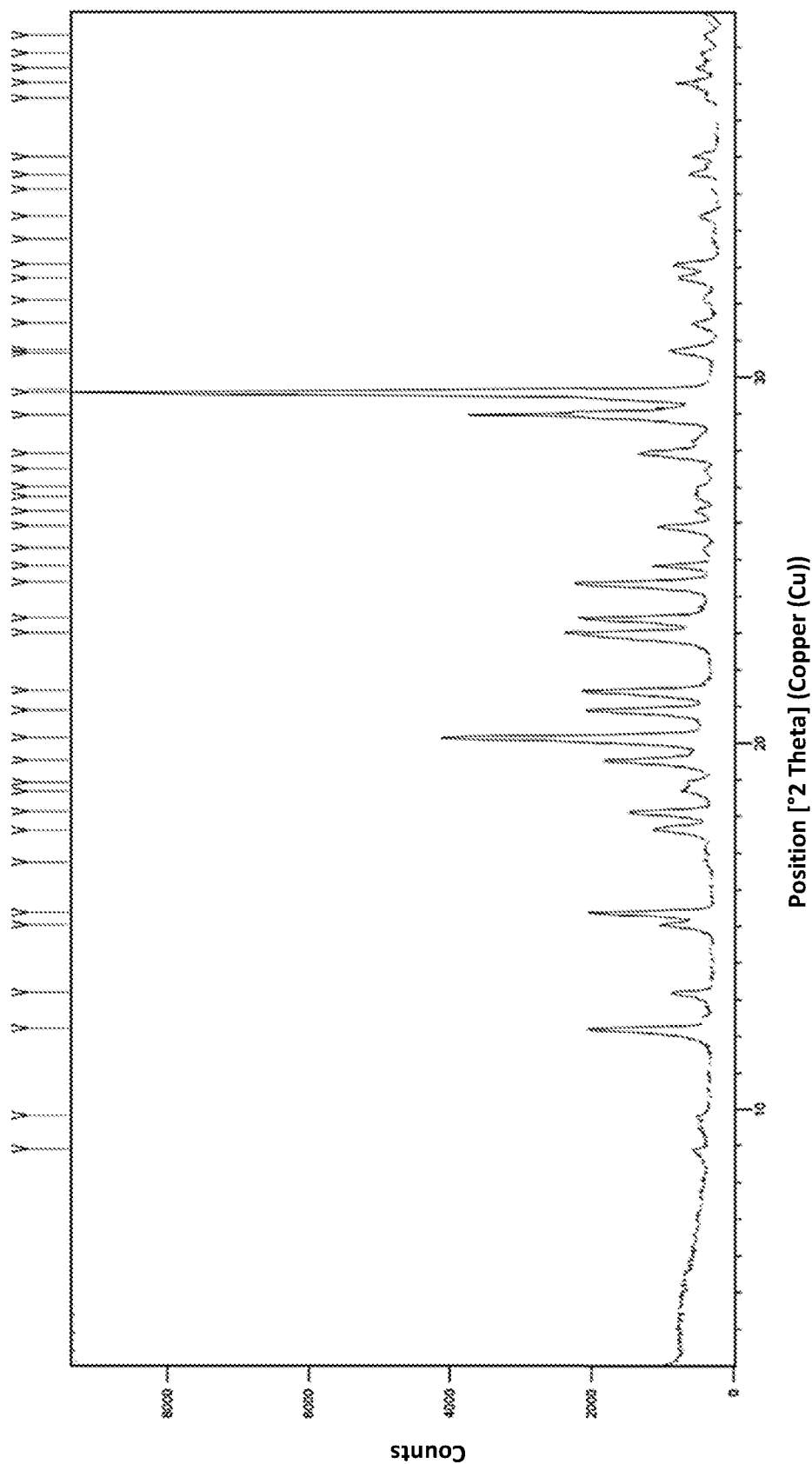
FIG. 16 provides a representative XRPD profile of HM04 fumarate sale crystalline Form 4 prepared as set forth in Example 8.

In at least one embodiment, the salt comprises crystalline Form 4 characterized by an XRPD pattern substantially similar to the XRPD pattern of FIG. 16 as determined by XRPD using Cu K alpha radiation. In further embodiments, the salt can be at least 60%, at least 70%, at least 80%, at least 90%, at least 95%, at least 96%, at least 97%, at least 98%, at least 99%, and 100% crystalline Form 4.

In some embodiments, Form 4 can be characterized by an XRPD pattern, using Cu K alpha radiation, comprising peaks at 12.2±0.2, 13.2±0.2, 15.0±0.2, 15.4±0.2, 17.6±0.2, 18.1±0.2, 19.5±0.2, 20.2±0.2, 20.9±0.2, 21.4±0.2, 23.0±0.2, 23.4±0.2, 24.4±0.2, 24.8±0.2, 25.9±0.2, 27.9±0.2, 28.9±0.2, 29.6±0.2, 30.7±0.2 degrees 2 theta.

Figure 1A:
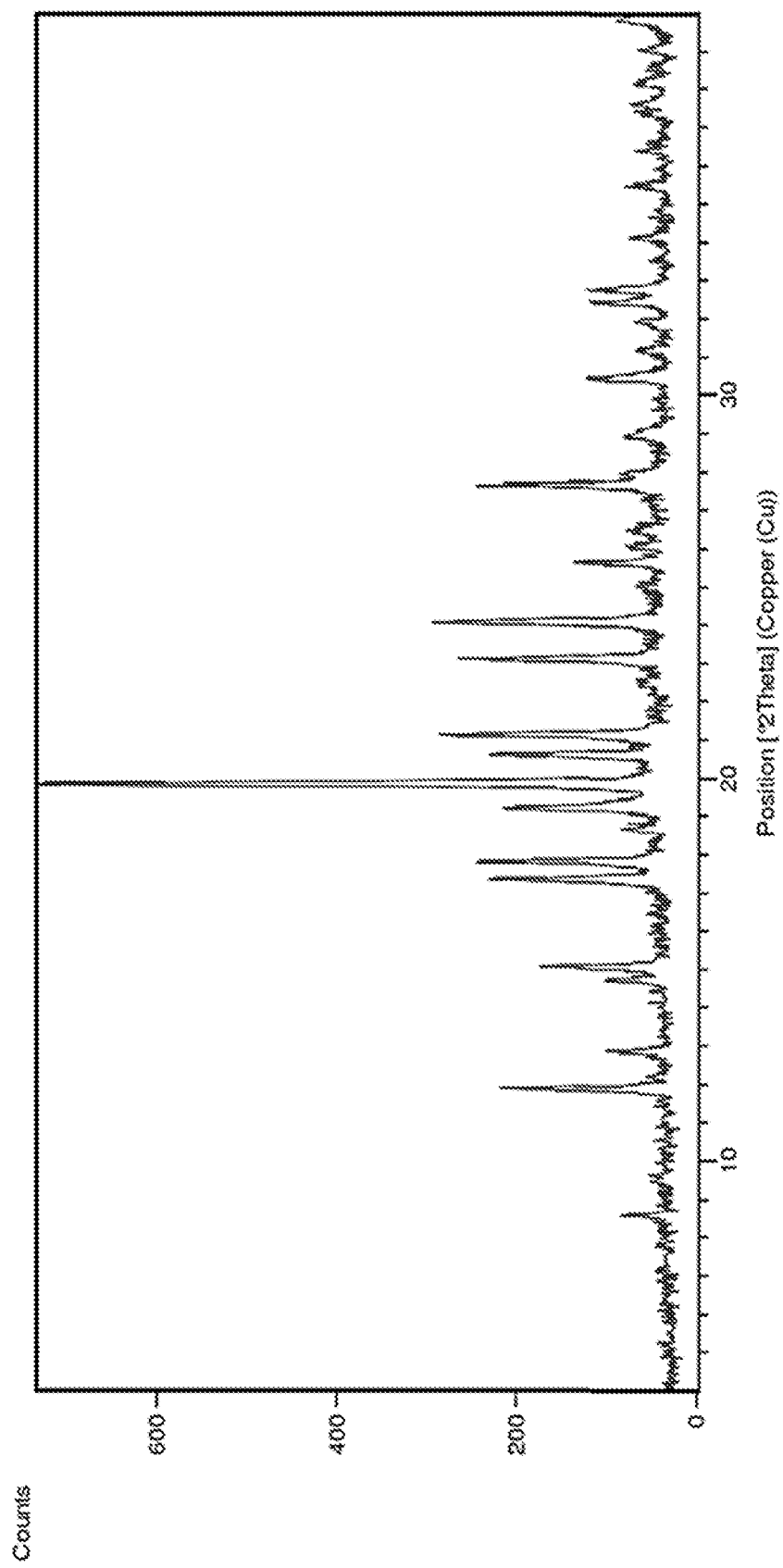
FIG. 1A and FIG. 1B (bottom panel) show representative XRPD profiles of HM04 free base crystalline Form 1 prepared as set forth in Example 1A.

Another aspect of the present disclosure relates to crystalline (R)-3-(1-(2,3-dichloro-4-(pyrazin-2-yl)phenyl)-2,2,2-trifluoroethyl)-1-methyl-1- (1-methylpiperidin-4-yl)urea free base characterized by an XRPD pattern substantially similar to the XRPD pattern of FIG. 1A as determined XRPD using Cu K alpha radiation.

Another aspect of the present disclosure relates to pharmaceutical compositions comprising a pharmaceutically acceptable carrier and at least one entity chosen from (R)-3-(1-(2,3-dichloro-4-(pyrazin-2-yl)phenyl)-2,2,2-trifluoroethyl)-1-methyl-1-(1-methylpiperidin-4-yl)urea fumarate salt and crystalline (R)-3-(1-(2,3-dichloro-4-(pyrazin-2-yl)phenyl)-2,2,2-trifluoroethyl)-1-methyl-1-(1-methylpiperidin-4- yl)urea as disclosed herein. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

Another aspect of the present disclosure includes methods for making (R)-3-(1-(2,3-dichloro-4-(pyrazin-2-yl)phenyl)-2,2,2-trifluoroethyl)-1-methyl-1-(1-methylpiperidin-4-yl) urea fumarate salt, and crystalline forms thereof, as are detailed in the Examples below.

Another aspect of the present disclosure includes methods for making crystalline (R)-3-(1-(2,3-dichloro-4-(pyrazin-2-yl)phenyl)-2,2,2-trifluoroethyl)-1-methyl-1-(1-methylpiperidin-4-yl)urea as disclosed herein.

Another aspect of the present disclosure is a method of reducing ghrelin signaling activity in a cell comprising exposing the cell to at least one entity chosen from (R)-3-(1-(2,3-dichloro-4-(pyrazin-2-yl)phenyl)-2,2,2-trifluoroethyl)-1-methyl-1-(1-methylpiperidin-4-yl)urea fumarate salt and crystalline (R)-3-(1-(2,3-dichloro-4-(pyrazin-2-yl)phenyl)-2,2,2-trifluoroethyl)-1-methyl-1-(1-methylpiperidin-4-yl)urea as disclosed herein.

The term "ghrelin signaling activity" refers to any one of or combination of the downstream activities that occurs when ghrelin binds its receptor or receptor complex.

Another aspect of the present disclosure is a method of inhibiting the release of growth hormone in a cell comprising exposing the cell to at least one entity chosen from (R)-3-(1-(2,3-dichloro-4-(pyrazin-2-yl)phenyl)-2,2,2-trifluoroethyl)-1-methyl-1-(1-methylpiperidin-4-yl)urea fumarate salt and crystalline (R)-3-(1-(2,3-dichloro-4-(pyrazin-2-yl)phenyl)-2,2,2-trifluoroethyl)-1-methyl-1-(1-methylpiperidin-4- yl)urea as disclosed herein.

Another aspect of the present disclosure is a method of inhibiting GHRS1a comprising exposing a cell to at least one entity chosen from (R)-3-(1-(2,3-dichloro-4-(pyrazin-2-yl)phenyl)-2,2,2-trifluoroethyl)-1-methyl-1-(1-methylpiperidin-4-yl)urea fumarate salt and crystalline (R)-3-(1-(2,3-dichloro-4-(pyrazin-2-yl)phenyl)-2,2,2-trifluoroethyl)-1-methyl-1-(1-methylpiperidin-4- yl)urea as disclosed herein.

In some embodiments, the cell is exposed in vitro to at least one entity chosen from (R)-3-(1-(2,3-dichloro-4-(pyrazin-2-yl)phenyl)-2,2,2-trifluoroethyl)-1-methyl-1-(1-methylpiperidin-4-yl)urea fumarate salt and crystalline (R)-3-(1-(2,3-dichloro-4-(pyrazin-2-yl)phenyl)-2,2,2-trifluoroethyl)-1-methyl-1-(1-methylpiperidin-4- yl)urea as disclosed herein. In some embodiments, the cell is exposed in vivo to at least one entity chosen from (R)-3-(1-(2,3-dichloro-4-(pyrazin-2-yl)phenyl)-2,2,2-trifluoroethyl)-1-methyl-1-(1-methylpiperidin-4-yl)urea fumarate salt and crystalline (R)-3-(1-(2,3-dichloro-4-(pyrazin-2-yl)phenyl)-2,2,2-trifluoroethyl)-1-methyl-1-(1-methylpiperidin-4-yl)urea as disclosed herein.

Another aspect of the present disclosure is a method of treating a subject having a condition or disorder associated with an increase in ghrelin level comprising administering to the subject at least one entity chosen from (R)-3-(1-(2,3-dichloro-4-(pyrazin-2-yl)phenyl)-2,2,2-trifluoroethyl)-1-methyl-1-(1-methylpiperidin-4-yl)urea fumarate salt and crystalline (R)-3-(1-(2,3-dichloro-4-(pyrazin-2-yl)phenyl)-2,2,2-trifluoroethyl)-1-methyl-1-(1-methylpiperidin-4-yl)urea as disclosed herein. By way of non-limiting example, a condition or disorder associated with increased ghrelin level may include food abuse disorders, such as binge eating, obesity, hyperphagia (uncontrollable appetite), post-dieting body weight rebound (including post-dieting hyperphagia, alcohol addition, and genetic diseases, such as Prader-Willi syndrome, etc.

Another aspect of the present disclosure is a method of treating a subject having a condition or disorder associated with an increase in circulating growth hormone comprising administering to the subject at least one entity chosen from (R)-3-(1-(2,3-dichloro-4-(pyrazin-2-yl)phenyl)-2,2,2-trifluoroethyl)-1-methyl-1-(1-methylpiperidin-4-yl)urea fumarate salt and crystalline (R)-3-(1-(2,3-dichloro-4-(pyrazin-2-yl)phenyl)-2,2,2-trifluoroethyl)-1-methyl-1-(1-methylpiperidin-4- yl)urea as disclosed herein.

To "reduce" or "inhibit" means to decrease, reduce, or arrest an activity, function, or amount as compared to a reference. In some embodiments, by "reduce" or "inhibit" is meant the ability to cause an overall decrease of 20% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control dose (such as a placebo) over the same period of time. A "reference" as used herein, refers to any sample, standard, or level that is used for comparison purposes. A reference may be obtained from a healthy or non-diseased sample. In some examples, a reference is obtained from one or more healthy subjects, which are not the subject being tested or treated.

The term "substantially reduced" denotes a sufficiently high degree of reduction between a numeric value and a reference numeric value such that one of skill in the art would consider the difference between the two values to be of statistical significance within the context of the biological characteristic measured by said values. In some embodiments, the substantially reduced numeric values is reduced by greater than about any one of 10%, 15%, 20%, 25%, 30%, 35%, 40%, 45%, 50%, 60%, 70%, 80%, 90%, 95%, or 100% compared to the reference value.

In some embodiments, the exposure of a cell or a subject to at least one entity chosen from (R)-3-(1-(2,3-dichloro-4-(pyrazin-2-yl)phenyl)-2,2,2-trifluoroethyl)-1-methyl-1-(1-methylpiperidin-4-yl)urea fumarate salt and crystalline (R)-3-(1-(2,3-dichloro-4-(pyrazin-2-yl)phenyl)-2,2,2-trifluoroethyl)-1-methyl-1-(1-methylpiperidin-4- yl)urea as disclosed herein results in a reduction of ghrelin signaling activity. In some embodiments, ghrelin signaling activity in a cell or in a subject is reduced by at least 10%, at least 15%, at least 20%, at least 25%, at least 30%, at least 35%, at least 40%, at least 45%, at least 50%, at least 60%, at least 70%, at least 80%, at least 90%, at least 95%, or 100% compared to ghrelin signaling activity in the absence of (R)-3-(1-(2,3-dichloro-4-(pyrazin-2-yl)phenyl)-2,2,2-trifluoroethyl)-1-methyl-1-(1-methylpiperidin-4-yl)urea fumarate salt or crystalline (R)-3-(1-(2,3-dichloro-4-(pyrazin-2-yl)phenyl)-2,2,2-trifluoroethyl)-1-methyl-1-(1-methylpiperidin-4-yl)urea.

In some embodiments, ghrelin signaling activity is measured by level of intracellular calcium detected by fluorescence imaging plate reader (FLIPR) assay. In some embodiments, the exposure to at least one entity chosen from (R)-3-(1-(2,3-dichloro-4-(pyrazin-2-yl)phenyl)-2,2,2-trifluoroethyl)-1-methyl-1- (1-methylpiperidin-4-yl)urea fumarate salt and crystalline (R)-3-(1-(2,3-dichloro-4-(pyrazin-2-yl)phenyl)-2,2,2-trifluoroethyl)-1-methyl-1-(1-methylpiperidin-4- yl)urea as disclosed herein results in a reduction in the level of intracellular calcium.

FLIPR assay refers to a technique of detecting G-protein coupled receptor (e.g., GHS-R1a among others) activation and stimulation of intracellular calcium flux. Intracellular calcium levels can be measured using calcium-sensitive dyes and a fluorescence plate reader. For further descriptions, see Arkin, Michelle R., et al. (2012). FLIPR™ Assays for GPCR and Ion Channel Targets. In *Assay Guidance Manual* [Internet] Sittampalam G. S., et al. (Eds).

In some embodiments, ghrelin signaling activity is measured by level of circulating growth hormone. In some embodiments, the exposure of a subject to at least one entity chosen from (R)-3-(1-(2,3-dichloro-4-(pyrazin-2-yl)phenyl)-2,2,2-trifluoroethyl)-1-methyl-1-(1-methylpiperidin-4-yl)urea fumarate salt and crystalline (R)-3-(1-(2,3-dichloro-4-(pyrazin-2-yl)phenyl)-2,2,2-trifluoroethyl)-1-methyl-1-(1-methylpiperidin-4- yl)urea as disclosed herein results in a reduction in the level of circulating growth hormone.

In some embodiments, ghrelin signaling activity is measured by food intake. In some embodiments, the exposure of a subject to at least one entity chosen from (R)-3-(1-(2,3-dichloro-4-(pyrazin-2-yl)phenyl)-2,2,2-trifluoroethyl)-1- methyl-1-(1-methylpiperidin-4-yl)urea fumarate salt and crystalline (R)-3-(1-(2,3-dichloro-4-(pyrazin-2-yl)phenyl)-2,2,2-trifluoroethyl)-1-methyl-1-(1-methylpiperidin-4-yl)urea as disclosed herein results in a reduction in food intake.

In some embodiments, ghrelin signaling activity is measured by body weight. In some embodiments, the exposure of a subject to at least one entity chosen from (R)-3-(1-(2,3-dichloro-4-(pyrazin-2-yl)phenyl)-2,2,2-trifluoroethyl)-1-methyl-1-(1-methylpiperidin-4-yl)urea fumarate salt and crystalline (R)-3-(1-(2,3-dichloro-4-(pyrazin-2-yl)phenyl)-2,2,2-trifluoroethyl)-1-methyl-1-(1-methylpiperidin-4-yl)urea as disclosed herein results in a reduction in body weight or a stabilization of body weight.

"Treatment" or "treating" is an approach for obtaining beneficial or desired clinical results. "Treatment" or "treating" covers any administration or application of a therapeutic for disease in a mammal, including humans. For purposes of this disclosure, beneficial or desired clinical results include, but are not limited to, any one or more of: alleviation of one or more symptoms, diminishment of extent of condition, preventing or delaying recurrence of condition, delay or slowing of condition progression, amelioration of the condition state, inhibiting the condition or progression of the condition, arresting development of the condition, and remission (whether partial or total) of the condition. Also encompassed by "treatment" or "treating" is a reduction of pathological consequence of a condition. The methods provided herein contemplate any one or more of these aspects of treatment. In-line with the above, the term treatment does not require one-hundred percent removal of all aspects of a condition or disorder.

Another aspect of the present disclosure is orally administering a composition as disclosed herein for treatment of a condition or disorder associated with an increased level of circulating ghrelin.

Another aspect of the present disclosure is orally administering a composition as disclosed herein for treatment of a disease or disorder associated with an increased level of circulating growth hormone.

Therapeutically effective amounts and dosing regimens for oral dosing using the salts as disclosed herein will vary depending on a variety of factors including condition or disorder to be treated, as well as age, weight, possibly gender, and other health factors of the patient, which may be determined at the time of treatment. Therapeutically effective amounts may range from 1 mg to 500 mg. Oral dosage compositions can contain, by way of non-limiting example, 1, 5, 10, 15, 20, 25, 30, 50, 75, 100, 150, 200, 250, 300, 350, 400, 450, or 500 mg of active ingredient as disclosed herein.

TABLE 1

Abbreviations and names used in the following examples and elsewhere herein include:

| Abbreviation/Chemical Name | Name |
| --- | --- |
| atm | atmospheres |
| ACN | acetonitrile |
| Boc | t-butoxycarbonyl |
| $CDCl_3$ | deuterated chloroform |
| CDI | 1,1'-Carbonyldiimidazole |
| D-CSA | D-camphorsulfonic acid |
| DCM | dichloromethane |
| DME | dimethoxyethane |
| CO (g) | carbon monoxide gas |
| DABCO | 1,4-diazabicylo[2.2.2]octane |

TABLE 1-continued

Abbreviations and names used in the following examples and elsewhere herein include:

| Abbreviation/Chemical Name | Name |
| --- | --- |
| DCM | Dichloromethane |
| DIBAL-H | Diisobutylaluminium hydride |
| DMA | N,N-dimethylacetamide |
| DMF | N,N-dimethylformamide |
| DMSO | dimethylsulfoxide |
| DSC | Differential Scanning Calorimetry |
| eq. | equivalents |
| $Et_3N$ | triethylamine |
| $Et_2O$ | diethyl ether |
| EtOAc | ethyl acetate |
| EtOH | ethanol |
| GVS | Gravimetric Vapor Sorption |
| h | hours |
| $H_2O$ | water |
| HCl | hydrochloric acid |
| HPLC | high pressure liquid chromatography |
| LC-MS/MS | (high pressure) liquid chromatography tandem mass spectrometry |
| IPA | isopropanol |
| IPC | In-process control |
| i.v. | intravenous |
| $K_2CO_3$ | potassium carbonate |
| MeOH | Methanol |
| MEK | methyl ethyl ketone |
| MgSO4 | magnesium sulfate |
| MIBK | methyl isobutyl ketone |
| min | minutes |
| $Na_2CO_3$ | Sodium carbonate |
| $Na_2SO_4$ | sodium sulfate |
| NaH | sodium hydride |
| $NaHCO_3$ | sodium bicarbonate |
| NaOH | sodium hydroxide |
| $NH_4HCO_3$ | ammonium bicarbonate |
| $NH_4OH$ | ammonium hydroxide |
| NMP | N-Methyl-2-pyrrolidone |
| NMR | Nuclear Magnetic Resonance |
| p.o. | oral |
| Pd/C | Palladium on carbon |
| $Pd(dppf)Cl_2$ | [1,1'-bis(diphenylphosphino)ferrocene]dichloropalladium(II) |
| RT | room temperature |
| RH | relative humidity |
| STA | Simultaneous Thermal Analysis |
| t-BuOH | tert-butanol |
| TBAA | tert-butyl acetoacetate |
| TBME | tert-Butyl methyl ether |
| THF | tetrahydrofuran |
| XRPD | X-Ray Powder Diffraction |

EXAMPLES

Example 1

Figure 1B:
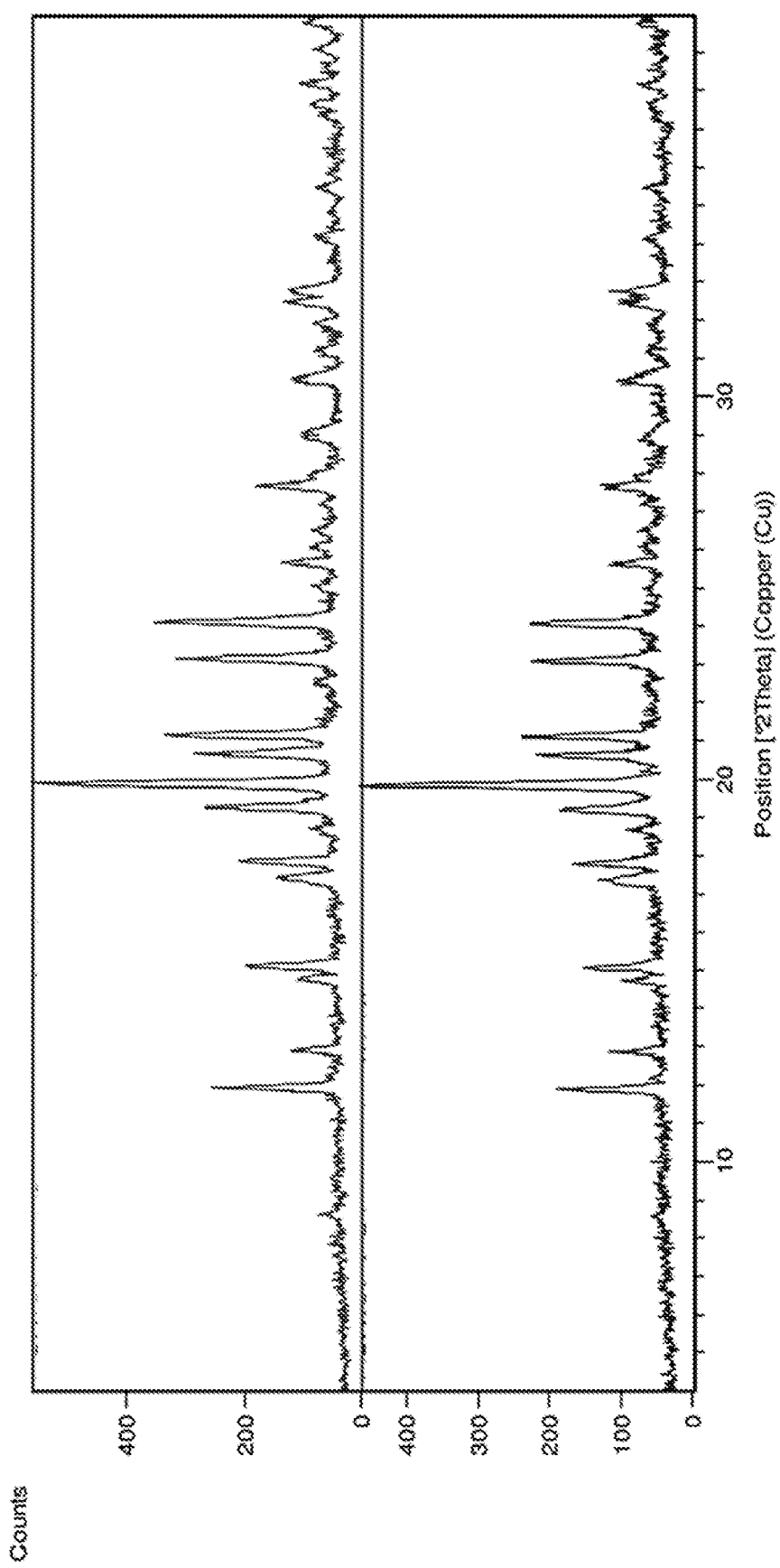

Preparation and Characterization of Crystalline Form 1 (R)-3-(1-(2,3-dichloro-4-(pyrazin-2-yl)phenyl)-2,2,2-trifluoroethyl)-1-methyl-1-(1-methylpiperidin-4-yl) Urea (HM04) Free Base Example 1A Preparation of HM04 Free Base Crystalline Form 1 Seed A first 15 mg sample of amorphous free base of (R)-3-(1-(2,3-dichloro-4-(pyrazin-2-yl)phenyl)-2,2,2-trifluoroethyl)-1-methyl-1-(1-methylpiperidin-4-yl) urea, also referred to as HM04 or H0900, was dissolved in acetonitrile and a second 15 mg sample of amorphous free base HM04 was dissolved in acetone. The solutions were allowed to evaporate slowly in a desiccator under nitrogen flow. Crystallinity was confirmed by X-ray powder diffraction (XRPD). The XRPD profile (Form 1) of the free base HM04 samples crystallized from the acetonitrile solution and from the acetone solution are shown in FIGS. 1A and 1B (bottom panel), respectively.

Example 1B

Scale-Up of HM04 Free Base Crystalline Form 1

A sample of amorphous HM04 free base was dissolved in 0.5 mL acetone and the solution allowed to evaporate slowly in a desiccator under nitrogen flow. After 24 hours, a brown oily residue was obtained, which was seeded with a few crystals of the free base Form 1 crystallized from the acetone solution (see Example 1A) and scratched with a spatula. The oil solidified and the resulting product was dried in a vacuum oven at 50° C. for 24 hours to yield 95 mg yield of crystalline free base.

Crystallinity was confirmed by X-ray powder diffraction (XRPD), see FIG. 1B, top panel. Simultaneous thermal analysis (STA) suggested that the crystalline free base was not hydrated or solvated. The crystalline free base had an estimated melt onset of approximately 155° C., as determined by DSC). GVS analysis indicated that the product was slightly hygroscopic with a reversible weight gain of approximately 1.5% up to 70% relative humidity (RH) and approximately 2% up to 80% RH. The aqueous solubility of the crystalline free base was estimated to be less than 2 mg/mL.

Example 2

Small Scale Preparation of HM04 Fumarate Salt Form 1

HM04 amorphous free base (100 mg) was suspended in acetonitrile (2 mL). Fumaric acid (27 mg) was added, washing residual acid into the reaction mixture with extra acetonitrile (0.2 mL) and mixed well. The mixture was warmed gently and a solid was precipitated rapidly. The resulting suspension was temperature-cycled between 40° C. and room temperature overnight (18-24 hours). The product was filtered, washed with acetonitrile (0.2 mL), and dried in a vacuum oven at 50° C. for 24 hours to yield 86 mg of the fumarate salt product.

Figure 1C:
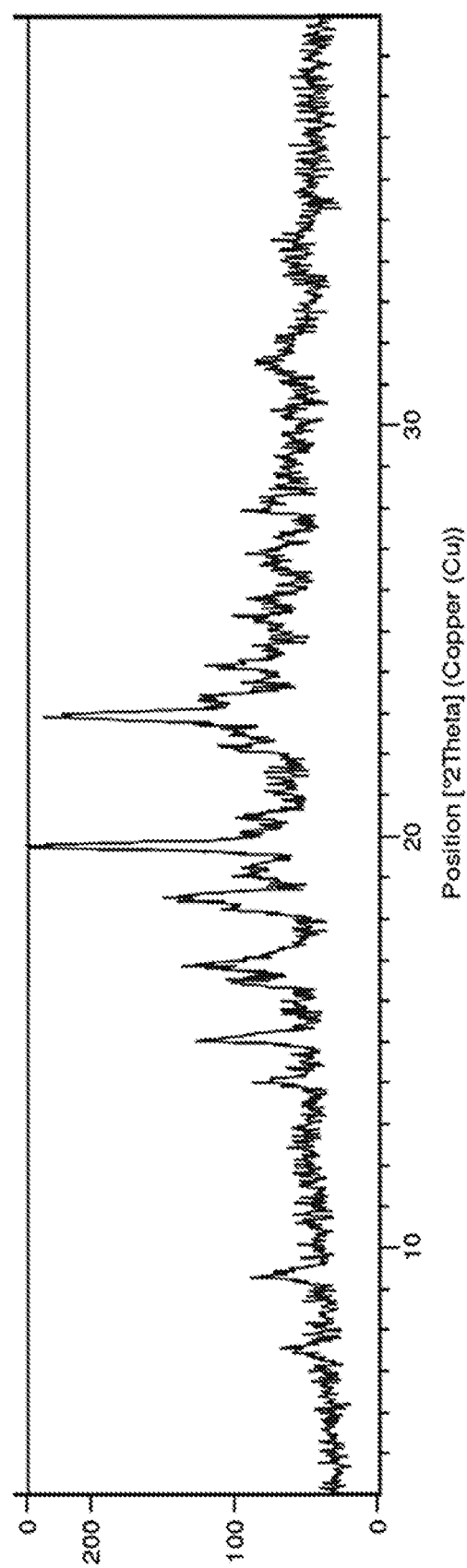
FIG. 1C shows a representative XRPD profile of HM04 fumarate salt crystalline Form 1 prepared as set forth in Example 2.

The fumarate salt product was shown to be a 1:1 salt by nuclear magnetic resonance (NMR) analysis. Crystallinity was confirmed by XRPD and designated as Form 1 (FIG. 1C). STA showed no weight loss before the melt suggesting that the product was not hydrated or solvated. DSC showed a single endotherm corresponding to a melt onset of approximately 172° C. GVS showed the fumarate salt was hygroscopic with a weight gain of approximately 2.8% up to 70% relative humidity (RH) and approximately 4.5% up to 80% RH. The estimated aqueous solubility of the fumarate salt was greater than 200 mg/mL.

Example 3

Crystalline Forms of HM04 Fumarate Salt (Forms 1 and 2)

Figure 2:
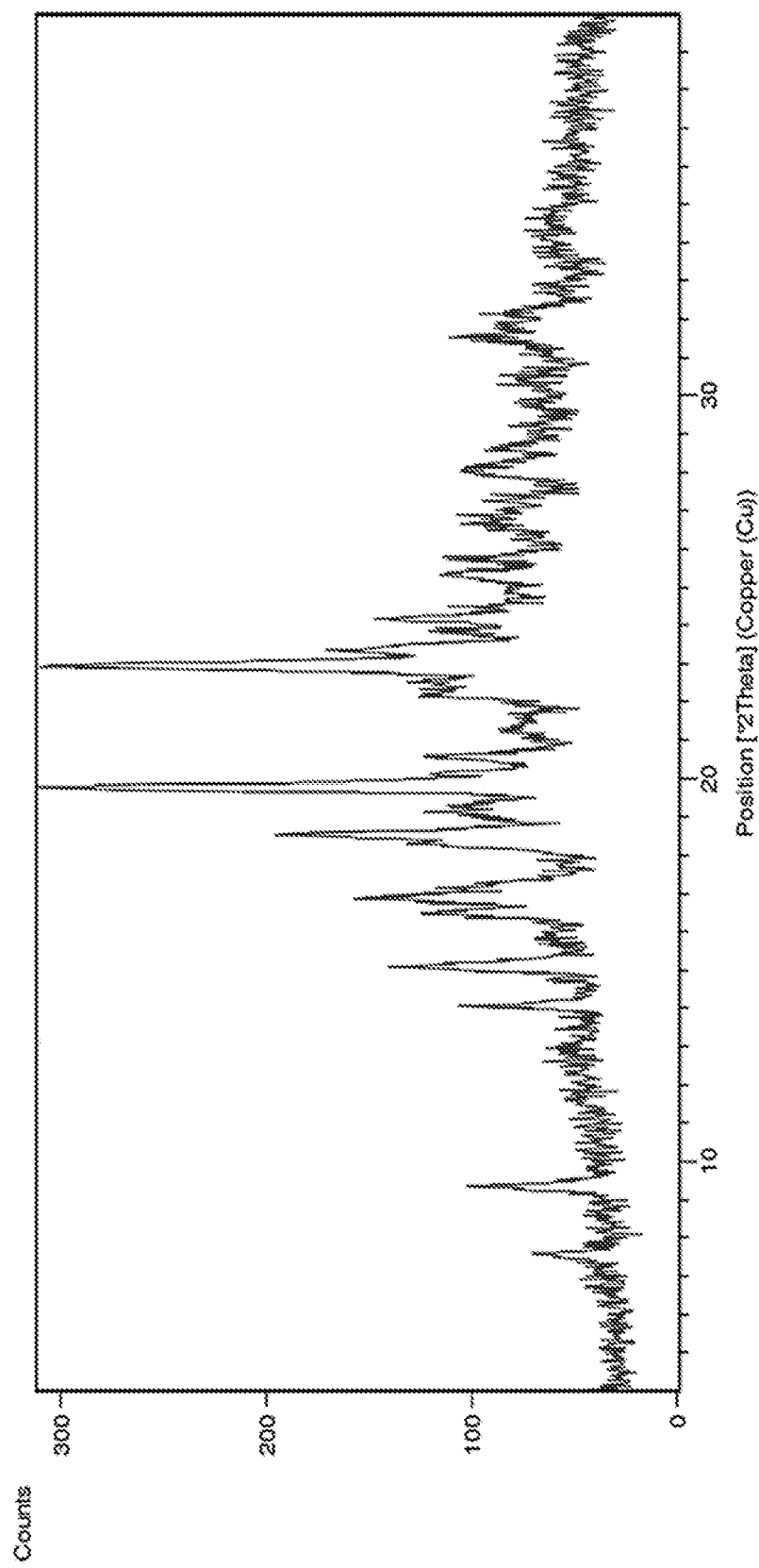
FIG. 2 shows a representative XRPD profile of HM04 fumarate salt crystalline Form 1 prepared as set forth in Example 3.

HM04 free base (1.5 mg) was suspended in acetonitrile (6 mL) and fumaric acid (0.4 g) was added. The mixture was warmed gently and a solid was precipitated rapidly. The resulting suspension was temperature-cycled between 40° C. and ambient temperature over 72 hours. More acetonitrile (1 mL) was added and the product was filtered, washed with acetonitrile (5×0.2 mL) and dried in a vacuum oven at 50° C. for at least 24 hours to constant weight to yield 1.6 g of fumarate salt. This crystalline HM04 fumarate salt was characterized by XRPD analysis as Form 1 (FIG. 2).

FIG. 3 shows a representative XRPD pattern of an HM04 fumarate salt Form 2 sample obtained after dissolving the HM04 fumarate salt in ethanol and evaporating the solvent at room temperature under nitrogen.

HM04 fumarate salt Form 2 was scaled up by dissolving 150 mg of the starting material (HM04 fumarate salt Form 1) in 0.45 mL of an 90/10 ethanol/water mixture under heat. The solution was evaporated in a desiccator under nitrogen flow for 96 hours and a solid product was recovered. The XRPD pattern of the Form 2 scaled-up product was generally consistent with the product on the smaller scale, although the possibility of a mixture with a small amount of Form 1 could not be ruled out. NMR analysis showed that the product was consistent with a stoichiometric mono salt. STA data showed a weight loss of approximately 1.9% between 70° C. and 150° C., which suggested that the sample was possibly a hydrate. The DSC data showed a broad endotherm with onset at approximately 164.5° C., which corresponded to the melt. GVS showed a 3.5% weight gain up to 70% RH and 4.9% weight gain up to 80% RH. No change in the XRPD pattern was observed after GVS or after the sample was placed in a desiccator at 40° C./75% RH for 7 days.

Competitive slurry experiments were performed by mixing the Form 1 starting material and the Form 2 scaled-up material in approximately 50:50 ratio (10 mg:10 mg). The mixtures were shaken in 100 µL of different solvents or solvent mixtures at room temperature for 48 hours. A sample of the solid was taken from each of the slurries after 48 hours, following evaporation of the solvent(s), and analyzed by XRPD to determine if conversion to one form had occurred. The slurries were repeated at 60° C. and samples were again taken after 48 hours. The results of the study at room temperature and at 60° C. are shown in Table 2, below.

TABLE 2

| Solvent(s) | 48 hours/RT | 48 hours/60° C. |
| --- | --- | --- |
| Acetonitrile | Form 1 | Form 1 |
| Acetonitrile:water (95:5) | Form 1 | Unknown |
| Ethanol | Forms 1 & 2 | Unknown |
| Ethanol:water (95:5) | Form 2 | Oil |

Figure 4:
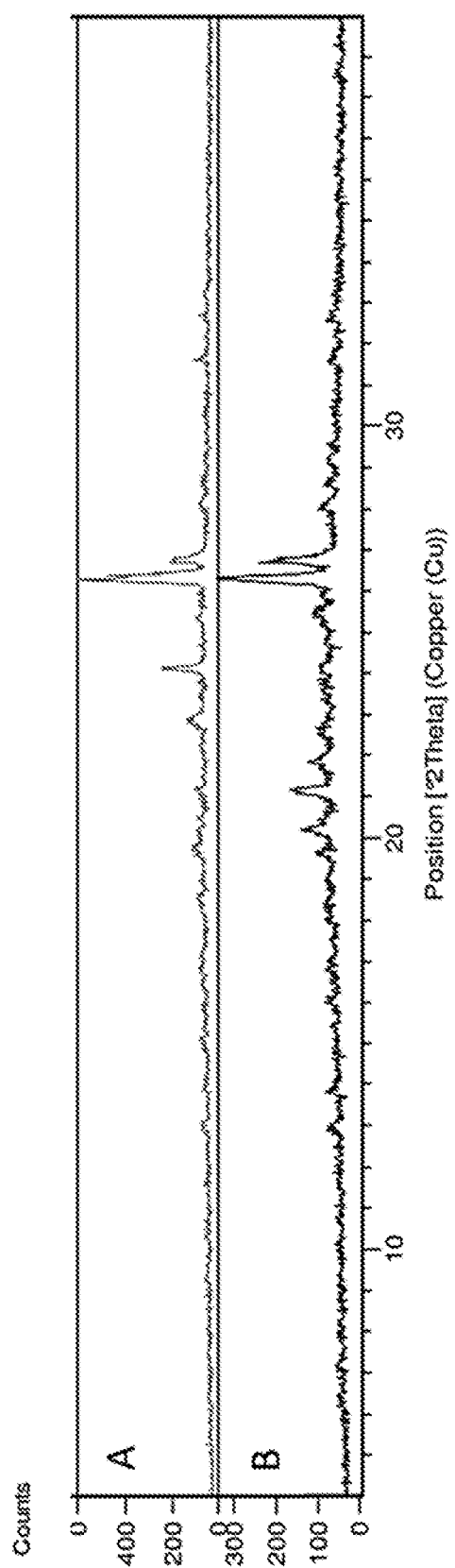
FIG. 4A shows the XRPD profile observed after mixing HM04 fumarate salt Forms 1 and 2 at a 50:50 ratio in acetonitrile:water (95:5) for 48 hours at 60° C.
FIG. 4B shows the XRPD profile observed after mixing HM04 fumarate salt Forms 1 and 2 at a 50:50 ratio in ethanol for 48 hours at 60° C.

Competitive slurries in acetonitrile at room temperature resulted in complete conversion to Form 1. Slurries in ethanol resulted in a mixture of forms and ethanol/water at ambient temperature resulted in conversion to Form 2. Competitive slurries in acetonitrile at 60° C. resulted in complete conversion to Form 1. There was an unassigned XRPD pattern observed at 60° C. with slurries in acetonitrile/water and in ethanol (FIGS. 4A and 4B, respectively). Further investigations into the results of the competitive slurries were not conducted.

Example 4

Analytical Methods for Examples 1-3

The analytical methods used to characterize the products described in Examples 1-3 are set forth below.

STA was conducted using a Perkin-Elmer STA 600 TGA/DTA analyzer. The sample (5 mg) was heated from 25° C. to 300° C. at a rate of 10° C./min, during which time the change in weight was monitored. Nitrogen was used as the purge gas at a flow rate of 20 cm³/min.

For the DSC analysis, 5 mg of sample was weighed into an aluminum DSC pan and sealed non-hermetically with an aluminum lid. The sample was then loaded into a Perkin-Elmer Jade DSC and held at 25° C. until a stable heat-flow response was obtained. The sample was then heated to 300° C. at a scan rate of 10° C./min and the resulting heat flow response was monitored. A 20 cm³/min helium purge was used. Prior to analysis, the instrument was temperature and heat flow verified using an indium standard.

For the GVS analysis, 15-20 mg of sample was loaded into an IgaSorp vapour sorption balance (Hiden Analytical Instruments). The sample was then dried by maintaining a 0% humidity environment until no further weight change was recorded. The sample was then subjected to a ramping profile from 0 to 90% RH at 10% RH increments, maintaining the sample at each step until equilibration had been attained (99% step completion). Upon reaching equilibrium, the % RH within the apparatus was ramped to the next step and the equilibration procedure repeated. After completion of the sorption cycle, the sample was dried using the same procedure. The weight change during the sorption/desorption cycles were then monitored, allowing for the hygroscopic nature of the sample to be determined.

NMR analysis was run in DMSO-d⁶ using a Bruker Avance III 400 instrument.

XRPD analyses were performed by gently compressing a sample (approximately 2 mg) on the XRPD zero-background, single, obliquely cut, silica sample holder. The sample was then loaded into a Philips X-Pert MPD diffractometer and using the following experimental conditions:

Tube anode: Cu
Generator tension: 40 kV
Tube current: 40 mA
Wavelength alpha1: 1.5406 Å
Wavelength alpha2: 1.5444 Å
Start angle (2 theta): 4
End angle (2 theta): 40
Continuous scan Example 5

Scaled-up Synthesis of HM04 Fumarate Salt Form 1

Figure 5:
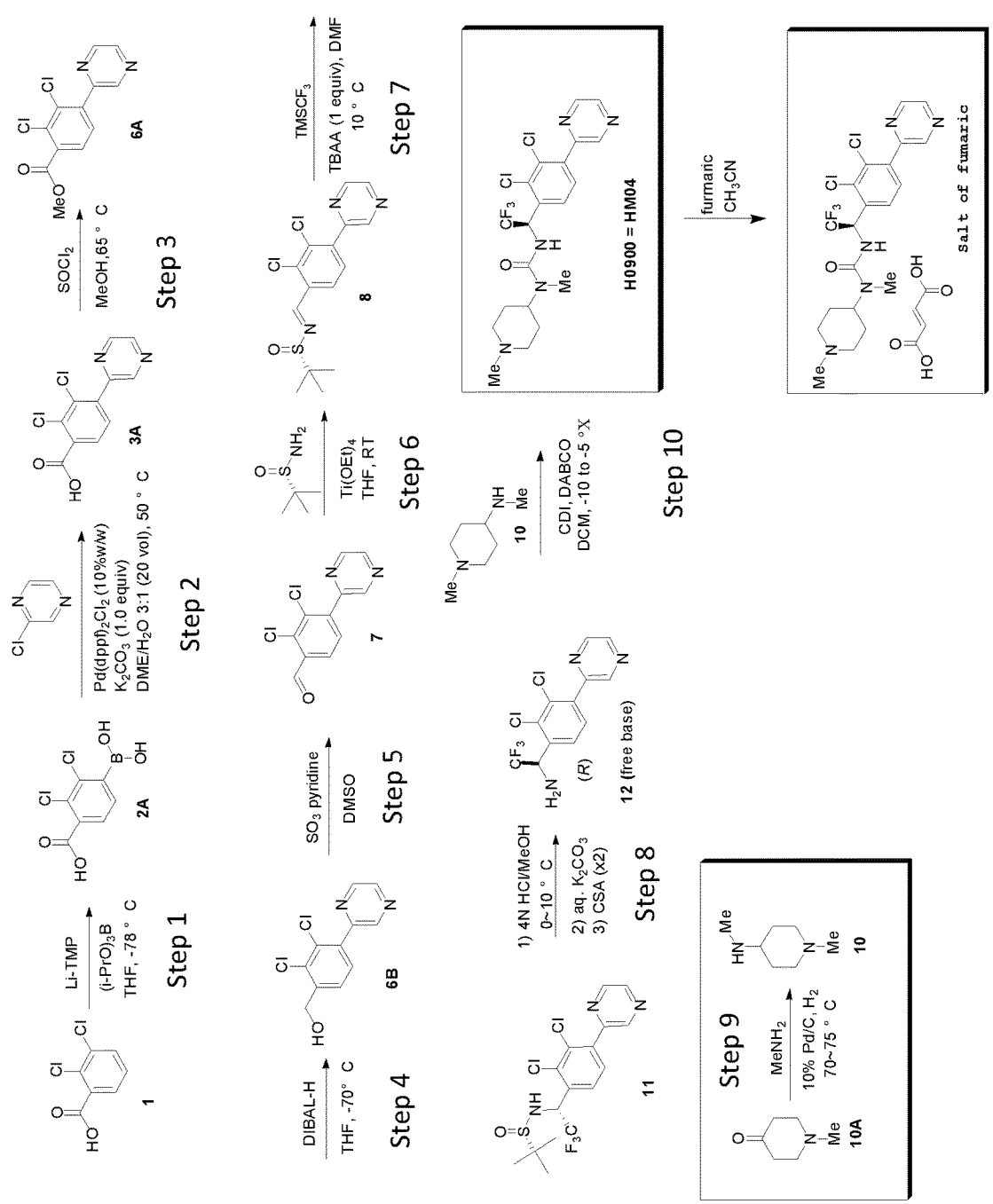
FIG. 5 provides an overview of a scaled-up synthesis method of HM04 fumarate salt Form 1 and is described in further detail in Example 5.
Figure 6:
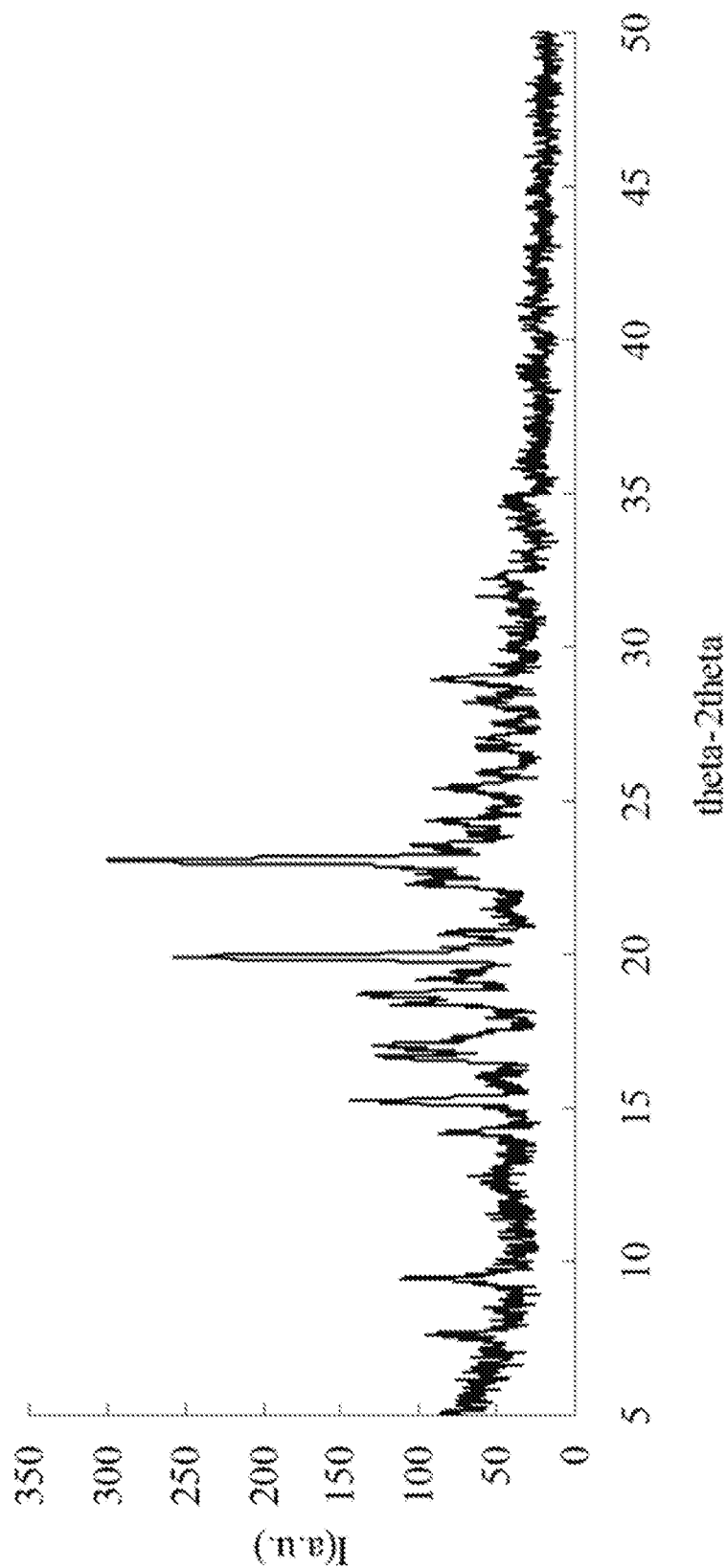
FIG. 6 shows a representative XRPD profile of HM04 fumarate salt crystalline Form 1 prepared as set forth in Example 5 (after drying at 60° C. for 6 hours).
Figure 7:
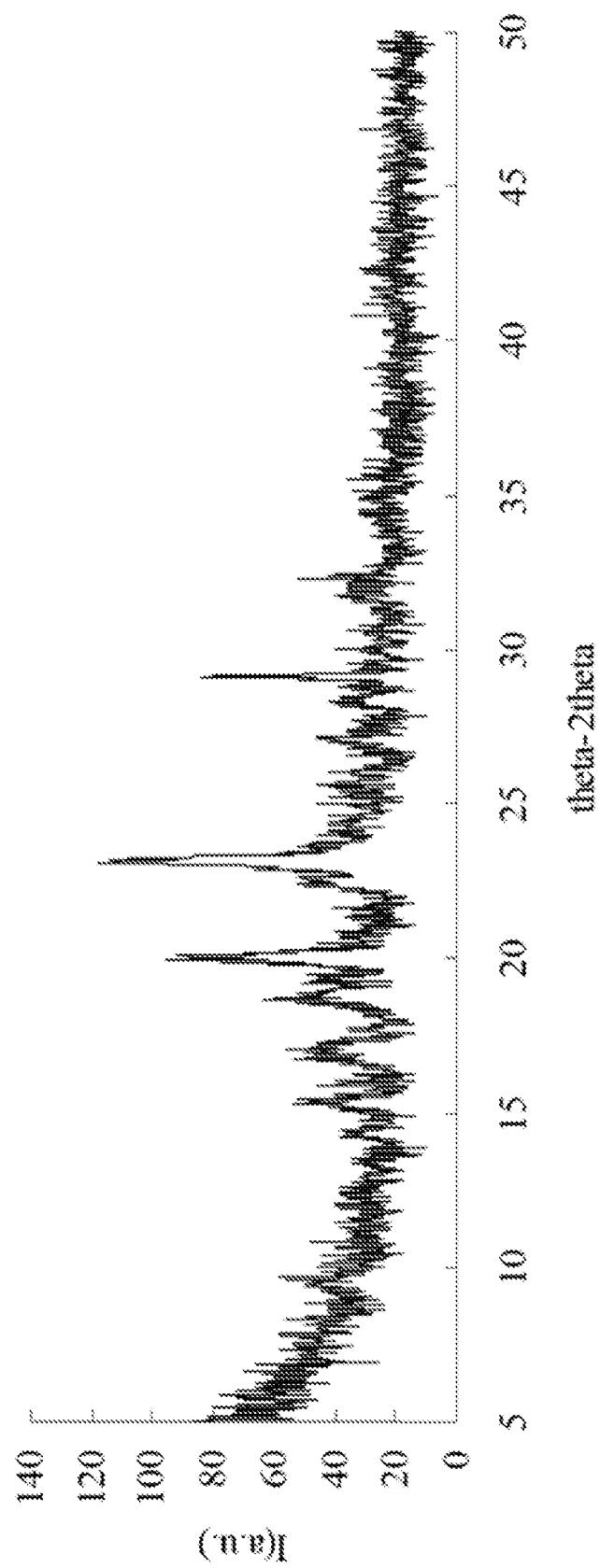
FIG. 7 shows a representative XRPD profile of HM04 fumarate salt crystalline Form 1 prepared as set forth in Example 5 (after drying at 60° C. for 15 hours).
Figure 8:
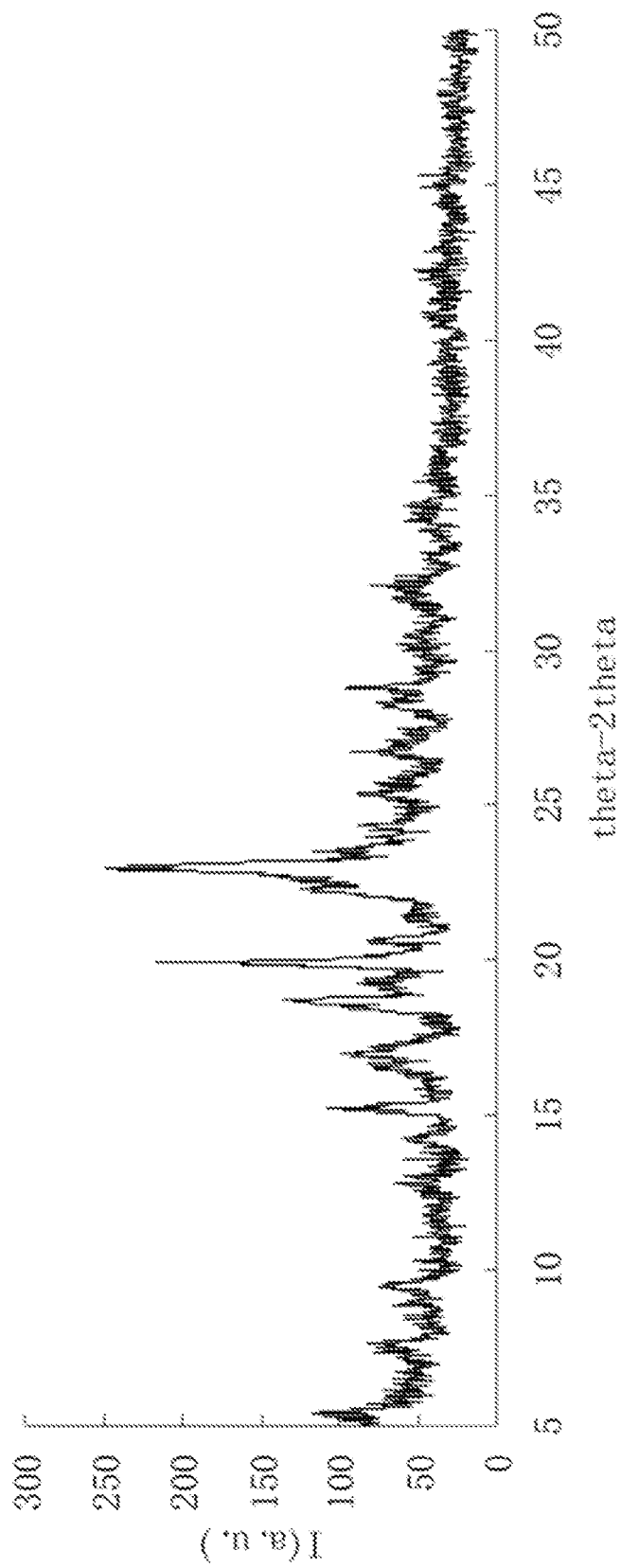
FIG. 8 shows a representative XRPD profile of HM04 fumarate salt crystalline Form 1 prepared as set forth in Example 5 (after drying at 60° C. for 72 hours).
Figure 9:
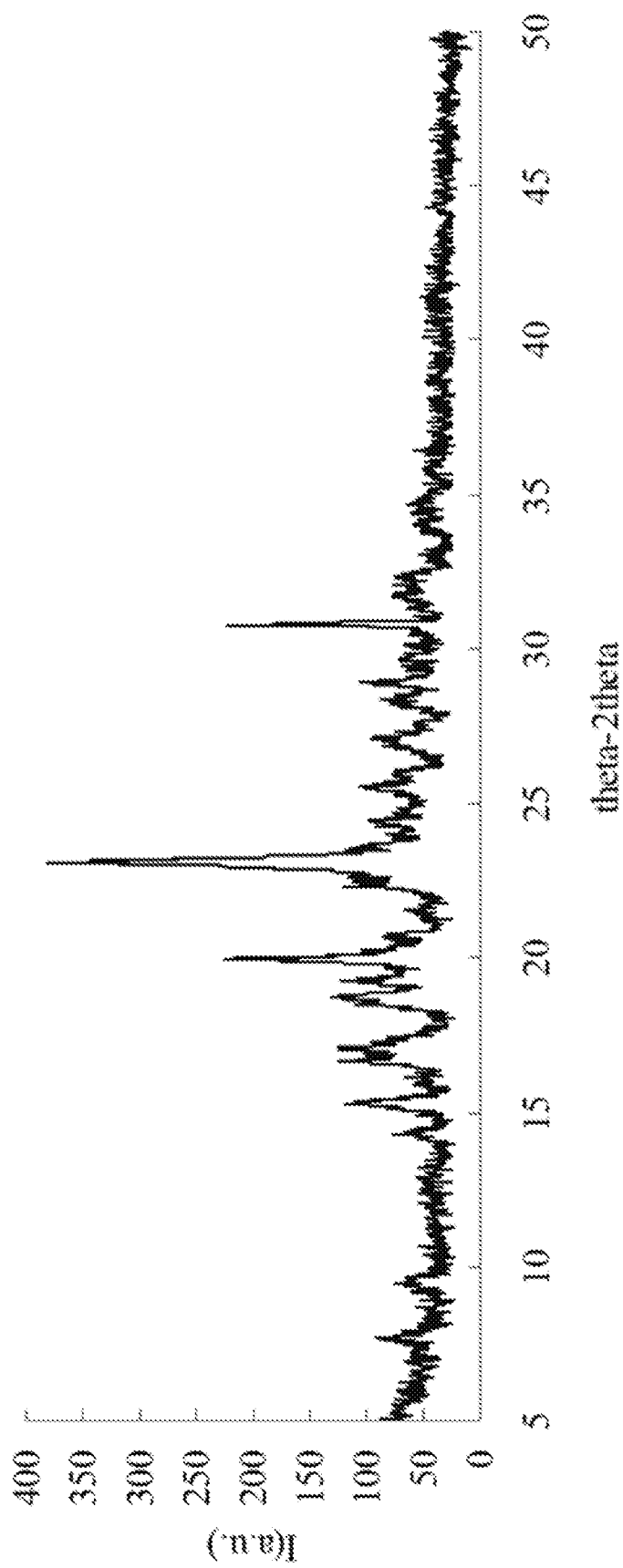
FIG. 9 shows a representative XRPD profile of HM04 fumarate salt crystalline Form 1 prepared as set forth in Example 5 (after drying at 65° C. for 18 hours).

The overview of the synthesis of HM04 fumarate salt Form 1 as set forth in this Example is shown in FIG. 5.

Step 1: Synthesis of Compound 2A

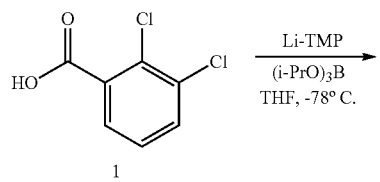

-continued

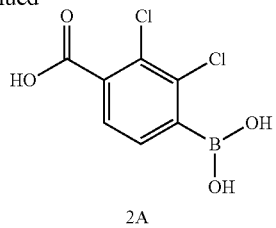

2,2,6,6-tetramethylpiperidine (7.20 kg, 51.1 mol, 3.0 eq., KF=0.30%) was added into a 100 L reactor equipped with a temperature probe and overhead stirrer and mixed at RT under nitrogen protection. THF (50 L) was added into the reactor and stirred. The vessel was purged with nitrogen three times and cooled to 0° C. n-BuLi (20.4 L, 3.0 eq.; 2.5 M hexane solution) was added to the mixture dropwise while keeping the temperature at about 0° C. to about 5° C. for over one hour. The color of the solution turned yellow. The mixture was stirred at about 0° C. to about 5° C. for 30 minutes. The mixture was cooled to about −78° C. to about −70° C. to form Solution A.

Compound 1 (3.25 kg, 17.0 mol. 1.0 eq., KF=0.03%) was dissolved in 15 L of THF to form Solution B.

Solution B was added to solution A dropwise at a temperature of about −70° C. to about −78° C. over one hour and then stirred for 30 minutes to form solution C. Tri-isopropyl borate ((i-PrO)₃B) (3.52 kg, 18.7 mol., 1.1 eq.) was added dropwise into solution C over 10 minutes. The reaction mixture was stirred at a temperature of about −70° C. to about −78° C. for one hour. HCl (40 L, 3M, 7.0 eq.) was added over 30 minutes to quench the reaction. A 10 degree rise in temperature was noted.

The resulting aqueous layer was separated and extracted with EtOAc (40 L). The aqueous layer was separated and extracted twice again with EtOAc (35 L, 30 L). The organic layers were combined resulting in about 160 L of liquid. The combined organic layer was washed twice with 50 L of a 1M aqueous HCl solution saturated with NaCl. The organic layer was concentrated to about 5 L in a 50 L rotavapor at a temperature of about 50° C. to about 55° C. under 30-40 mmHg for about 8 hours.

The residual EtOAc was swapped with DME for 3 times (10 L×3). The organic layer was concentrated in the 50 L rotavapor at a temperature of about 50° C. to about 55° C. under 30-40 mmHg for about 6 hours. Each time about 5 L of residual remained. DME (20 L) was added to the residual to obtain a deep brown solution of 14.2% compound 2A (3.55 kg in 25 kg of solution; 88.8% yield; 97.4% purity (AUC by HPLC, retention time=1.6 minutes); 0.24% residual ethyl acetate). 1H-NMR (400 MHz, DMSO): δ=8.55 (s, 2H), 7.36 (d, 1H), 7.69 (d, 1H). A second batch of compound 2A was prepared by the same method to produce 3.29 kg (95.4% purity, 82.3% yield, 0.11% residual ethyl acetate).

Step 2: Synthesis of Compound 3A

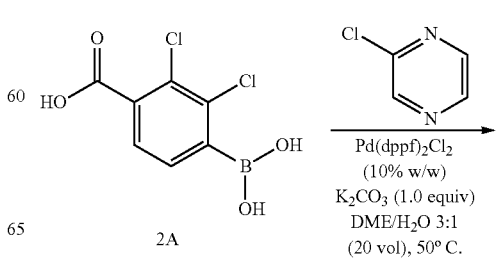

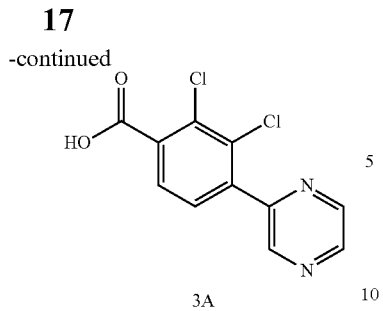

3A

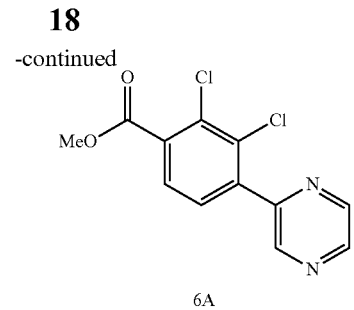

6A

Compound 2A (2.91 kg in 20.5 kg solution) was added into a 100 L reactor at room temperature under nitrogen. DME (45 mL), 2-chloropyrazin (1.42 kg, 12.4 mol., 1.0 eq.), and Pd(dppf)Cl$_2$ (10% w/w, 291 g) were added sequentially, and each mixed at room temperature under nitrogen. Nitrogen was bubbled into the mixture for 20 minutes and the resulting mixture was purged and filled with nitrogen (3 times). The mixture was heated to 48-52° C. over 60 minutes. K$_2$CO$_3$ (2.57 kg, 18.6 mol, 1.5 eq.) was added to 22 L of water in another reactor at room temperature and then added dropwise to the compound 2A mixture over 10 minutes. The mixture was stirred at 48-52° C. for 16 hours and then cooled to room temperature. This procedure was repeated twice and all three batches were combined.

An aqueous solution of K$_2$CO$_3$ (1.0 kg) was dissolved in 22 L of water and added to the combined mixture to adjust the pH to 9. TBME (50 L) was added into the mixture and filtered (PET filter, 3-5 μm, 205 g/m$^2$) to remove about 50 g of sticky, brown solid material (catalyst analog). The aqueous layer was twice separated and extracted with TBME (40 L, 40 L).

The aqueous layer was combined with the aqueous layer of a fourth batch prepared according to the above method. The pH of the combined aqueous layers was adjusted to pH<3 with HCl (2N, 48 L). The solid precipitated out slowly as the mixture was stirred at room temperature for 1 hour. The mixture was filtered (PET filter, 3-5 μm, 205 g/m$^2$) over 30 minutes to obtain 20 kg of wet product. ACN (40 L) was added into a 100 L reactor equipped with an overhead stirrer at room temperature. The 20 kg of wet product was added into the reactor and the reaction mixture heated to reflux and stirred at reflux for 4 hours. The reaction mixture was cooled to room temperature over 3 hours (around 15° C./hour) and filtered to obtain 8.5 kg of wet solid. The wet solid was dried under vacuum (20-30 mmHg) at 50-55° C. for 15 hours to obtain compound 3A as a pale white solid (6.1 kg; 97.4% purity (AUC by HPLC, retention time=3.7 minutes); 83.8% yield). 1H-NMR (400 MHz, DMSO): δ=7.67 (d, 1H), 7.82 (d, 1H), 8.75 (d, 1H), 8.82 (t, 1H), 8.98 (d, 1H), 13.89 (bs, 1H).

Step 3: Synthesis of Compound 6A

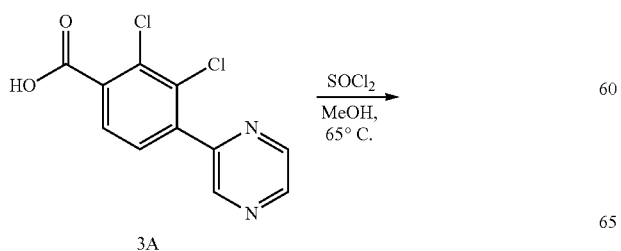

3A

Compound 3A (6.1 kg, 22.7 mol, 1.0 eq.) was added into a 100 L reactor equipped with a temperature probe, overhead stirrer, and condenser. Methanol (92 L) was added into the reactor at room temperature. The mixture was cooled to 0-10° C. and added with SOCl$_2$ (5.4 kg, 45.3 mol, 2.0 eq.) dropwise at 0-10° C. over 30 minutes. The reaction mixture was heated to reflux (65° C.) and stirred at reflux for 15 hours. A suspension was formed. Most of the solvent and SOCl$_2$ was removed under vacuum distillation until about 30 L remained. The mixture was concentrated under vacuum (30-40 mmHg) at 50-55° C. for about 6 hours. Water (10 L) was added to the residual at −5 to 15° C. The pH was adjusted to 8-9 with an aqueous solution of K$_2$CO$_3$ (200 g, dissolved in 2 L of water) at −5 to 15° C. The resulting aqueous layer was extracted twice with isopropyl acetate (25 L, 25 L). The combination of organic layers (about 50 kg) was washed with 20 L of NaHCO$_3$ aqueous layer. The organic layer was separated and washed with 10 L of an aqueous solution of NaHCO$_3$. All the aqueous layers were combined (55.8 kg). The organic layer was filtered through a silica pad (30 cm) and the pad washed with extra isopropyl acetate until the compound 6A was filtered from the silica gel (about 3 hours). The organic layer was concentrated to about 5 L. THF (10 L) was added to the residual and concentrated to about 5 L (3 times) under vacuum (30-40 mmHg) at 50-55° C. for about 3 hours. Another 10 L of THF was added to the residual concentrate, giving a concentrated solution of compound 6A (15.8 kg; 32.83%, 5.19 kg compound 6A in solution; 97.9% purity (AUC by HPLC, retention time=8.5 min); 80.8% yield). 1H-NMR (400 MHz, DMSO): δ=3.98 (s, 3H), 7.54 (d, 1H), 7.78 (d, 1H), 8.63 (d, 1H), 8.72 (t, 1H), 8.94 (d, 1H).

Step 4: Synthesis of Compound 6B

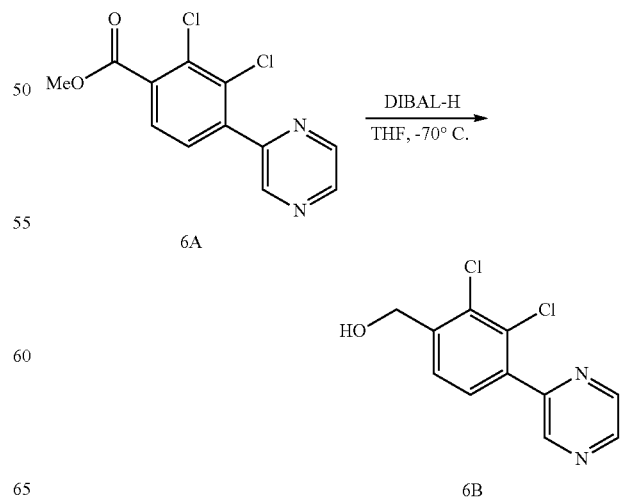

THF (26 L) was added into a 100 L reactor equipped with a temperature probe and overhead stirrer under nitrogen. DIBAL-H (26 kg, 46 mol, 5.0 eq.) was added and the system purged and filled with nitrogen three times. The mixture was cooled to −78 to −70° C. to form solution A. A room temperature solution of compound 6A (2.6 kg, 9.2 mol, 1.0 eq.) in 52 L of THF was added dropwise at −78 to −70° C. over 30 minutes under nitrogen. The mixture was warmed to −30° C. over about 5-6 hours. The reaction mixture was stirred at −40 to −30° C. for 30 minutes. The mixture was slowly added to 42 L of 2N HCL over 1 hour reaching a maximum temperature of 35° C. The mixture was extracted with 26 L of isopropyl acetate. The organic layer was separated and washed with 30 L of brine. This procedure was repeated and both batches of organic layer were combined and concentrated from about 100 L to about 5-10 L under vacuum. A solid slowly formed during concentration. The mixture was cooled to 5-15° C. and stirred for 1 hour. The mixture was filtered (30-50 μm) over 30 minutes. The solid was dried under vacuum at 50° C. for 6 hours to obtain compound 6B as a brown solid (2.1 kg; 97.5% purity (AUC by HPLC, retention time=8.6 min); 45.7% yield). 1H-NMR (400 MHz, DMSO): δ=4.65 (d, 2H), 5.68 (t, 1H), 7.62 (d, 1H), 7.68 (d, 1H), 8.72 (d, 1H), 8.80 (t, 1H), 8.94 (d, 1H).

Step 5: Synthesis of Compound 7

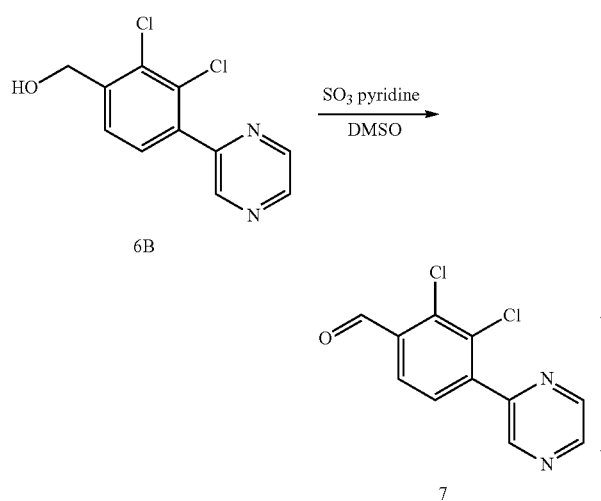

DMSO (10 L) was added to a 50 L flask equipped with a temperature probe and overhead stirrer under nitrogen at room temperature. Compound 6B (2.05 kg, 8.04 mol, 1.0 eq.) was added under nitrogen at room temperature. Et$_3$N (8 L) was added under nitrogen at RT and the mixture was then cooled to 15-20° C. SO$_3$·pyridine (5.1 kg, 32.08 mol, 4.0 eq.) was dissolved into 10 L of DMSO at 5-15° C. in a separate flask and added to the mixture dropwise over 3.5 hours at about 20° C. The reaction mixture was transferred to 70 L of ice-water. The suspension mixture was stirred at 0-10° C. for 1 hour and filtered (PET, 3-5 μm, 205 g/m²) by centrifuge over 1.5 hours to obtain compound 7 as a brown solid. The solid was dissolved in 35 L of DCM at room temperature. The resulting DCM layer was washed with 5 L of brine. The organic layer was separated and concentrated under vacuum at 40-45° C. to dryness to obtain compound 7 as a brown solid (2.33 kg; 96.3% purity (AUC by HPLC, retention time=9.2 minutes); 93.5% yield). 1H-NMR (400 MHz, DMSO): δ=7.67 (d, 1H), 7.99 (d, 1H), 8.67 (d, 1H), 8.75 (s, 1H), 8.99 (d, 1H), 10.56 (s, 1H).

Step 6: Synthesis of Compound 8

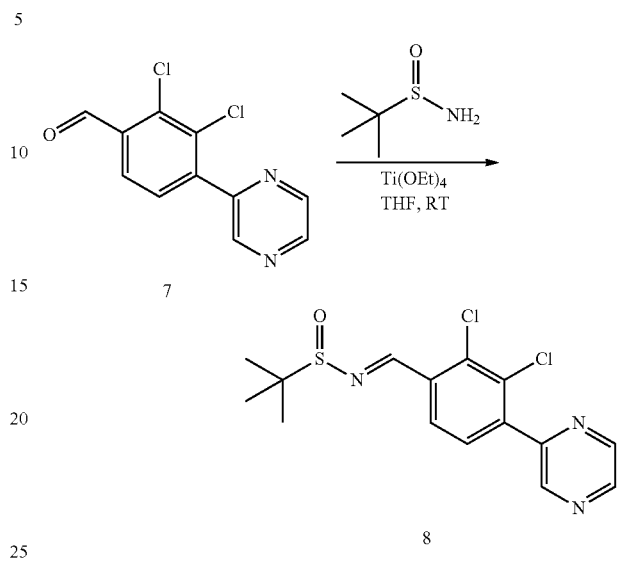

THF (23 L) was added to a 50 L flask equipped with a temperature probe and overhead stirrer under nitrogen at room temperature. Compound 7 (2.3 kg, 9.1 mol, 1.0 eq.) and (S)-2-methylpropane-2-sulfinamide (1.21 kg, 10 mol, 1.1 eq.) were added sequentially to the flask under nitrogen. Ti(OEt)$_4$ (6.22 kg, 27.3 mol, 3.0 eq.) was added dropwise to the flask over 1 hour at 30-35° C. under nitrogen. The system was purged with nitrogen three times and then the mixture was stirred at room temperature for 2 hours. Isopropyl acetate (40 L) was added to the reaction mixture. The entire reaction mixture was then charged to 20 L of brine while stirring slowly at RT. A lot of solid was formed and no heat release was observed. The solid (about 18 kg) was filtered using centrifuge, and then the solid was slurried with 20 L of isopropyl acetate again for 20 minutes, and filtered again, resulting is slightly less solid (17.3 kg). The filtrates were then combined and washed with 20 L of brine. The organic layer was separated and concentrated in a rotavapor under vacuum (30-40 mmHg) at 40-50° C. for about 4 hours to remove the solvents and obtain a brown oil (compound 8). The oil was dissolved in DMF to obtain a black solution (7.36 kg; 40.1%; 3.0 kg compound 8 in solution; 92.1% purity (AUC by HPLC, retention time=9.7 minutes); >100% yield). 1H-NMR (400 MHz, CDCl$_3$): δ=1.30 (s, 9H), 7.59 (d, 1H), 8.11 (d, 1H), 8.64 (s, 1H), 8.73 (m, 1H), 8.97 (s, 1H), 9.10 (s, 1H).

Step 7: Synthesis of Compound 11

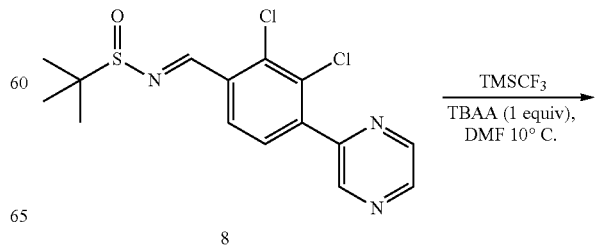

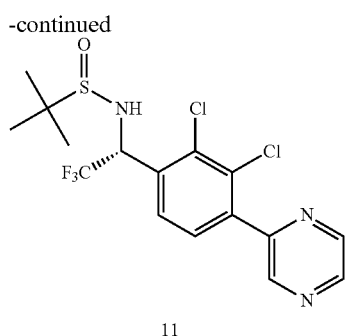

11

DMF (26 L, 10 v/w) was added to a 50 L flask equipped with a temperature probe and overhead stirrer under nitrogen at 15° C. Compound 8 (7.3 kg of DMF solution, containing 2.9 kg, 8.1 mol, 1.0 eq.) and TBAA (2.44 kg, 8.1 mol, 1.0 eq.) were added sequentially to the flask under nitrogen. The mixture was cooled to 0-10° C. TMSCF$_3$ (2.88 kg, 20.3 mol, 2.5 eq.) was then added to the flask over 60 min at 0-10° C. The reaction mixture was stirred at 0-5° C. under nitrogen protection for 3 hours. Isopropyl acetate (60 L) was added to the mixture, followed by the addition of 45 L of NaHCO$_3$ under stirring at 5-25° C. The organic layer was separated, washed three times with NaHCO$_3$ (30 L×3), and concentrated from 60 kg to 2.5 kg of brown oil. The oil product was dissolved in 20 L of TBME and filtered through a pad of silica gel (about 40 cm high, 30 cm diameter) over 2 hours to obtain 2.14 kg of compound 11 in TBME solution. The solution was concentrated at 45-50° C. to dryness to obtain compound 11 as a black oil (1.85 kg; 85.2% purity (AUC by HPLC, retention time=9.1 minutes, 9.6 minutes for diastereoisomer); 53.6% yield). 1H-NMR (400 MHz, CDCl$_3$): δ=1.33 (s, 9H), 3.82-3.85 (d, 1H), 5.61-5.66 (m, 1H), 7.53-7.60 (m, 2H), 8.63-8.64 (d, 1H), 8.71-8.72 (m, 1H), 8.95 (s, 1H).

Step 8: Synthesis of Compound 12 (Free Base)

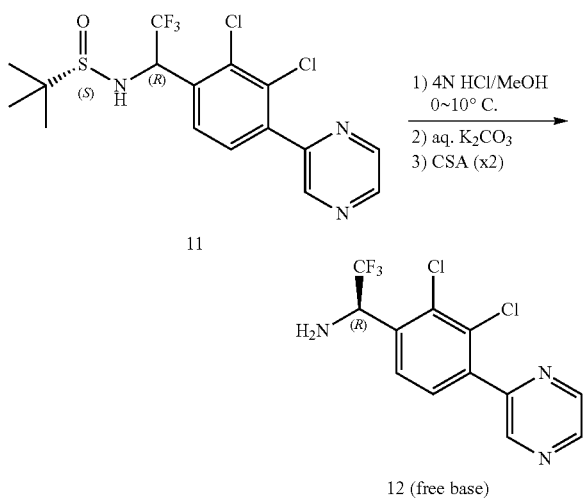

Compound 11 (1.8 kg, 4.23 mol, 1.0 eq., crude) was added to a 50 L reactor equipped with a temperature probe and overhead stirrer under nitrogen at 25° C. Anhydrous MeOH (18 L) was added to dissolve compound 11. Then MeOH/HCl (18 L, 1 N) was added dropwise at 25-30° C. over 10 minutes and the mixture was stirred at 25-30° C. for 1 hour. Water (15 L) was added to the reaction and the mixture concentrated in a rotavapor under vacuum (30-40 mmHg) at 45-50° C. for about 4 hours to remove the solvent. The pH of the mixture was adjusted to 10 with 5 L of K$_2$CO$_3$ solution. 20 L of EtOAc was then added to the mixture and the organic layer was separated and the aqueous layer extracted twice with EtOAc (15 L×2). The organic layers were combined and washed with 10 L of brine. The combined organic layers contained 996 g of compound 12 in 40 kg of EtOAc solution (84% purity (AUC by HPLC, retention time=2.8 minutes). The organic layers were concentrated in a rotavapor under vacuum (30-40 mmHg) at 45-50° C. for about 3 hours to a 7.5 kg volume of compound 12 in EtOAc solution (83% purity (AUC by HPLC, retention time=2.7 minutes).

In a separate 50 L reactor equipped with a temperature probe and overhead stirrer, D-CSA was added (930 g, 4.0 mol, 1.0 eq. to 1.26 kg compound 12) and stirred at room temperature under nitrogen. EtOAc (10 L) and then the EtOAc solution of compound 12 (1.26 kg, 3.9 mol, 1.0 eq.) were each sequentially added to the reactor. The mixture was stirred at room temperature for 1 hour and slowly became a suspension. The mixture was filtered by centrifuge and washed with EtOAc to produce 2.3 kg of compound 12 as an off-white solid (96.0% purity).

The solid product, 20 L of EtOAc, and 10 L of 10% aqueous K$_2$CO$_3$ were added sequentially to a 50 L flask and stirred at room temperature until no solid remained (pH=9-10). The organic layer was separated and the aqueous layer extracted twice with EtOAc (10 L×2). The organic layers were combined (about 32 kg) and washed with 10 L of brine. The organic layer contained 716 g of compound 12 in 31.8 kg of solution.

The organic layer was concentrated under vacuum at 45-50° C. to about 8 L. Activated carbon (200 g) was added to the organic layer and the mixture stirred at 60-70° C. for 1 hour, cooled to room temperature, and filtered using a Buchner funnel and filter paper (pore size: 30-50 μm) over 30 minutes to remove the activated carbon. The mixture was concentrated in a rotavapor under vacuum (30-40 mmHg) at 45-50° C. for about 3 hours to yield 710 g of compound 12 as a yellow solid (99.4% purity).

D-CSA (410 g, 1.77 mol, 1.0 eq. to 680 g compound 12), 3.4 L iPrOH, and 68 mL of water were added sequentially to a 10 L reactor equipped with a temperature probe and overhead stirrer and stirred at room temperature under nitrogen. The mixture was heated to reflux (84° C.) to form solution A after 1 hour. Compound 12 (680 g) was dissolved in 3.4 L of iPrOH and added into solution A for one partition. A clear solution was formed and the temperature decreased to 65° C. The mixture was stirred at 65° C. for about 15 minutes after which a solid appeared. The mixture was cooled to 10° C. over 2 hours, stirred at 10° C. for an additional 30 minutes, and filtered through a Buchner funnel and filter paper (pore size: 30-50 μm) over 30 minutes to collect the 1.1 kg of white solid.

EtOAc (10 L), 1.1 kg of white solid product, and 5 L of 10% K$_2$CO$_3$ were added sequentially to a 20 L flask and mixed for 5 minutes. The solid dissolved (pH=9-10). The EtOAc layer was separated and the aqueous layer extracted twice with EtOAc (5 L each). The organic layers were combined (about 20 L), washed with 5 L of brine, and concentrated in a rotavapor under vacuum (30-40 mmHg) at 45-55° C. for about 3 hours to remove most of the solution and until the residue weight reached 1 kg. Heptanes (1 L) was added to the mixture and stirred at room temperature for 30 minutes. The mixture was filtered using a Buchner funnel and filter paper (pore size: 30-50 μm) over 30 minutes to obtain 419 g of compound 12 base as a white solid (99.7% purity). The filtrate was concentrated to 135 g of compound 12 as a yellow solid (98.7% purity). 1H-NMR (400 MHz, CDCl$_3$): δ=1.85 (bs, 2H), 5.17 (m, 1H), 7.56 (d, 1H), 7.68 (d, 1H), 8.62 (d, 1H), 8.70-8.71 (m, 1H), 8.93 (s, 1H). Combined, the products resulted in a 40.7% yield of compound 12.

Step 9: Synthesis of Compound 10

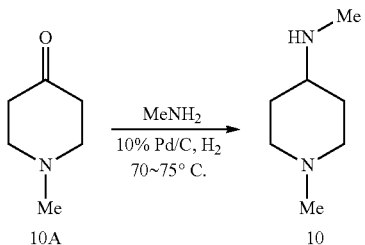 [SMILES: "MeNH2" ; CN1CCC(=O)CC1 ; CNC1CCN(C)CC1]

Pd/C (40 g, 5% w/w) was added into a 10 L autoclave reactor at room temperature under nitrogen. THF (2 L), 2 L of methylamine (27%-30% alcoholic solution, 2.1 eq.), and 800 g of compound 10A (7 mol, 1.0 eq.) were sequentially added into the reactor. The system was purged with hydrogen three times. The mixture was stirred at hydrogen pressure (50 psi) at 70-75° C. overnight and was then filtered using a Buchner funnel and filter paper (pore size: 30-50 μm) over 10 minutes to remove the Pd/C. The filtrate was concentrated in a rotavapor under vacuum (30-40 mmHg) at 45-50° C. for about 3 hours to obtain 933 g of yellow oil. The mixture was distilled without a column at atmospheric pressure and the 140-170° C. portion was collected to obtain 763 g of compound 10 as a colorless oil (98.6% purity (AUC by HPLC, retention time=4.8 minutes); 84.2% yield; 8000 ppm residual ethanol). A portion of the oil (563 g) was distilled using a 3 cm column at atmospheric pressure and the 140-170° C. portion was collected to obtain 510 g of compound 10 (75.8% yield; 134 ppm residual ethanol). 1H-NMR (400 MHz, CDCl$_3$): δ=0.82 (bs, 1H), 1.10-1.12 (q, 2H), 1.66 (d, 2H), 1.73-1.81 (t, 2H), 2.05 (s, 3H), 2.08-2.19 (m, 1H), 2.22 (s, 3H), 2.60 (d, 2H).

Step 10: Synthesis of HM04 Fumarate Salt

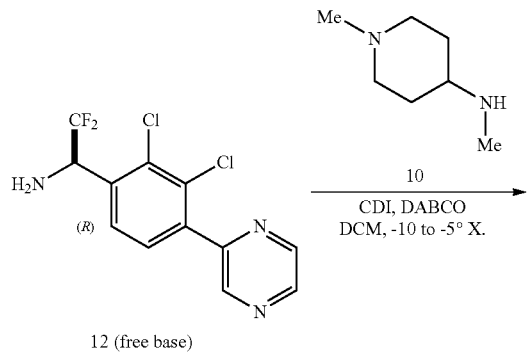

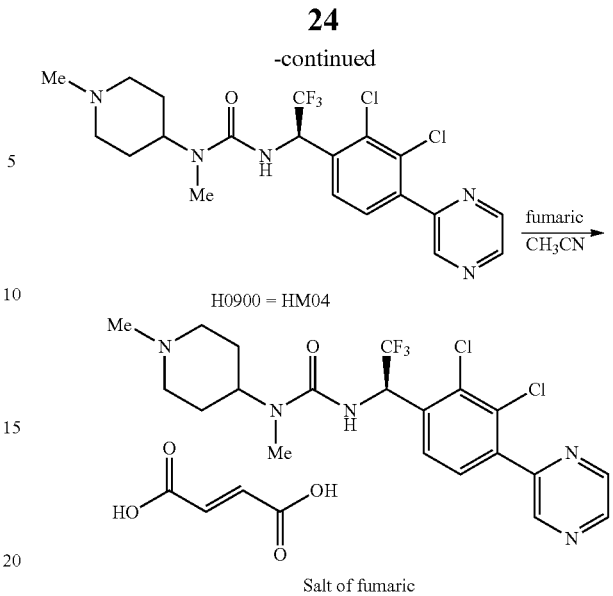

DCM (1 L), 200 g CDI (1.23 mol, 2.0 eq.), and 35 g DABCO (0.31 mol, 0.5 eq.) were sequentially added into a 3 L reactor equipped with a temperature probe and overhead stirrer, and stirred at room temperature under nitrogen. The mixture was cooled to −10 to −5° C. Compound 12 (200 g) was dissolved in 1 L of DCM and added into the mixture dropwise over 1 hour, followed by stirring for 16 hours at −10 to −5° C. Compound 10 (159 g, 1.24 mol, 2.0 eq.) was added at −10 to 0° C. over 10 minutes. The mixture was then warmed to 0 to 5° C. and held for 2 hours. The mixture was concentrated under vacuum at 40-45° C. to about 1 L. HCl (1 L of 1 N) was added to the residual and concentrated in a rotavapor under vacuum (30-40 mmHg) at 45-50° C. for about 2 hours to remove the DCM. Another 3 L of 1N HCl was added to the residual and extracted three times with TBME (4 L, 2 L, 2 L). The aqueous layer was slowly adjusted to pH=9-10 with 20% aqueous K$_2$CO$_3$ (about 1.5 L) and extracted with DCM (2 L×3). The organic layers were combined (about 4 L) and washed three times with 0.25 N KH$_2$PO$_4$ (1.2 L×3). The organic layer was washed with 2 L of brine to bring the pH to neutral and concentrated in a rotavapor under vacuum (30-40 mmHg) at 45-50° C. for about 2 hours to 450 g (335 mL). MTBE (1.5 L) was added to the residual and distilled until 500 mL of liquid was collected. This step was repeated four times with the addition of 500 mL of TBME and collection of 500 mL of distillate, with the exception that 330 mL of liquid was collected at the final distillation. About 1 to 1.2 L of residual remained in the flask. The residual was slowly cooled to room temperature and stirred at room temperature overnight. The mixture was filtered, washed twice with TBME (400 mL×2), and dried to obtain 192 g of HM04 free base a light yellow solid (99.3% purity (AUC by HPLC, retention time=11.0 minutes). The product on the wall was dissolved in DCM and concentrated under vacuum to obtain 22 g of HM04 free base as a brown sticky oil (97.6% purity). The filtrate was concentrated under vacuum to obtain 22.5 g of yellow solid (94.0% purity).

HM04 free base (187 g, 0.39 mol, 1.0 eq., 99.3% purity) and 1.9 L of ACN were sequentially added to a 3 L flask equipped with a temperature probe and overhead stirrer and stirred at 15° C. under nitrogen to obtain a light-yellow suspension. Fumaric acid (45.6 g, 0.39 mol, 1.0 eq.) was added to the flask and generated a white suspension after 1 minute. The reaction suspension was stirred overnight at room temperature, filtered (15-20 µm, ash<0.15), washed twice with ACN (50 mL×2), and dried under vacuum at 50° C. for 6 hours to obtain 207 g of HM04 fumarate salt as a light yellow solid (99.4% purity (AUC by HPLC, retention time=11.1 minutes); 57.8% yield; 3100 ppm residual ACN). The filtrate was concentrated under vacuum to obtain 20.1 g of HM04 fumarate salt as a light yellow solid (97.3% purity).

A portion of the product (117 g) was further dried in a vacuum oven (20-40 mmHg) to lower the residual acetonitrile content. After drying at 60° C. for 6 hours, 15 hours, and 72 hours; and at 65° C. for 18 hours, the residual acetonitrile content was measured as 3100 ppm, 2570 ppm, 1300 ppm, and 256 ppm, respectively. After the drying process, 98 g of HM04 fumarate salt was isolated (99.4% purity (AUC by HPLC, retention time=11.0 minutes); $^1$H-NMR (400 MHz, DMSO): δ=1.49-1.58 (m, 2H), 1.81-1.92 (m, 2H), 2.44-2.53 (m, 5H), 2.78 (s, 3H), 3.12 (m, 2H), 4.06-4.13 (m, 1H), 6.36-6.41 (m, 1H), 6.55 (s, 2H), 7.47 (d, 1H), 7.73 (d, 1H), 8.11 (d, 1H), 8.75 (d, 1H), 8.81-8.82 (m, 1H), 8.99 (d, 1H). The yield of 98 g of HM04 fumarate salt isolated after drying the partial batch was extrapolated over the whole batch to calculate an approximate yield of 48% for step 10.

XRPD analysis of HM04 fumarate salt products obtained after drying at 60° C. for 6 hours, 15 hours, and 72 hours; and at 65° C. for 18 hours was performed (see FIGS. 6-9, respectively). The XRPD profile showed that the HM04 fumarate salt product was consistent with Form 1.

Example 6

Streamlined Synthesis of HM04 Fumarate Salt Form 1

Figure 10:
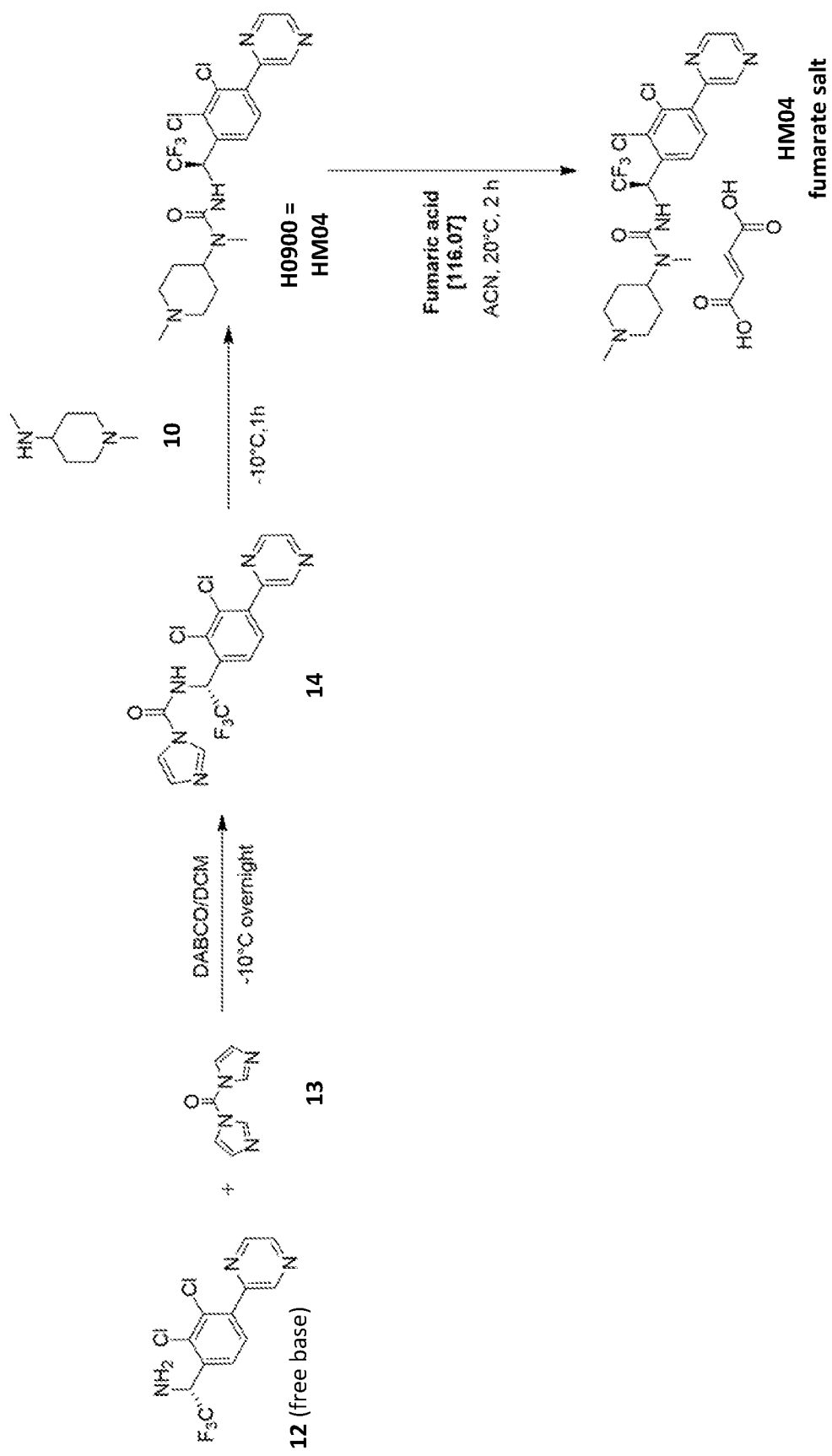
FIG. 10 provides an overview of the streamlined synthesis method of HM04 fumarate salt Form 1 and is described in further detail in Example 6.

The overall yield of HM04 fumarate salt produced using Step 10 of Example 5 was calculated as approximately 48%. In order to increase the overall yield, a streamlined synthesis was investigated that eliminated the step of isolating HM04 free base. In particular, step 10 of the method of Example 5 shown in FIG. 5 was changed. An overview of the streamlined synthesis beginning after step 9 of Example 5 is shown in FIG. 10.

Streamlined HM04 Fumarate Salt Trial 1: DCM (121.4 g), CDI (20.0 g, 123 mmol, 2 eq.) and DABCO (3.5 g, 31 mmol) were sequentially added into an inertized 1 L reactor. The mixture was cooled to −10° C. Separately, a solution of DCM (132.5 g) and compound 12 (20.0 g, 62.1 mmol) were charged into a vessel and stirred until a solution was obtained. This solution was dropped into the 1 L reactor over 33 minutes by keeping the internal temperature at −10 to −5° C. At the end of the addition, the vessel was rinsed with DCM (7.0 g), which was then added to the reaction mixture. After stirring overnight (19 hours) and positive IPC, compound 10 (15.9 g, 124 mmol, 2 eq.) was added over 15 minutes and the vessel rinsed with DCM (9.0 g). After heating at 0° C., 1 hour of stirring, positive IPC, and a further 1.5 hours of stirring, the mixture was heated at room temperature and charged with water (200.1 g). The aqueous layer was separated and the organic layer extracted twice with 1 N HCl (201, 200 g). The combined aqueous layers containing the product were washed with TBME (148 g). After removal of the organic layer, the aqueous layer was charged with DCM (265.0 g) and 50% K$_2$CO$_3$ solution (about 240 ml) until reaching pH 9.61.

Figure 11:
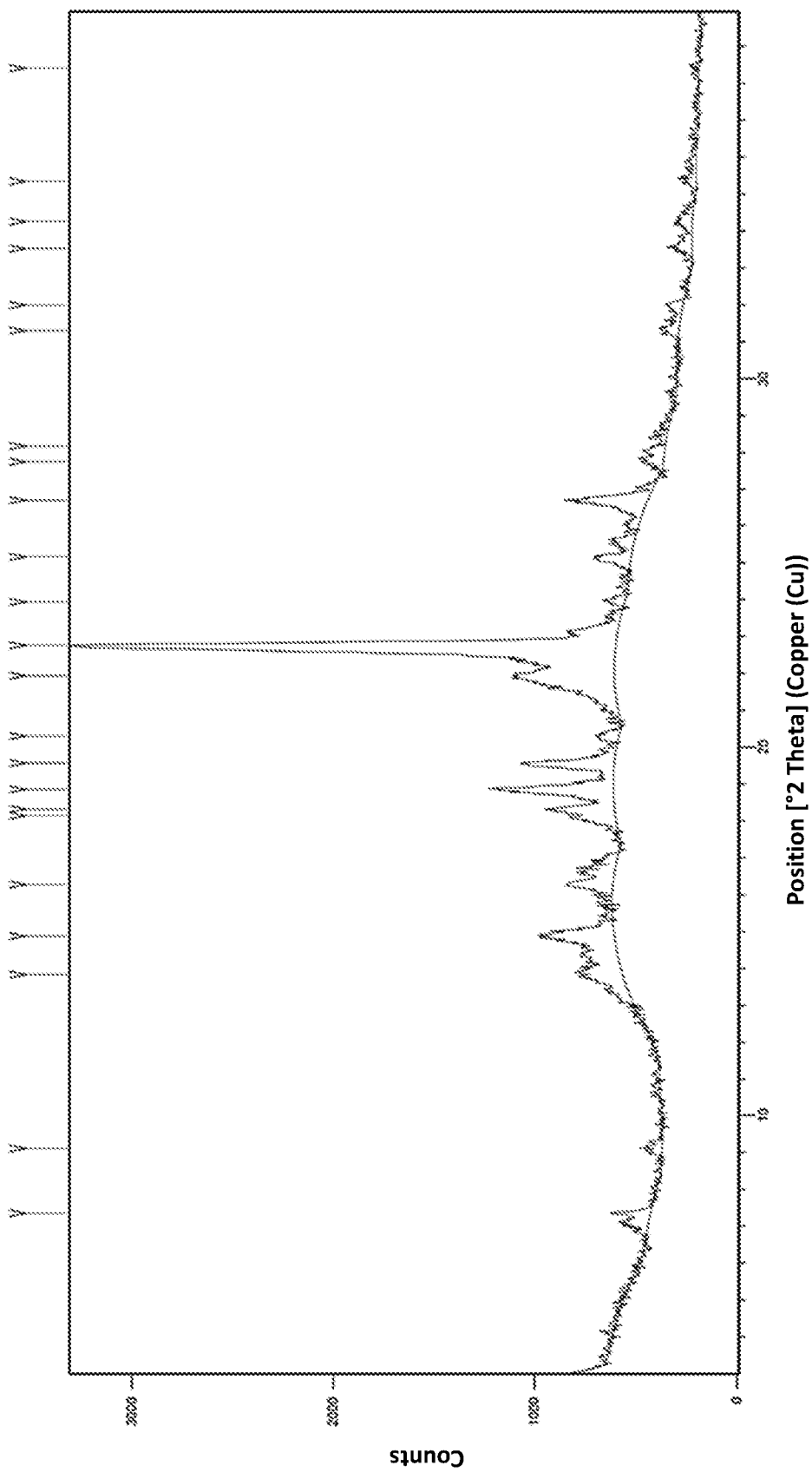
FIG. 11 provides a representative XRPD profile of HM04 fumarate salt crystalline Form 1 prepared as set forth in Example 6, Trial 1.

Meanwhile, a solution of KH$_2$PO$_4$ (8.2 g) in water (240 g) was prepared. The organic layer containing the product was charged with the KH$_2$PO$_4$ solution until reaching pH 7.12 (142.2 g). After separation of the aqueous layer, the organic layer was washed with water (200 g). After separation of the aqueous layer, the organic layer was evaporated at 50° C. ACN (314.4 g) was added and the solvent distilled again at 70-75° C. under vacuum. ACN (235.8 g) was added and the solvent distilled again under vacuum. ACN (141.5 g) was added, the resulting solution polish filtered and the filter washed with ACN (16 g). After heating at 60° C., fumaric acid (7.2 g, 62 mmol) was added to the solution, causing a white precipitate. After cooling to 20° C. over 1 hour, the suspension was filtered and washed twice with TBME (2×30 g). After drying on the filter with nitrogen flow, 70.7 g of wet raw product was obtained. This was slurried with TBME (177.0 g) for 1 hour, filtered, and washed with TBME (70 g). After drying on the filter under nitrogen flow, 33.0 g of wet product was obtained. Heating at 50° C. under vacuum afforded the dry product as a white powder of HM04 fumarate salt (21.1 g; 99.8% purity by HPLC; 57% yield). XRPD analysis confirmed that the product was Form 1 (see FIG. 11).

XRPD analyses described in Examples 6, 7, and 8 were performed using an X'Pert PRO PANalytical diffractometer and the following experimental conditions:

Tube anode: Cu
Tube voltage: 40 kV
Tube current: 40 mA
Wavelength alpha1: 1.5406 Å
Wavelength alpha2: 1.5444 Å
Start angle (2 theta): 3
End angle (2 theta): 40
Counting time: 12,700 seconds
Scan mode: Continuous scan Streamlined HM04 Fumarate Salt Trial 2: The streamlined process described above was further optimized to take advantage of the good crystallization properties of HM04 fumarate salt. In addition to skipping the isolation of the free base and isolating the HM04 fumarate salt product directly after addition of ACN and fumaric acid, in this trial the acid/base extractive workup of the free base was also omitted. The excess fumaric acid was removed with a slurry in TBME.

DCM (120 g), CDI (20.1 g, 124 mmol, 2 eq.) and DABCO (3.5 g, 31 mmol) were sequentially added into an inertized 1 L reactor. The mixture was cooled to −10° C. Separately, a solution of DCM (133.8 g) and compound 12 (20.1 g, 62.4 mmol) were charged into a vessel and stirred until a solution was obtained. This solution was dropped into the 1 L reactor over 39 minutes by keeping the internal temperature at −10 to −5° C. At the end of the addition, the vessel was rinsed with DCM (7 g), which was then added to the reaction mixture. After stirring overnight (18 hours) and positive IPC, compound 10 (15.9 g, 124 mmol, 2 eq.) was added over 15 minutes and the vessel rinsed with DCM (7 g). After heating at 0° C., 1 hour of stirring, and positive IPC, the mixture was charged with water (200 g) and heated at room temperature.

Meanwhile, a solution of KH$_2$PO$_4$ (13.8 g) in water (402 g) was prepared. The aqueous layer was separated and the organic layer containing the product charged with the KH$_2$PO$_4$ solution until reaching pH 7. After separation of the aqueous layer, the organic layer was washed with water (200 g). After separation of the aqueous layer, the organic layer was polish filtered and the filter washed with ACN (64 g). Fumaric acid (7.2 g, 62 mmol) was added to the solution, causing a white precipitate, which was filtered and washed twice with ACN (2×31.5 g). After drying on the filter with nitrogen flow, 44.5 g of wet raw product was obtained. This was slurried with TBME (266.8 g) for 1 hour, filtered, and washed twice with TBME (2×30 g). After drying on the filter under nitrogen flow, 45.0 g of wet product was obtained. Drying at 60° C. under vacuum afforded the dry product as a white powder of HM04 fumarate salt (25.2 g; 99.6% purity by HPLC; 68% yield). XRPD analysis confirmed that the product was Form 1 (see FIG. 12).

Scale-up of HM Fumarate Salt by Method of Trial 2: DCM (418 g), CDI (70.5 g, 435 mmol, 2 eq.) and DABCO (12.4 g, 111 mmol) were sequentially added into an inertized 2 L reactor. The mixture was cooled to −10° C. Separately, a solution of DCM (465 g) and compound 12 (70.0 g, 217 mmol) were charged into a vessel and stirred until a solution was obtained. This solution was dropped into the 2 L reactor over 24 minutes by keeping the internal temperature at −10 to −5° C. At the end of the addition, the vessel was rinsed with DCM (25 g), which was then added to the reaction mixture. After stirring overnight (20 hours) and positive IPC, compound 10 (55.7 g, 434 mmol, 2 eq.) was added over 15 minutes and the vessel rinsed with DCM (24 g). After heating at 0° C., 1.5 hours of stirring, and positive IPC, the mixture was charged with water (700 g) and heated at room temperature.

Figure 13:
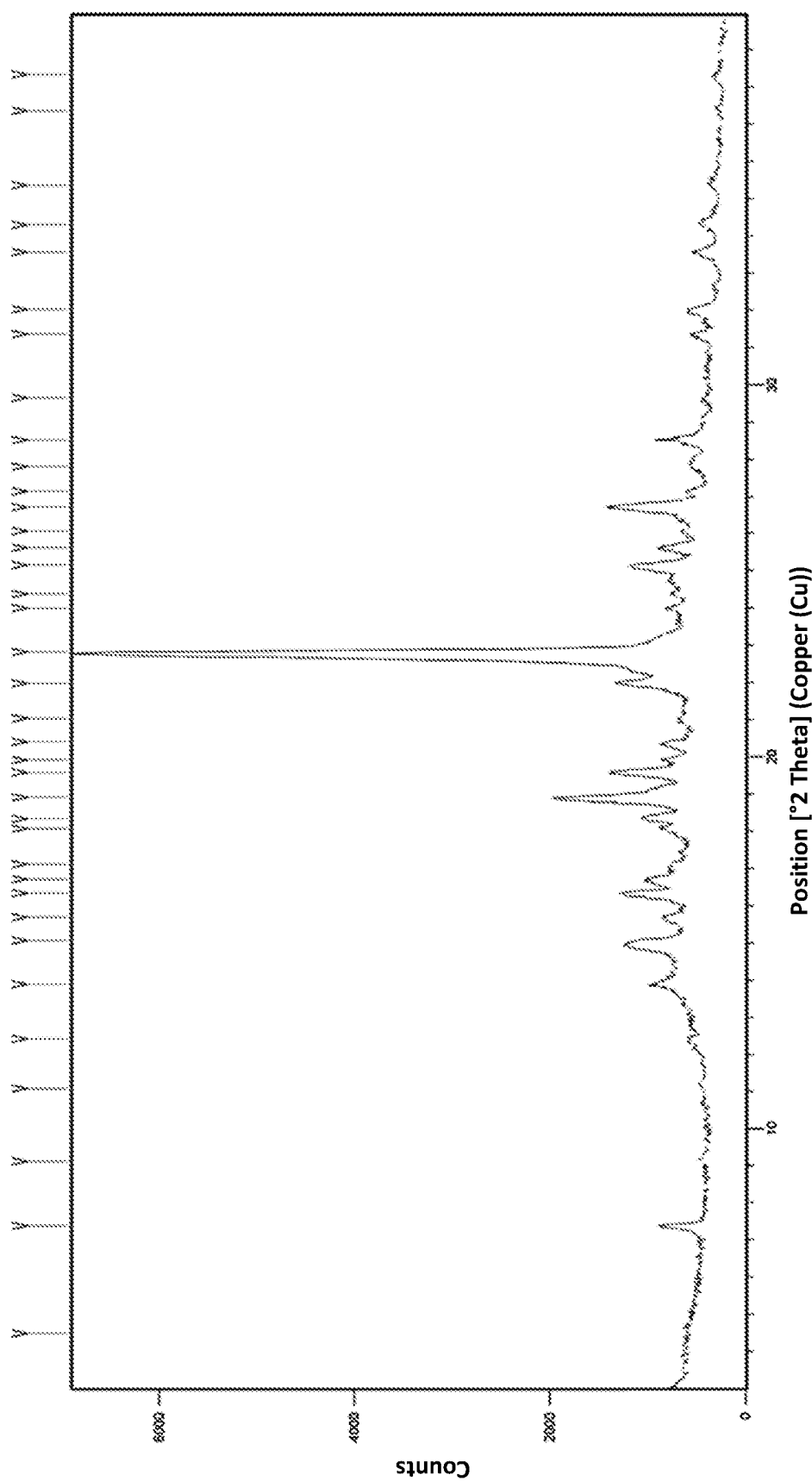
FIG. 13 provides a representative XRPD profile of HM04 fumarate salt crystalline Form 1 prepared as set forth in Example 6, scale up by method of Trial 2.

Meanwhile, a solution of $KH_2PO_4$ (48.3 g) in water (1401 g) was prepared. The aqueous layer was separated and the organic layer containing the product charged with the $KH_2PO_4$ solution until reaching pH 7.03. After separation of the aqueous layer, the organic layer was washed with water (700 g). After separation of the aqueous layer, the organic layer was polish filtered and the filter washed with ACN (220.5 g). Fumaric acid (25.3 g, 218 mmol) was added to the solution, causing a white precipitate, which was filtered and washed with ACN (111 g). After drying on the filter with nitrogen flow, the product was slurried with TBME (933 g) for 80 minutes, filtered, and washed twice with TBME (2×104 g). After drying on the filter under nitrogen flow, 80.8 g of wet product was obtained. Drying at 60° C. under vacuum afforded the dry product as a white powder of HM04 fumarate salt (78.0 g; 99.5% purity by HPLC; 61% yield). XRPD analysis confirmed that the product was Form 1 (see FIG. 13).

Streamlined HM04 Fumarate Salt Trial 3: DCM (120 g), CDI (20.2 g, 125 mmol, 2 eq.) and DABCO (3.5 g, 31 mmol) were sequentially added into an inertized 1 L reactor. The mixture was cooled to −20° C. Separately, a solution of DCM (133 g) and compound 12 (20.0 g, 62.1 mmol) were charged into a vessel and stirred until a solution was obtained. This solution was dropped into the 1 L reactor over 35 min. by keeping the internal temperature at −20 to −15° C. At the end of the addition, the vessel was rinsed with DCM (7.2 g), which was then added to the reaction mixture. After stirring overnight (24 hours) and positive IPC, compound 10 (15.9 g, 124 mmol, 2 eq.) was added over 10 minutes and the vessel rinsed with DCM (7.0 g). After heating at 0° C., 1 hour of stirring, and positive IPC, the mixture was charged with water (200 g) and heated at room temperature.

Figure 14:
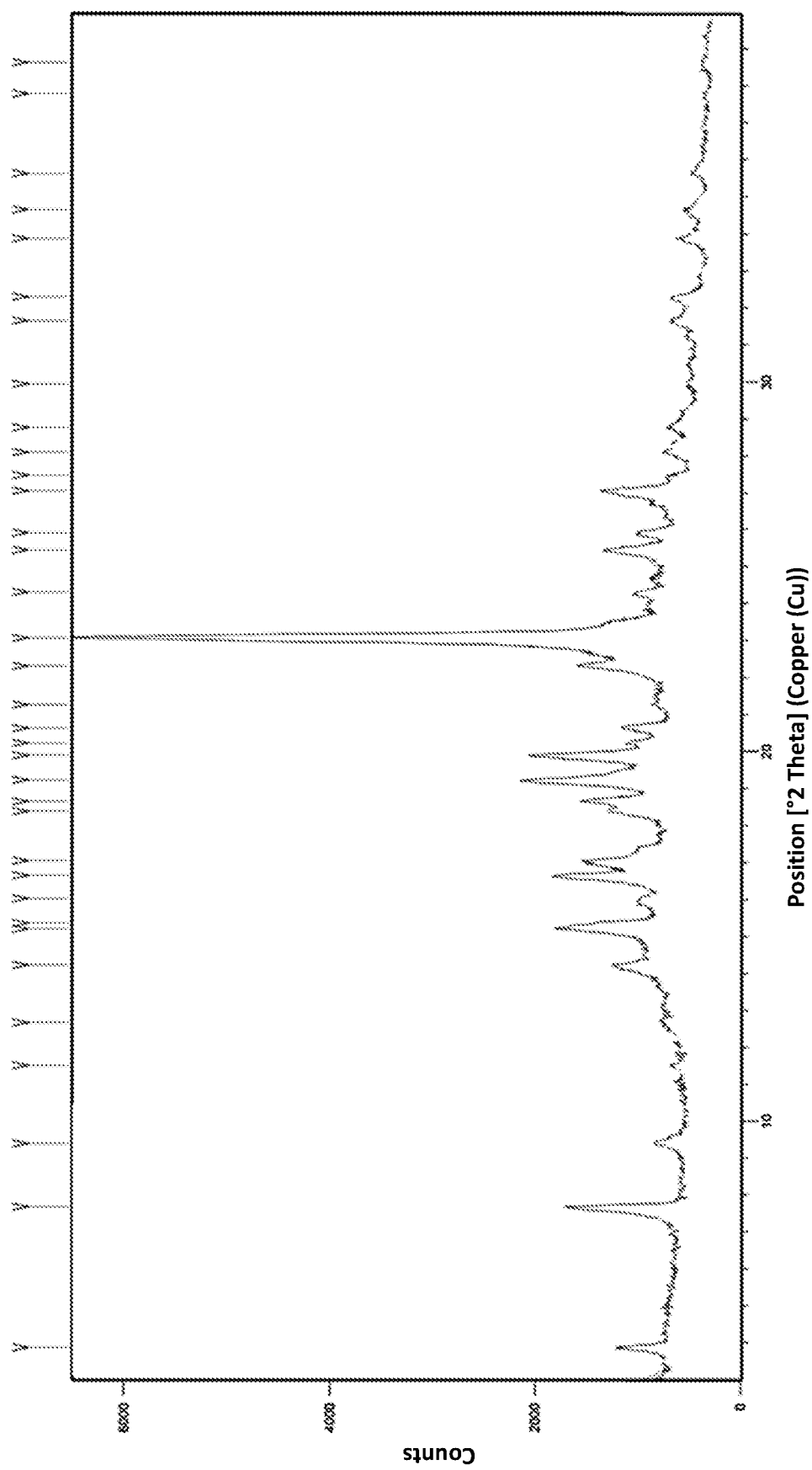
FIG. 14 provides a representative XRPD profile of HM04 fumarate salt crystalline Form 1 prepared as set forth in Example 6, Trial 3.

Meanwhile, a solution of $KH_2PO_4$ (13.7 g) in water (402 g) was prepared. The aqueous layer was separated and the organic layer containing the product charged with the $KH_2PO_4$ (311.1 g) solution until reaching pH 7. After separation of the aqueous layer, the organic layer was washed with water (200 g). After separation of the aqueous layer, the organic layer was polish filtered and the filter washed with ACN (63 g). Fumaric acid (7.2 g, 62 mmol) was added to the solution, causing a white precipitate, which was filtered and washed with ACN (32 g). After drying on the filter with nitrogen flow, 53.7 g of wet raw product were obtained. This was slurried with TBME (267.0 g) for 40 minutes, filtered, and washed twice with TBME (2×30 g). After drying on the filter under nitrogen flow, 41.8 g of wet product was obtained. Drying at 60° C. under vacuum afforded the dry product as a white powder of HM04 fumarate salt (28.1 g; 99.7% purity by HPLC; 76% yield). XRPD analysis confirmed that the product was Form 1 (see FIG. 14).

Example 7

Synthesis of HM04 Fumarate Salt Form 3

HM04 free base (16.0 g 33.6 mmol) was dissolved in ACN (251 g) in an inertized 1 L reactor. After heating at 60° C., fumaric acid (3.9 g, 33.6 mmol) and a rinse with ACN (2.6 g) were added to the solution, causing a white precipitate. After cooling to 20° C. over 2 hours, the product was filtered. After drying on the filter with nitrogen flow, 6.4 g of wet product was obtained. Drying at 60° C. under vacuum afforded the dry product as a white powder of HM04 fumarate salt. A different crystalline form, Form 3, was identified by XRPD analysis (see FIG. 15).

Example 8

Synthesis of HM04 Fumarate Salt Form 4

DCM (120 g), CDI (20.0 g, 123 mmol, 2 eq.) and DABCO (3.5 g, 31 mmol) were sequentially added into an inertized 1 L reactor. The mixture was cooled to −10° C. Separately, a solution of DCM (133 g) and compound 12 (20.0 g, 62.1 mmol) were charged into a vessel and stirred until a solution was obtained. This solution was dropped into the 1 L reactor over 35 minutes by keeping the internal temperature at −10 to −5° C. At the end of the addition, the vessel was rinsed with DCM (7.0 g), which was then added to the reaction mixture. After stirring overnight (18.5 hours) and positive IPC, compound 10 (15.8 g, 123 mmol, 2 eq.) was added over 10 minutes and the vessel rinsed with DCM (6.8 g). After heating at 0° C., 1 hour of stirring, positive IPC, and a further 20 minutes of stirring, the mixture was heated at room temperature and charged with water (200 g). The aqueous layer was separated and the organic layer was extracted twice with 1 N HCl (2×200 g). The combined aqueous layers containing the product were washed with TBME (148 g). After removal of the organic layer, the aqueous layer was charged with DCM (265.0 g) and 50% $K_2CO_3$ solution (about 240 ml) until reaching pH 9.66.

Meanwhile, a solution of $KH_2PO_4$ (8.2 g) in water (240 g) was prepared. The organic layer containing the product was charged with the $KH_2PO_4$ solution (138.2 g) until reaching pH 7.10. After separation of the aqueous layer, the organic layer was washed with water (200 g). After separation of the aqueous layer, the organic layer was evaporated at 40° C. TBME (370 g) was added and distilled again at 65° C. under vacuum until leaving 10 volumes (collected 218.5 g of solvent). Fumaric acid (7.2 g, 62 mmol) was added to the solution, causing a white precipitate. After cooling to 20° C. over 2 hours and 15 hours at this temperature, the suspension was filtered, the mother liquors were recirculated once, and the product was washed with TBME (33 g). After drying on the filter with nitrogen flow, 26.5 g of wet product was obtained. Drying at 50-60° C. under vacuum afforded the dry product as a white powder of HM04 fumarate salt (22.3 g; 99.9% purity by HPLC; 61% yield). A different crystalline form, Form 4, was identified by XRPD analysis (see FIG. 16).

Example 9

Figure 17:
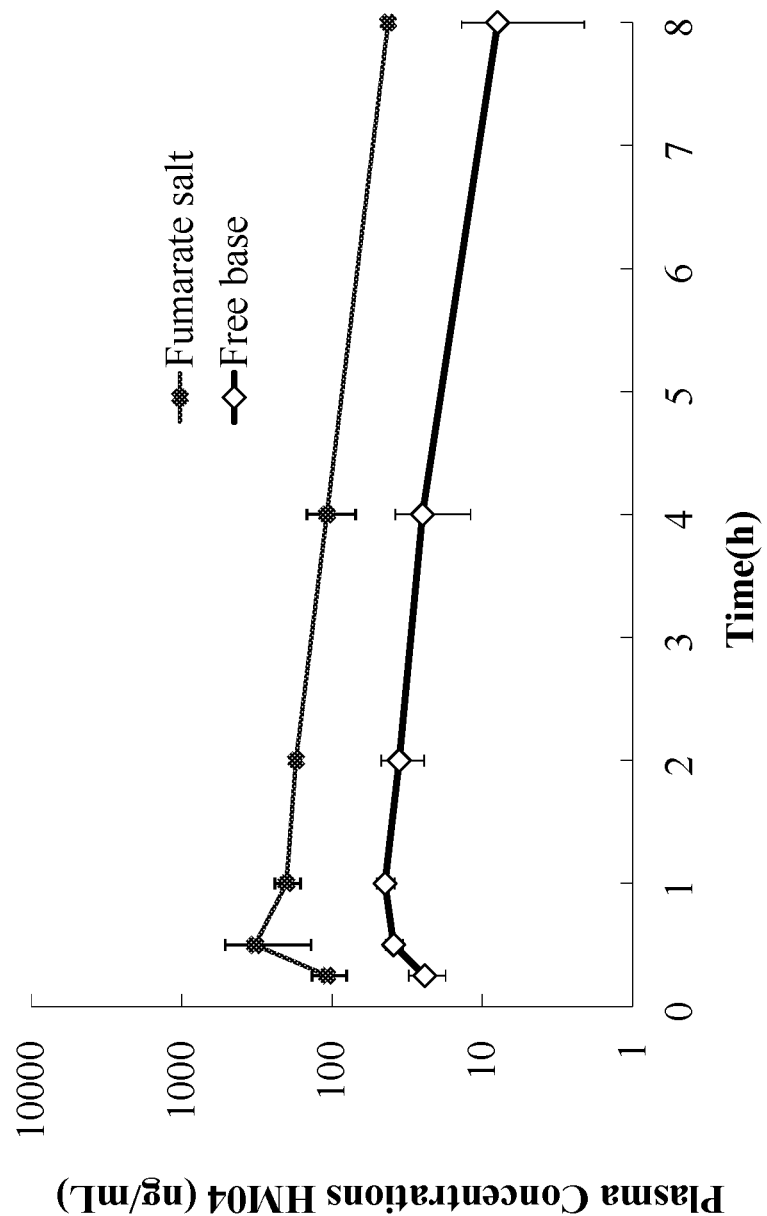
FIG. 17 provides a comparison of the plasma concentration of HM04 (ng/mL) over time in rats dosed orally with 3 mg/kg HM04 free base and 3 mg/kg HM04 fumarate salt (based on the weight of the free base).

Comparison of Pharmacokinetics of Oral Administration of HM04 Free Base and HM04 Fumarate Salt in Rat and Dog The pharmacokinetics of HM04 in plasma of male Sprague Dawley rats dosed with a single oral administration of 3 mg/kg HM04 (based on the weight of the free base) formulated in a solution of 10% DMAC, 6% Solutol, and 84% PBS using either the HM04 free base or HM04 fumarate salt were compared. Blood samples were withdrawn at set time intervals and plasma concentration of HM04 was measured by LC-MS/MS. A comparison of the plasma concentration of HM04 (ng/mL) over time in rats dosed orally with HM04 free base and HM04 fumarate salt is provided in FIG. 17.

A summary of the pharmacokinetic analysis is provided in Table 3, below. Bioavailability at 3 mg/kg HM04 free base was calculated from the ratio of the oral mean AUC to the mean AUC of 990.3±24.6 ng*h/mL determined following intravenous administration of 3 mg/kg HM04 free base to three male Sprague Dawley rats. Bioavailability at 3 mg/kg HM04 fumarate salt (based on the weight of the free base) was calculated from the ratio of the oral mean AUC to the mean AUC of 2103.3±357.7 ng*h/mL determined following intravenous administration of 3 mg/kg HM04 fumarate salt (based on weight of the free base) to three male Sprague Dawley rats.

TABLE 3

Rat Pharmacokinetic Study (3 mg/kg HM04 oral)

| Parameter (mean ± S.D.) | HM04 free base (n = 3) | HM04 fumarate salt (n = 3) |
|---|---|---|
| HM04 plasma concentration (ng/mL) | | |
| 0.08 hours | not tested | not tested |
| 0.25 hours | 24.2 ± 6.6 | 107.8 ± 27.8 |
| 0.50 hours | 39.0 ± 5.2 | 325.9 ± 187.8 |
| 1 hour | 44.4 ± 6.0 | 201.0 ± 38.7 |
| 2 hours | 35.7 ± 11.3 | 173.9 ± 12.2 |
| 4 hours | 25.0 ± 13.0 | 108.3 ± 38.3 |
| 8 hours | 7.9 ± 5.8 | 42.3 ± 2.5 |
| 24 hours | 2.4* | not tested |
| AUC $_{(0-t)}$ (ng * h/mL) | 220.0 ± 57.2 | 970.2 ± 147.0 |
| $T_{max}$ (h) | 1 ± 0 | 0.83 ± 0.29 |
| $C_{max}$ (ng/mL) | 44.4 ± 6.0 | 329.2 ± 184.6 |
| Bioavailability (%)** | 22.2 ± 5.8 | 46.13 ± 6.99 |

*N = 1; The concentration for two of three animals was below the level of quantification.

Figure 18:
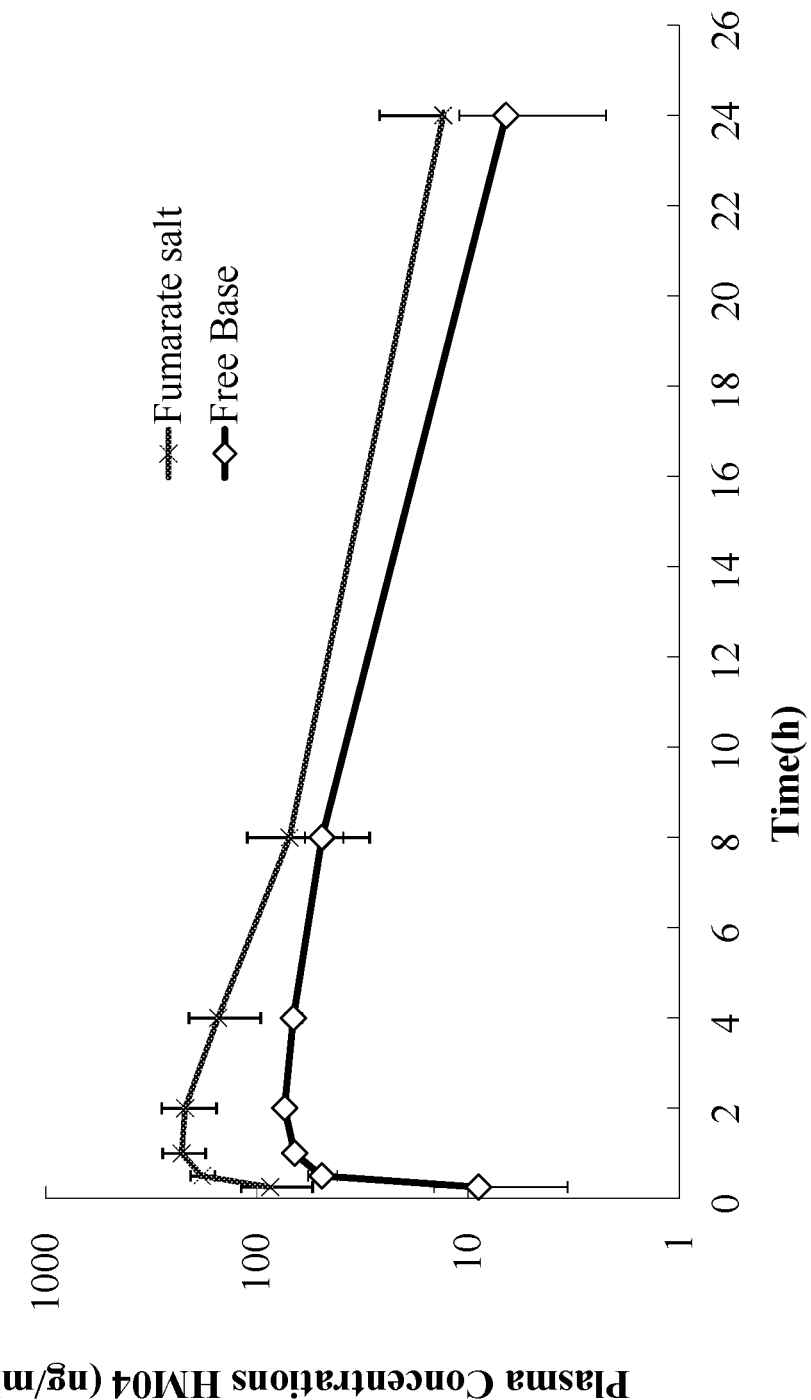
FIG. 18 provides a comparison of the plasma concentration of HM04 (ng/mL) over time in dogs dosed orally with 2 mg/kg HM04 free base and 2 mg/kg HM04 fumarate salt (based on the weight of the free base).

The pharmacokinetics of HM04 in plasma of male Beagle dogs dosed with a single oral administration of 2 mg/kg HM04 formulated in a solution of 10% DMAC, 6% Solutol, and 84% PBS using either the HM04 free base or HM04 fumarate salt were compared. A comparison of the plasma concentration of HM04 (ng/mL) over time in dogs dosed orally with HM04 free base and HM04 fumarate salt is provided in FIG. 18.

A summary of the pharmacokinetic analysis is provided in Table 4, below. Bioavailability was calculated from a dose normalized ratio of the oral mean AUC to the intravenous mean AUC ($AUC_{po}/AUC_{iv} \times Dose_{iv}/Dose_{po}$). Bioavailability at 2 mg/kg HM04 free base was calculated from a dose normalized ratio of the oral mean AUC to the mean AUC of 782.1±363.5 ng*h/mL determined following intravenous administration of 1 mg/kg HM04 free base to three male Beagle dogs. Bioavailability at 2 mg/kg HM04 fumarate salt (based on weight of the free base) was calculated from a dose normalized ratio of the oral mean AUC to the mean AUC of 1126.1±363.6 ng*h/mL determined following intravenous administration of 1 mg/kg HM04 fumarate salt (based on weight of the free base) to three male Beagle dogs.

TABLE 4

Dog Pharmacokinetic Study (2 mg/kg HM04 oral)

| Parameter (mean ± S.D.) | HM04 free base (n = 3) | HM04 fumarate salt (n = 3) |
|---|---|---|
| HM04 plasma concentration (ng/mL) | | |
| 0.08 hours | not tested | not tested |
| 0.25 hours | 8.94 ± 5.56 | 86.6 ± 32.2 |
| 0.50 hours | 49.40 ± 7.72 | 182.4 ± 24.1 |
| 1 hour | 66.33 ± 4.25 | 227.4 ± 52.2 |
| 2 hours | 74.05 ± 3.77 | 219.0 ± 63.6 |
| 4 hours | 67.34 ± 6.27 | 152.9 ± 56.9 |
| 8 hours | 49.23 ± 10.21 | 70.2 ± 41.0 |
| 24 hours | 6.61 ± 4.38 | 13.1 ± 13.2 |
| AUC $_{(0-t)}$ (ng * h/mL) | 928.8 ± 142.5 | 1854.4 ± 828.1 |
| $T_{max}$ (h) | 2 ± 0 | 1.33 ± 0.58 |
| $C_{max}$ (ng/mL) | 74.05 ± 3.77 | 230.47 ± 57.13 |
| Bioavailability (%) | 59.38 ± 9.11 | 82.34 ± 36.77 |

Example 10

Pharmacokinetics of Single Oral Delivery of HM04 Fumarate Salt in Rat and Dog The pharmacokinetics of HM04 in plasma after single oral administration of HM04 fumarate salt to 6-week old male Sprague Dawley rats and male Beagle dogs (1-5 years of age) was investigated. Test formulations of 0.6 mg/mL, 2 mg/mL, and 6 mg/mL HM04 fumarate salt (based on weight of the free base) were prepared in 5% glucose solution. Doses of 3, 10, and 30 mg/kg HM04 fumarate salt (based on weight of the free base) were administered by gastric gavage as a 5 mL/kg dose volume of each of the three test formulations. Four animals were in each dose group. The formulation was administered to the dogs in fasting conditions with food provided three hours post-dosing.

Figure 19:
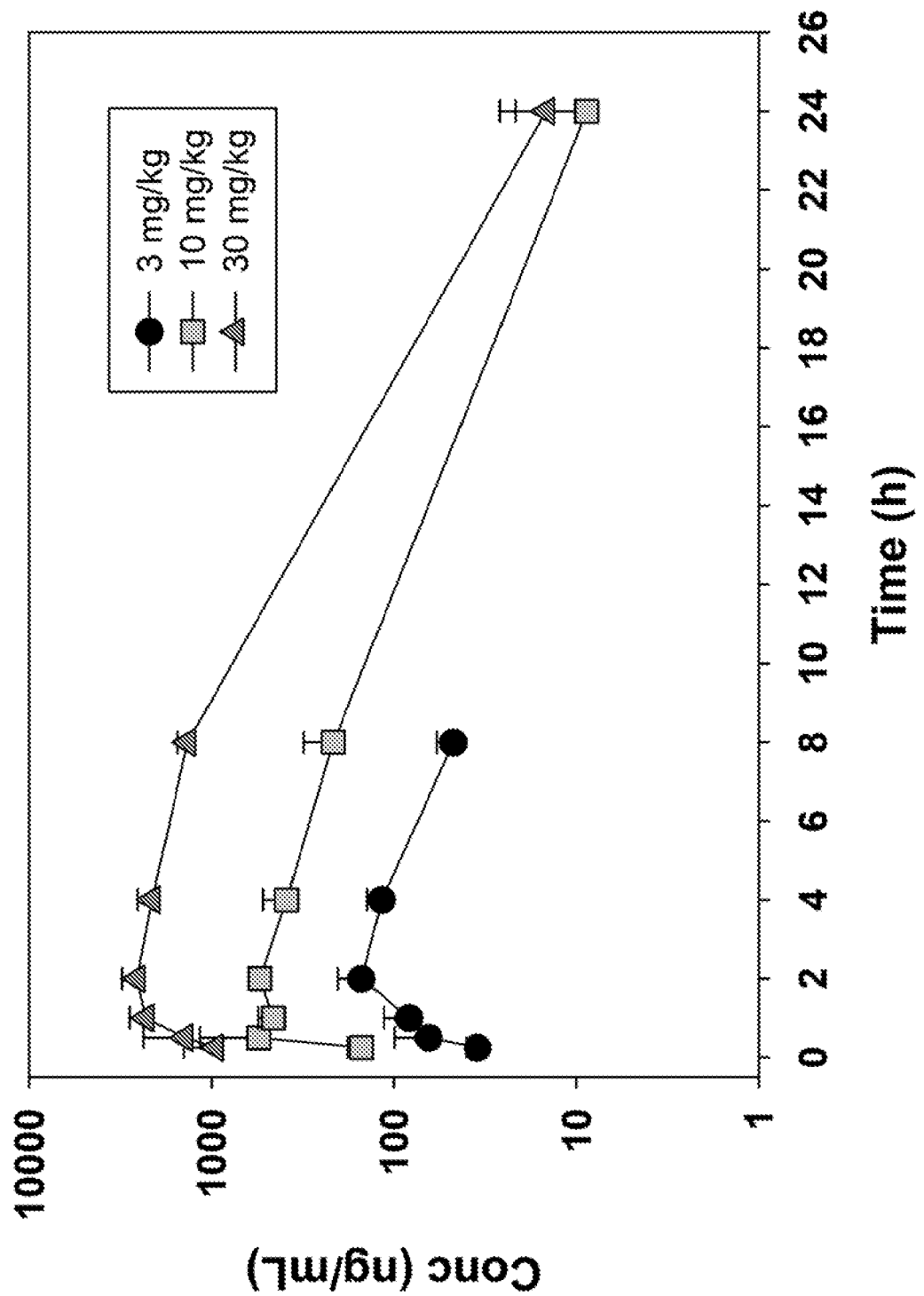
FIG. 19 provides comparison of the plasma concentration of HM04 (ng/mL) in rats over time after being dosed orally with 3, 10, and 30 mg/kg HM04 fumarate salt (based on the weight of the free base).

A comparison of the plasma concentration of HM04 (ng/mL) in rats over time is provided in FIG. 19 and a summary of the pharmacokinetic analysis is provided in Table 5, below. Bioavailability at 3 mg/kg was calculated from the ratio of the oral mean AUC to the mean AUC of 1760±196 ng*h/mL determined following intravenous administration of 3 mg/kg HM04 fumarate salt (based on weight of the free base) to four male Sprague Dawley rats. intravenous 3 mg/kg mean AUC (n=4). Bioavailability at 10 mg/kg was calculated from the ratio of the oral mean AUC to the mean AUC of 6170±1770 ng*h/mL determined following intravenous administration of 10 mg/kg HM04 fumarate salt (based on weight of the free base) to four male Sprague Dawley rats. The standard deviation associated with the mean oral bioavailability was calculated according to the formula:

$$SDq = [^2\sqrt{(my^2 \cdot SDx^2 + mx^2 \cdot SDy^2)}]/my^2$$

where q=mean bioavailability; mx=oral dose-normalized mean AUC, and my=IV dose-normalized mean AUC.

TABLE 5

Rat Pharmacokinetic Study

| Parameter (mean ± S.D.) | 3 mg/kg (n = 4) | 10 mg/kg (n = 4) | 30 mg/kg (n = 4) |
|---|---|---|---|
| HM04 plasma concentration (ng/mL) | | | |
| 0.25 hours | 34.7 ± 5.42 | 150 ± 28.5 | 950 ± 465 |
| 0.50 hours | 64.2 ± 35.0 | 548 ± 603 | 1400 ± 961 |
| 1 hour | 82.4 ± 30.8 | 456 ± 100 | 2290 ± 537 |
| 2 hours | 150 ± 53.5 | 652 ± 62.1 | 2560 ± 530 |
| 4 hours | 116 ± 24.0 | 387 ± 134 | 2120 ± 422 |
| 8 hours | 47.0 ± 10.9 | 215 ± 97.3 | 1350 ± 179 |
| 24 hours | BLQ | 8.73 ± 17.5* | 14.6 ± 6.8 |
| AUC $_{(0-last)}$ (ng * h/mL) | 762 ± 164 | 3360 ± 685§ | 26200 ± 3970 |
| $T_{max}$ (h) | 3.00 ± 1.15 | 1.38 ± 0.750 | 1.75 ± 0.500 |
| $t_{1/2}$ (h) | 2.82 ± 0.354⁺ | 4.88 ± 2.07§ | 2.65 ± 0.193 |
| $C_{max}$ (ng/mL) | 156 ± 47.3 | 769 ± 458 | 2590 ± 524 |
| Bioavailability (%) | 43.3 ± 10.5 | 54.4 ± 15.2 | | last = time at which the last detectable concentration was measured
BLQ = below the limit of quantification.
*N = 1; The concentration for three of four animals was below the level of quantification.
⁺N = 2; §N = 3.

The exposure to HM04 increased with the dose with a more than a proportional increase at 30 mg/kg. After single oral administration of 3, 10, and 30 mg/kg to rats, HM04 attained its Cmax within 4 hours. After oral dosing, the compound was absorbed with a bioavailability of about 40-50% at the doses of 3 and 10 mg/kg.

Figure 20:
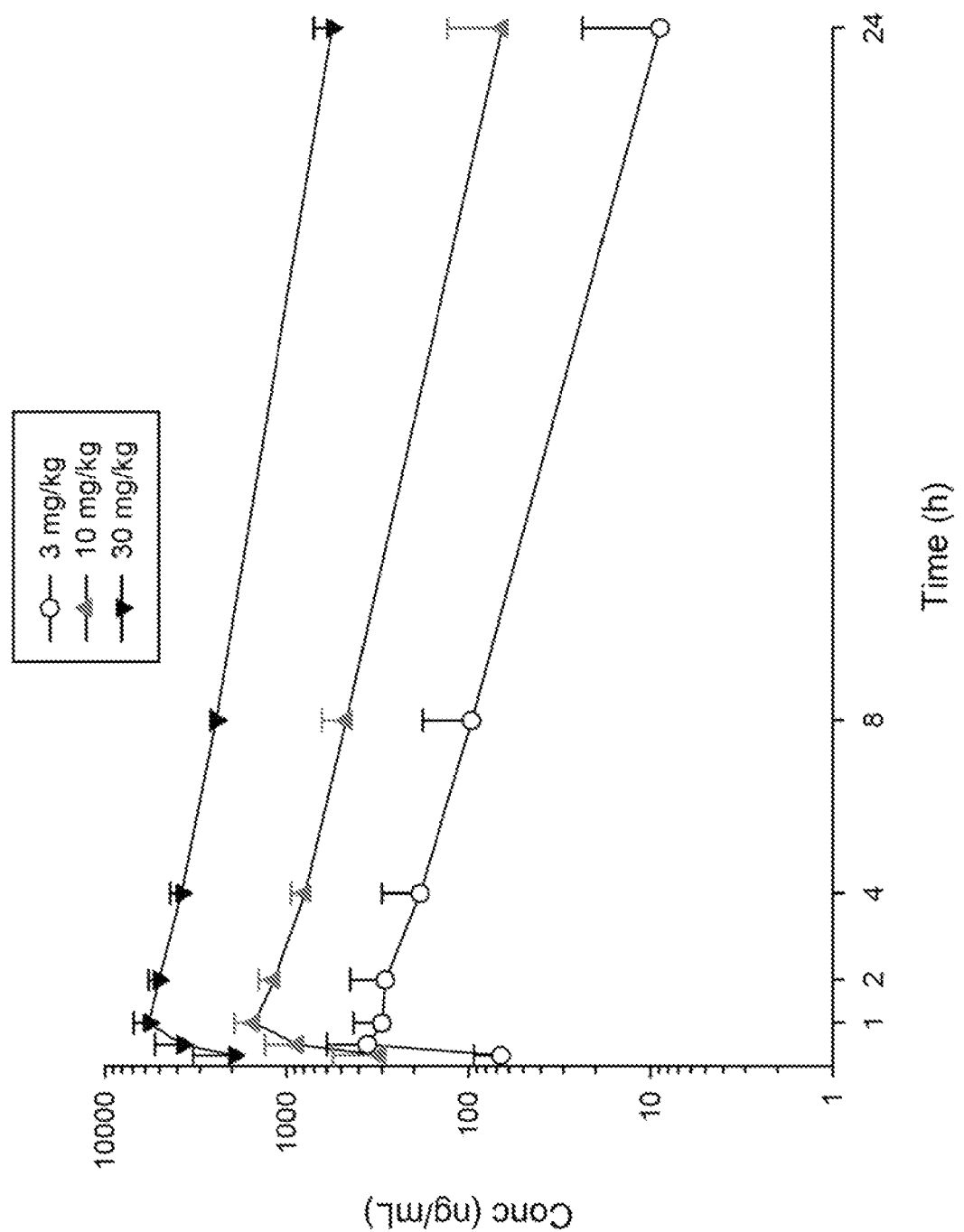
FIG. 20 provides comparison of the plasma concentration of HM04 (ng/mL) in dogs over time after being dosed orally with 3, 10, and 30 mg/kg HM04 fumarate salt (based on the weight of the free base).

A comparison of the plasma concentration of HM04 (ng/mL) in dogs over time is provided in FIG. 20 and a summary of the pharmacokinetic analysis is provided in Table 6, below.

TABLE 6

Dog Pharmacokinetic Study

| Parameter (mean ± S.D.) | 3 mg/kg (n = 4) | 10 mg/kg (n = 4) | 30 mg/kg (n = 4) |
|---|---|---|---|
| HM04 plasma concentration (ng/mL) | | | |
| 0 hours* | 5.34 ± 3.83 | 2.15 ± 4.30 | BLQ |
| 0.25 hours | 66.0 ± 26.8 | 307 ± 246 | 1940 ± 1330 |
| 0.50 hours | 360 ± 238 | 862 ± 460 | 3730 ± 1560 |
| 1 hour | 300 ± 127 | 1510 ± 435 | 5720 ± 1200 |
| 2 hours | 287 ± 158** | 1170 ± 260 | 5030 ± 710 |
| 4 hours | 185 ± 115 | 789 ± 150 | 3780 ± 577 |
| 8 hours | 95.6 ± 83.3 | 468 ± 171 | 2440 ± 176 |
| 24 hours | 8.83 ± 14.7 | 65.1 ± 65.2 | 560 ± 147 |
| AUC $_{(0-last)}$ (ng * h/mL) | 2160 ± 1720 | 10900 ± 3500 | 54000 ± 6010 |
| $T_{max}$ (h) | 0.875 ± 0.250 | 1 ± 0 | 1 ± 0 |

TABLE 6-continued

Dog Pharmacokinetic Study

| Parameter (mean ± S.D.) | 3 mg/kg (n = 4) | 10 mg/kg (n = 4) | 30 mg/kg (n = 4) |
|---|---|---|---|
| $C_{max}$ (ng/mL) | 425 ± 222 | 1510 ± 435 | 5720 ± 1200 |
| $t_{1/2}$ (h) | 4.02 ± 1.21 | 4.93 ± 1.31 | 6.97 ± 0.613 |
| Bioavailability (%) | 55.6 ± 18.8 | 68.0 ± 10.0 | |

BLQ = below the limit of quantification.
*Pre-dose concentration was determined. Dosing was performed at least 4 days apart in the same animals.
**N = 3; Dog 3 excluded from statistics as outlier.

At 3 mg/kg, three of the four pre-dose concentrations of HM04 were detectable (range 5.15-8.31 ng/mL). The samples were reanalyzed in duplicate and confirmed positive. In addition, at oral 10 mg/kg, Dog 2 showed a detectable pre-dose concentration (8.60 ng/mL). It is unlikely that this concentration is a residual concentration from the previous 3 mg/kg dose because that concentration was below the limit of quantification at 24 hours. These values, close to the lower limit of quantification of the analytical method (2.5 ng/mL), were excluded from the calculations replaced by the zero value.

For single oral administrations of HM04 fumarate salt, maximal concentrations of HM04 were rapidly achieved within 1 hour post-dosing. Detectable concentrations of the compound were measured up to 24 hours post dosing in all but two dogs. After the achievement of the maximal concentration, HM04 plasma levels declined with apparent terminal half-life (range 4-7 hours) similar to the half-life after intravenous administration (range 4-5 hours). In the oral dose range of 3 to 30 mg/kg, while Cmax increased roughly proportionally with the dose, AUC increased more than in direct proportion with the dose. The oral bioavailability of HM04 was high in agreement with the low clearance of the compound.

Oral absolute bioavailability at 3 mg/kg was calculated from the ratio of individual oral $AUC_\infty$ to the individual $AUC_\infty$ values determined following intravenous administration of 3 mg/kg HM04 fumarate salt (based on weight of the free base) to the same four male Beagle dogs. The following individual oral and IV $AUC_\infty$ values were determined: Dog 1: 4930 and 6190 ng*h/mL, respectively; Dog 2: 1440 and 3100 ng*h/mL, respectively; Dog 3: 1160 and 3210 ng*h/mL, respectively; and Dog 4: 1850 and 3070 ng*h/mL, respectively.

Oral absolute bioavailability at 10 mg/kg was calculated from the ratio of individual oral $AUC_\infty$ to the individual $AUC_\infty$ values determined following intravenous administration of 10 mg/kg HM04 fumarate salt (based on weight of the free base) to the same four male Beagle dogs. The following individual oral and IV $AUC_\infty$ values were determined: Dog 1: 17500 and 22500 ng*h/mL, respectively; Dog 2: 8780 and 13200 ng*h/mL, respectively; Dog 3: 8470 and 15500 ng*h/mL, respectively; and Dog 4: 10900 and 14900 ng*h/mL, respectively.

Plasma HM04 concentrations were measured by LC-MS/MS following protein precipitation in the 96-well plate format. At the time of analysis samples were thawed out at ambient temperature. Aliquots of 25 µL of rat or dog $K_3$EDTA plasma were spiked with 300 µL of internal standard (25 ng/mL of HM04-d8 in acetonitrile). After gentle vortex mixing for 5 minutes and centrifugation at 2010 g for 15 minutes at 4° C., an aliquot of 100 µL of the organic phase was transferred into a fresh 96-well polypropylene plate, using a P3-Evolution robotic system (Perkin Elmer). Following dilution with 100 µL of 10 nM ammonium formate pH 3.5, an aliquot of 10 µL was injected into the LC-MS/MS system. The LC-MS/MS conditions are provided in Table 7, below.

TABLE 7

| HPLC system: | Hewlett Packard 1100 series | | | | | |
|---|---|---|---|---|---|---|
| Mobile phase: | Channel A: 10 mM ammonium formate pH 3.5 | | | | | |
| | Channel B: Acetonitrile | | | | | |
| Elution mode: | Gradient | | | | | |
| Time (min) | 0.0 | 1.0 | 1.1 | 2.5 | 2.6 | 4.0 |
| % A | 75 | 75 | 10 | 10 | 75 | 75 |
| % B | 25 | 25 | 90 | 90 | 25 | 25 |
| Total Run Time: | 4.0 minutes | | | | | |
| Flow rate: | 0.3 mL/min | | | | | |
| Approximate retention times: | 2.18 min | | | | | |
| Column oven temp. | 40° C. | | | | | |
| Analytical column: | Zorbax SB-C18 (2.1 × 50 mm, 3.5 µm) | | | | | |
| Autosampler type: | CTC Analytics CTC PAL | | | | | |
| Injection volume: | 10 µL | | | | | |
| Autosampler temperature: | 4° C. | | | | | |
| MS instrument: | Applied Biosystem SCIEX API 3000 | | | | | |
| Ionisation: | Turbo Ion Spray in positive ion mode | | | | | |
| MR71 transition: HM04 | m/z | 476.08 | | >m/z | | 129.19 |
| MRM transition: HM04-d8 | m/z | 484.24 | | >m/z | | 137.41 |
| Resolution: | Q1 Unit | | | | | |
| | Q3 Unit | | | | | |
| Lower Limit of Quantification: | 5.0 ng/mL (rat); 2.5 ng/mL (dog) | | | | | |
| Upper Limit of Quantification: | 5000 ng/mL (rat); 1250 ng/mL (dog) | | | | | |
| Software used: | Analyst 1.4.1 and Watson 7.4 | | | | | |

Example 11

Antagonist Activity of HM04 with the Ghrelin Receptor (GHSR1a)

The binding properties of HM04 to the ghrelin receptor GHSR1a was studied using HM04 fumarate salt in a fluorescence imaging plate reader (FLIPR) assay in duplicate. HM04 showed significant antagonist activity on GHSR1a with an IC50 value of 7.308 nM. (FIG. 21A). Comparative testing was also done with the reference GHSR1a antagonist R011 (WO2005/048916, example 30). R011 showed antagonist activity on GHSR1a with an IC50 value of 343 nM (FIG. 21B).

Figure 21E:
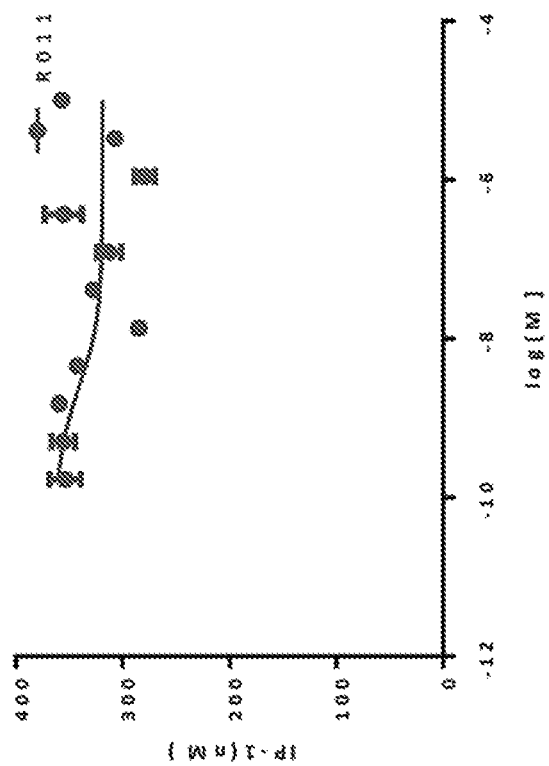
FIG. 21E shows the concentration-response curve of HM04 in an inositol 1 phosphate (IP-1) inverse agonist assay.
Figure 21F:
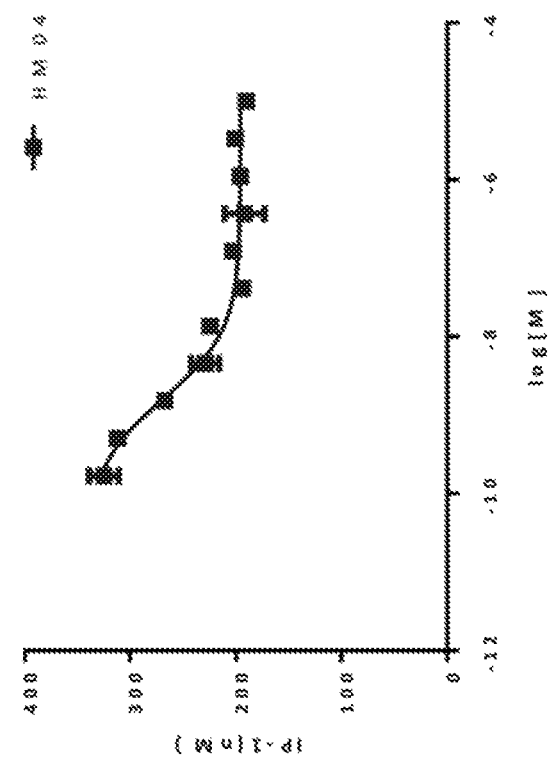
FIG. 21F shows the concentration-response curve of R011 in an inositol 1 phosphate (IP-1) inverse agonist assay.

No agonist activity was observed with HM04 and R011 at concentrations up to 10 µM (FIGS. 21C and 21D). Both HM04 and R011 did not show a clear significant inverse agonist activity (FIGS. 21E and 21F) in an Inositol 1 phosphate (IP-1) inverse agonist activity study. The in vitro data suggest that HM04 is a potent ghrelin antagonist without agonist or a clear inverse agonist activity.

The compounds were diluted with 100% DMSO to make 30 mM stock. On the test day, serial dilutions were prepared starting from the stock solution. For the FLIPR assay: 1) 8 µl of DMSO was added to 2 µl of compound stock solution (30 mM) to produce 10 µl of 6 mM solution; half-fold serial dilutions of the 6 mM solution were produced to generate ten doses; 2) test solutions were obtained by diluting the stock solutions 1/40 in assay buffer (DMSO concentration 2.5%). For the IP-1 assay: 1) 29 µl of DMSO was added to 1 µl of compound stock solution (30 mM) to produce 30 µl of 1 mM solution; half-fold serial dilutions of the 1 mM solution were produced to generate 10 doses; 2) test solutions were obtained by diluting the stock solutions 1/100 in assay buffer (DMSO final concentration 1%).

For the agonist and antagonist activity study, HEK293 cells stably expressing human GHSR1a receptor were used in a (FLIPR) assay. Once day prior to the test, cells were seeded at a density of $1.5 \times 10^4$ cells/well in a Matrigel® coated 384-well plate with 30 µl of complete DMEM medium, and incubated at 37° C. in 5% $CO_2$ for 22-26 hours. On the test day, 4× loading dye was added into each well (10 µl per well for 384 well plates). Assay plates were incubated at 37° C. in the dark for 30 minutes. The dye content was removed by centrifugation at 300 rpm for 30 seconds. HBSS/Hepes (30 µl) with 1 mM probenecid was added with PlateMate Matrix (low speed setting, Thermo Fisher Scientific). The plate was then placed in FLIPR Tetra (Molecular Devices) and 10 µl of 4× working concentrations of HM04 or R011 were added by FLIPR (agonist mode). Fluorescence signal was detected with FLIPR at room temperature according to standard settings for 10 minutes before cells were exposed to 10 µl of 5× working concentrations of agonists (compound added by FLIPR). The fluorescence signal was detected in the subsequent 3 minutes (antagonist mode).

For the inverse agonist activity study, the same procedure described above was followed up to the day of the test. On the test day, the medium was removed by centrifuging at 700 rpm for 30 seconds and 20 µl/well of assay buffer containing the HM04 or R011 was added. The assay plates were incubated at 37° C. in the dark for 1 hour. IP1-d2 (5 µl) and AB-Cryp (5 µl) were sequentially added to all wells using multidrop Combi. The plate was incubated at room temperature for 1 hour and read on EnVision at 620 nm and 665 nm.

Data were reported as relative light units (RLUs) and analyzed using GraphPad Software Inc. version 6. The half maximal inhibitory concentration (IC50) measured for HM04 and R011 were calculated by non-linear regression analysis.

Example 12

Effect of HM04 Fumarate Salt on Ghrelin-Induced Increase of Growth Hormone in Rats Rats were divided into four groups: 1) 1 ml/kg saline plus 10 ml/kg 0.5% CMC p.o. (n=6); 2) 15 µg/kg ghrelin i.v. plus 10 ml/kg 0.5% CMC p.o. (n=6); 3) 30 mg/kg HM04 fumarate salt p.o. 2 hours before 15 µg/kg ghrelin i.v. (n=6); 4) 10 mg/kg ghrelin antagonist R011 i.p. 30 minutes before 15 µg/kg ghrelin i.v. (n=6). Blood was collected as 100 µl samples at time 0 and at 15 minutes after ghrelin injection. Rats were anesthetized with 64.8 mg/kg sodium pentobarbital. A catheter filled with heparinized saline solution was inserted in the left femoral artery for blood collection and fitted with an extension tube, 1-mL sampling syringe, and a 3-way cock to allow excess blood to return.

Plasma levels of growth hormone (GH) were determined using Rat GH ELISA (Millipore, Catalog No. EZRMGH-45K). Measurements were performed in duplicate. GH AUC 0-15 min was calculated using the trapezoidal method. One-way and two-way ANOVA test was used to compare differences between groups. All values are presented as mean±SEM. One-way ANOVA was performed followed by Turkey's post hoc test where significance was indicated by p values<0.05 or p values<0.01.

Figure 22:
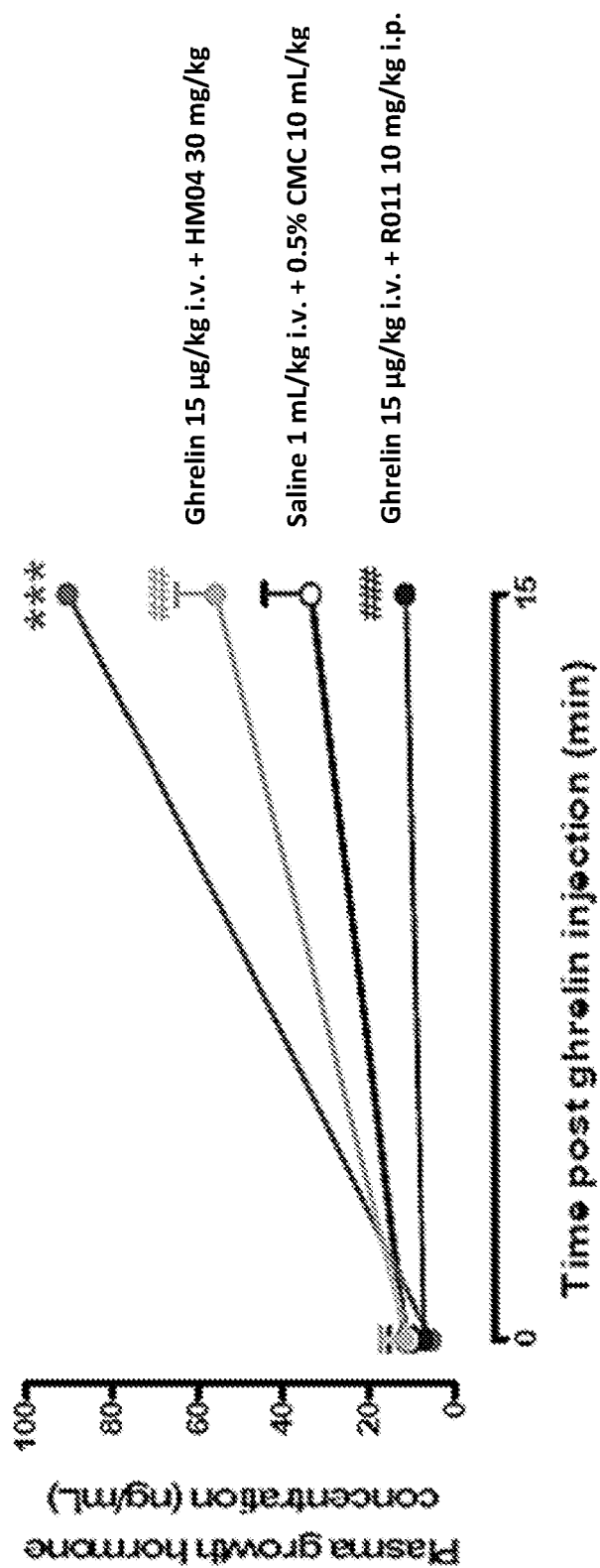
FIG. 22 shows the mean plasma growth hormone concentration observed in rats at time 0 and 15 minutes following ghrelin injection in the following four treatment groups: 1) 1 ml/kg saline plus 10 ml/kg 0.5% CMC p.o. (n=6); 2) 15 µg/kg ghrelin i.v. plus 10 ml/kg 0.5% CMC p.o. (n=6); 3) 30 mg/kg HM04 fumarate salt p.o. 2 hours before 15 µg/kg ghrelin i.v. (n=6); 4) 10 mg/kg ghrelin antagonist R011 i.p. 30 minutes before 15 µg/kg ghrelin i.v. (n=6).

The injection of saline resulted in a slight increase of plasma GH. Ghrelin itself induced a robust increase of GH after 15 minutes from the injection. The mean plasma GH concentration ranged from 90-120 ng/mL after 15 µg/kg ghrelin was administered i.v. Both HM04 and R011 inhibited ghrelin-induced increase of GH by 35% and 78%, respectively. The mean plasma growth hormone concentration observed for each of the four groups at time 0 and 15 minutes following ghrelin injection are shown in FIG. 22 (***p<0.01 vs vehicle; ###p<0.05 compared with ghrelin alone.

Example 13

Effect of HM04 Fumarate Salt in a Prader-Willi Mouse Model

The effect of HM04 fumarate salt on food intake behavior and glucose tolerance was investigated in the Snord116+/− (Het) mouse genetic model of Prader-Willi syndrome (Het mouse) compared to wild-type (WT) littermates. Since D2R agonists suppress food intake, the FDA approved D2R agonist cabergoline was used as an experimental control. Phenotypic characteristics of this PWS mouse model include hyperphagia, postnatal growth retardation, high ghrelin, and low growth hormone. Ding F., et al. SnoRNA Snord116 (Pwcr1/MBII-85) deletion causes growth deficiency and hyperphagia in mice. *PloS one*. 2008; 3(3):e1709. These PWS mice eat more frequently than WT littermates, particularly during the light cycle and are more motivated to work for food (more level presses) (data not shown).

Figure 25A:
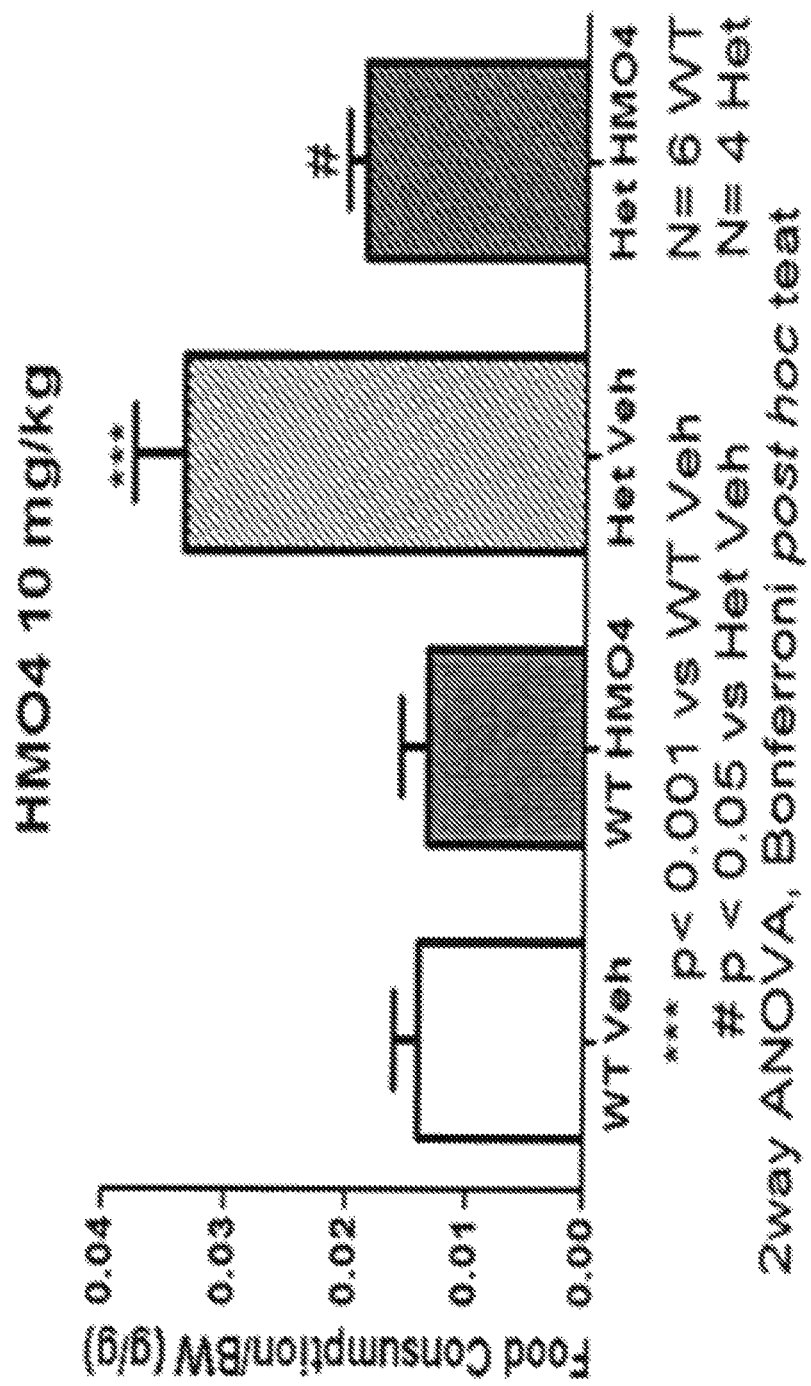
FIG. 25A shows food intake in 12-month-old Snord116+/− (Het) mice and 12-month-old wild-type (WT) littermates measured 1 hour after a single intraperitoneal administration of 1) vehicle (Het n=4; WT n=6) or 2) 10 mg/kg HM04 fumarate salt (based on the weight of the free base) (Het n=4; WT n=6). The mice were fasted for 16 hours prior to injection and given free access to food after injection.
Figure 25B:
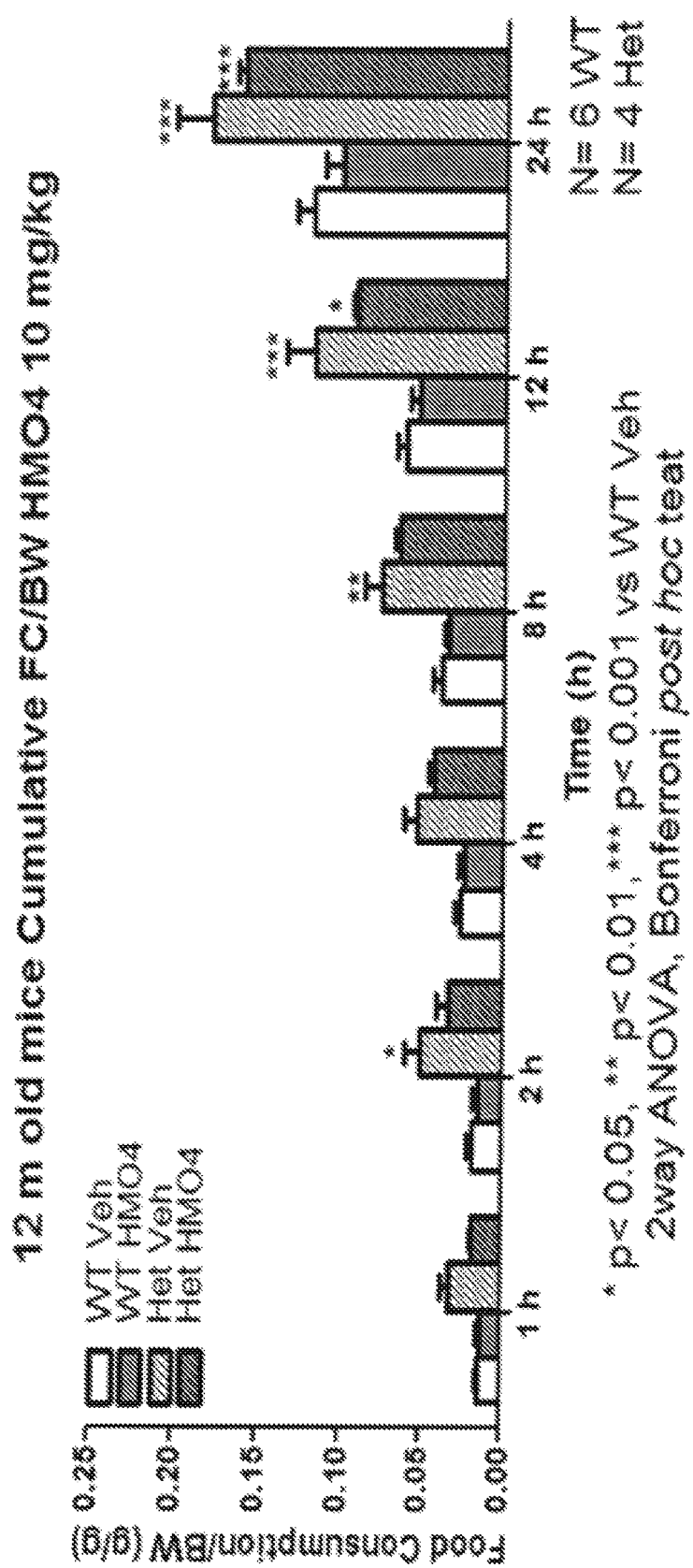
FIG. 25B shows food intake in 12-month-old Snord116+/− (Het) mice and 12-month-old wild-type (WT) littermates measured 1 hour, 2 hours, 4 hours, 8 hours, 12 hours, and 24 hours after a single intraperitoneal administration of 1) vehicle (Het n=4; WT n=6) or 2) 10 mg/kg HM04 fumarate salt (based on the weight of the free base) (Het n=4; WT n=6). The mice were fasted for 16 hours prior to injection and given free access to food after injection.
Figure 26:
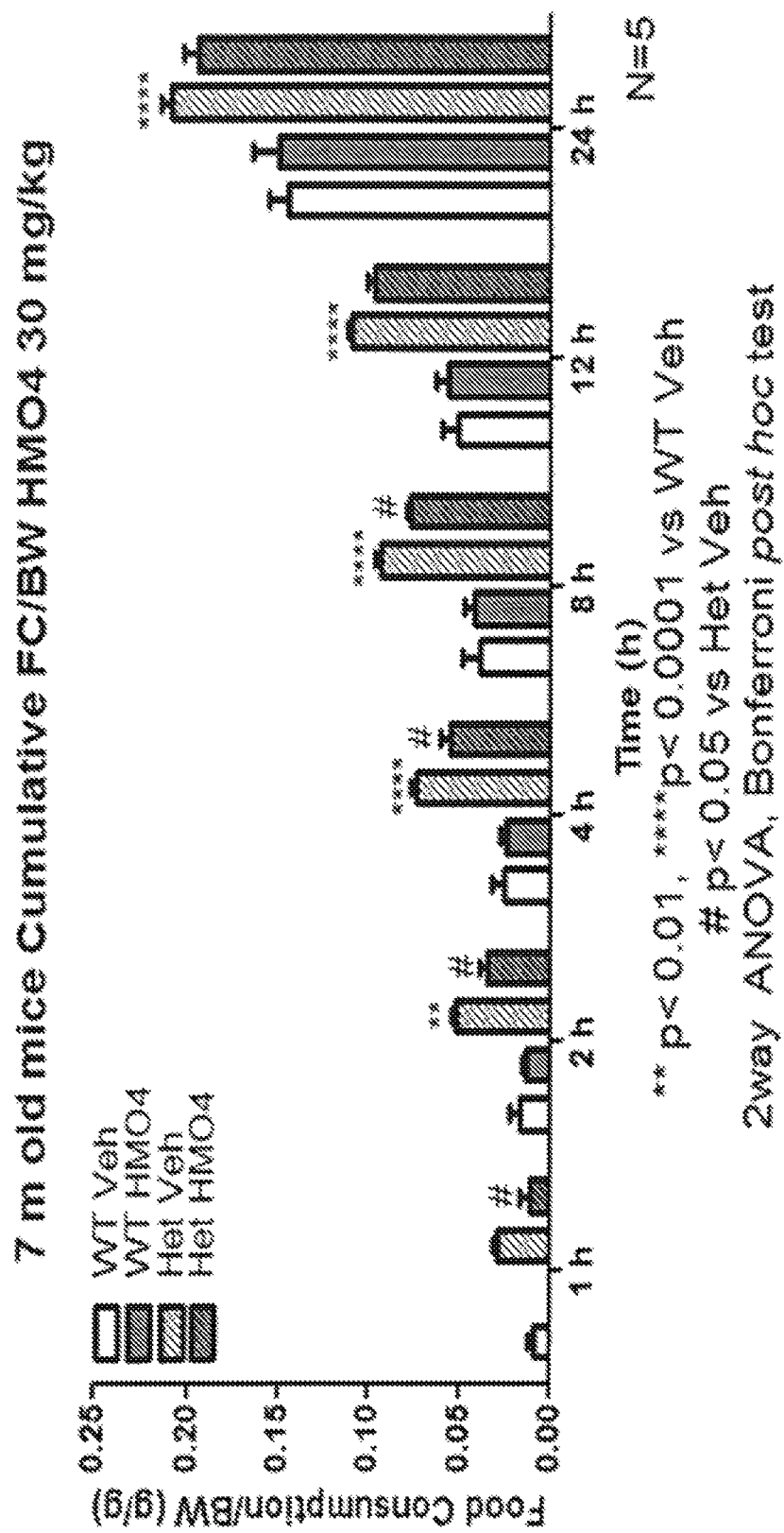
FIG. 26 shows food intake in 7-month-old Snord116+/− (Het) mice and 7-month-old wild-type (WT) littermates measured 1 hour, 2 hours, 4 hours, 8 hours, 12 hours, and 24 hours after a single intraperitoneal administration of 1) vehicle (n=5) 30 mg/kg HM04 fumarate salt (based on the weight of the free base) (n=5). The mice were fasted for 16 hours prior to injection and given free access to food after injection.
Figure 27A:
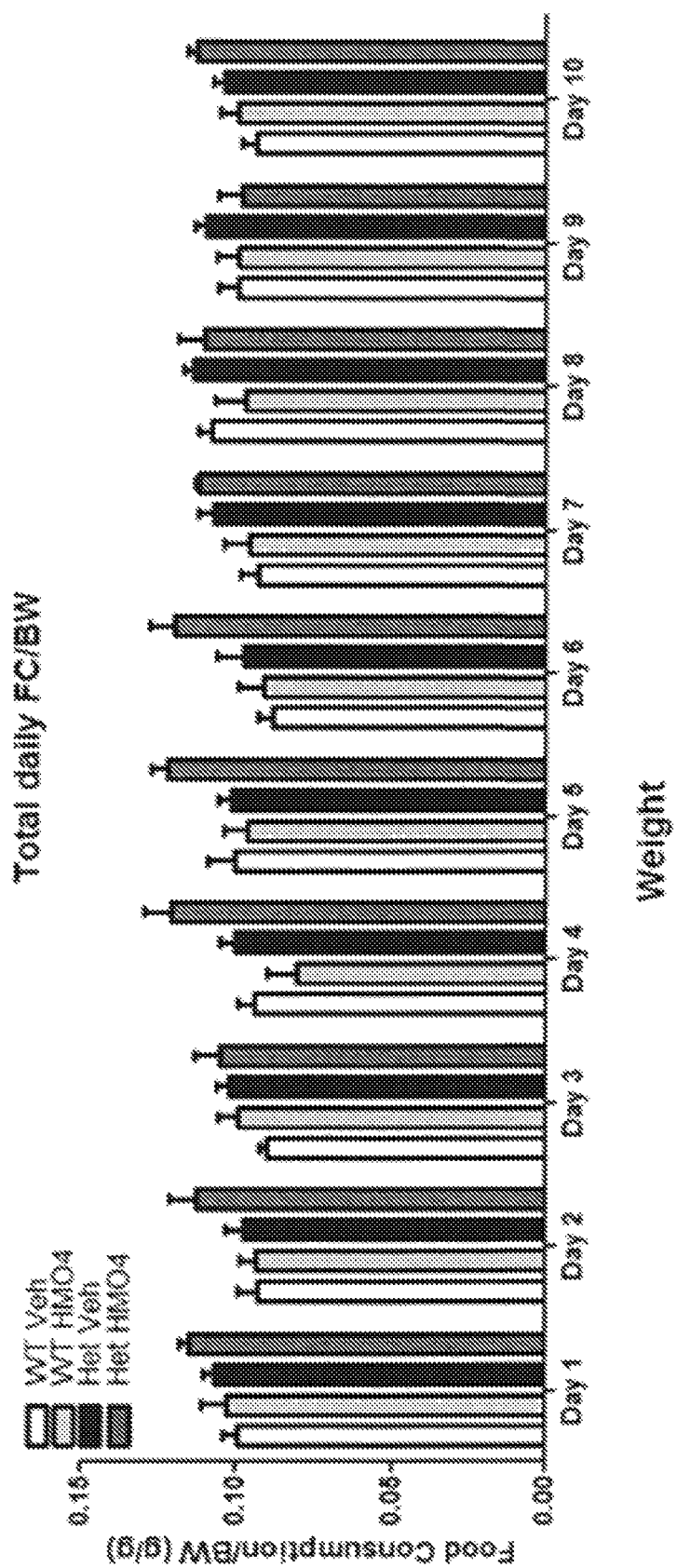
FIG. 27A shows food intake and FIG. 27B shows weight of 6-month-old Snord116+/− (Het) mice and 6-month-old wild-type (WT) littermates measured daily after 10 consecutive days of intraperitoneal administration at 07.00 hours of 1) vehicle (n=10) or 2) 10 mg/kg HM04 fumarate salt (based on the weight of the free base) (n=10).
Figure 27B:
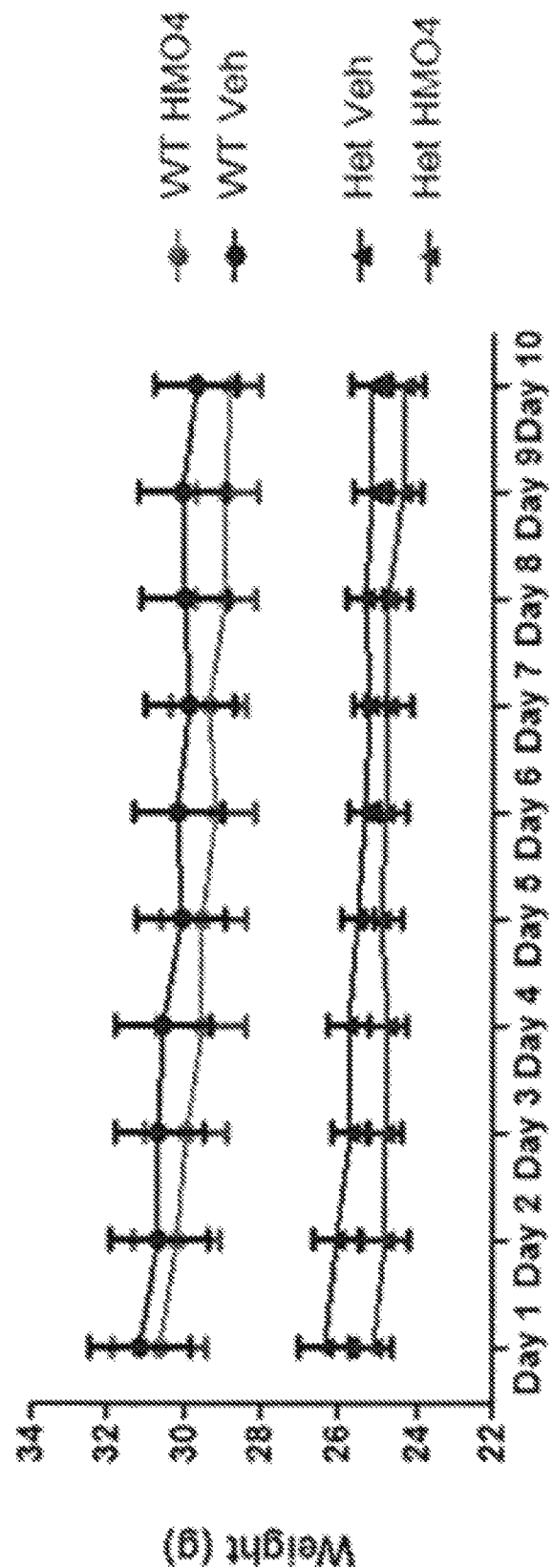

HM04 dosed at 10 mg/kg intraperitoneal (i.p.) did not reduce food intake in 3-, 7-, or 12-month-old WT mice (see FIGS. 25-27). HM04 (10 mg/kg, i.p.) suppressed food intake at 12 and 24 hours post-dosing in 3-month-old Het mice (FIG. 26). HM04 (10 mg/kg, i.p.) suppressed food intake at 1 hour post-dosing in 12-month-old Het mice (FIG. 25A), but that level of suppression was not maintained (FIG. 25B). HM04 dosed at 30 mg/kg i.p. inhibited food intake for up to 8 hours post-dosing in 7-month-old Het mice, but not in WT mice (FIG. 26). When HM04 was administered at 30 mg/kg orally to 8-month-old Het mice at 07.00 hours daily for five days, food intake was reduced up to 2 days without affecting body weight (FIGS. 30A and 30B). When HM04 was administered at 30 mg/kg orally to 8-month-old Het mice at 18.00 hours during the dark cycle, food intake was lower during the subsequent light cycle on days 2, 3, 4, and 5 and reached significance on day 5 (FIG. 31A).

In contrast to the effect of food intake, HM04 did not show an improvement in glucose tolerance in the Het mice, whereas an effect was observed in WT mice. These results suggest that HM04 may improve hyperphagia associated with PWS, although factors related to age, circadian rhythms, energy status, and metabolism may affect the pharmacological response.

Acute administration: Mice (3-, 7-, and 12-month-old) were fasted for 16 hours and then administered a single intraperitoneal injection of vehicle or vehicle containing HM04, cabergoline, or HM04 and cabergoline according to Table 8, below.

TABLE 8

| Strain | Age (months) | Number of animals | Compound and dose (mg/kg) |
| --- | --- | --- | --- |
| Het | 7 | 6 | HM04 (10) |
| Het | 7 | 6 | cabergoline (0.5) |
| Het | 7 | 6 | vehicle |
| Het | 7 | 6 | HM04 (10) + cabergoline (0.5) |
| WT | 7 | 6 | HM04 (10) |
| WT | 7 | 6 | cabergoline (0.5) |
| WT | 7 | 6 | vehicle |
| WT | 7 | 6 | HM04 (10) + cabergoline (0.5) |
| Het | 3 | 6 | HM04 (10) |
| Het | 3 | 6 | vehicle |
| WT | 3 | 6 | HM04 (10) |
| WT | 3 | 6 | vehicle |
| Het | 12 | 4 | HM04 (10) |
| Het | 12 | 4 | vehicle |
| WT | 12 | 6 | HM04 (10) |
| WT | 12 | 6 | vehicle |
| Het | 7 | 5 | HM04 (30) |
| Het | 7 | 5 | vehicle |
| WT | 7 | 5 | HM04 (30) |
| WT | 7 | 5 | vehicle |

HM04 was dissolved in water for injection and cabergoline was dissolved in DMSO to provide a 5% DMSO/water solution for injection. Mice were then given free access to food, and cumulative food intake was measured at 1, 2, 4, 8, 12, and 24 hours post-dosing. Since the Het mice are significantly smaller than their WT littermate controls, food intake was expressed as intake per g body weight. Data was analyzed for significance using 2-way ANOVA, Bonferroni post hoc test (Graphpad Prism, Prism 5.0, San Diego, Calif.).

Figure 23A:
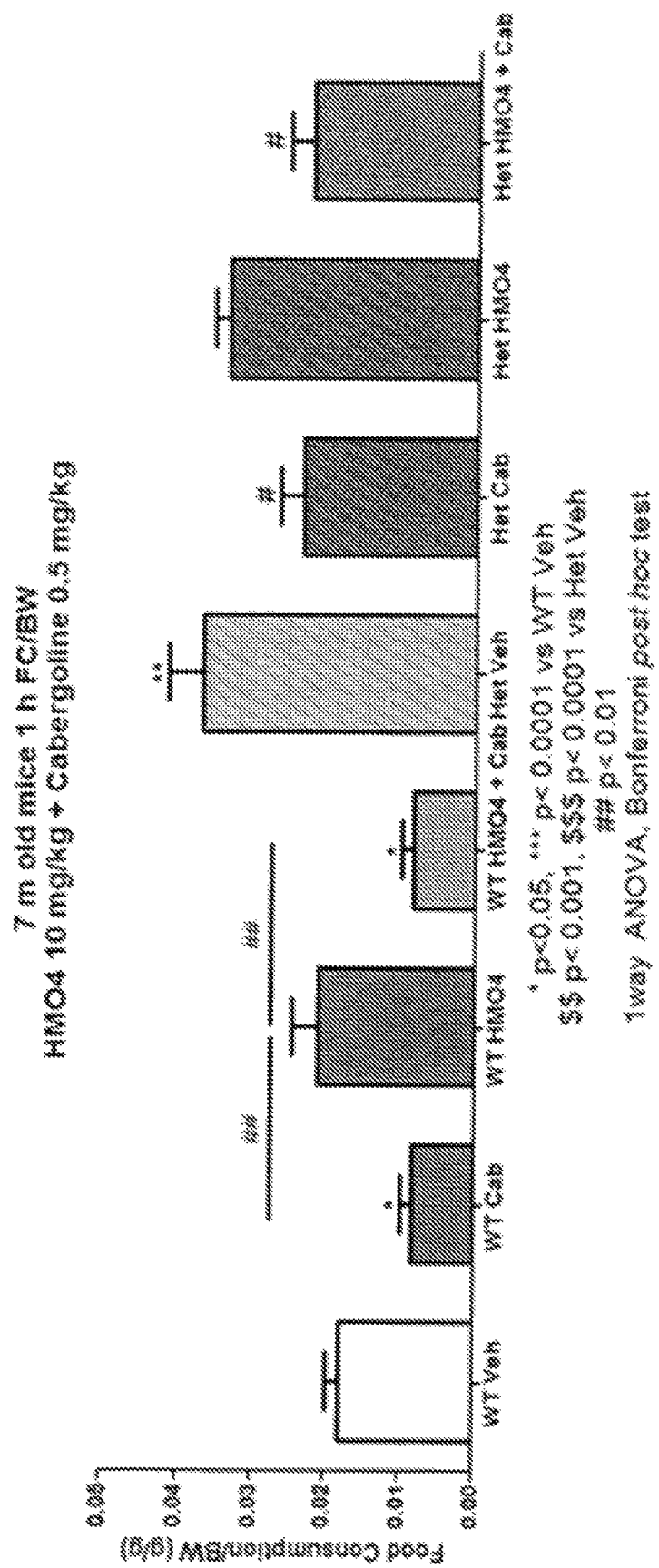
FIG. 23A shows food intake in 7-month-old Snord116+/− (Het) mice and 7-month-old wild-type (WT) littermates measured 1 hour after a single intraperitoneal administration of 1) vehicle (n=6); 2) 10 mg/kg HM04 fumarate salt (based on the weight of the free base) (n=6); 3) 0.5 mg/kg cabergoline (n=6); or 4) 10 mg/kg HM04 fumarate salt (based on the weight of the free base) plus 0.5 mg/kg cabergoline (n=6). The mice were fasted for 16 hours prior to injection and given free access to food after injection.
Figure 23B:
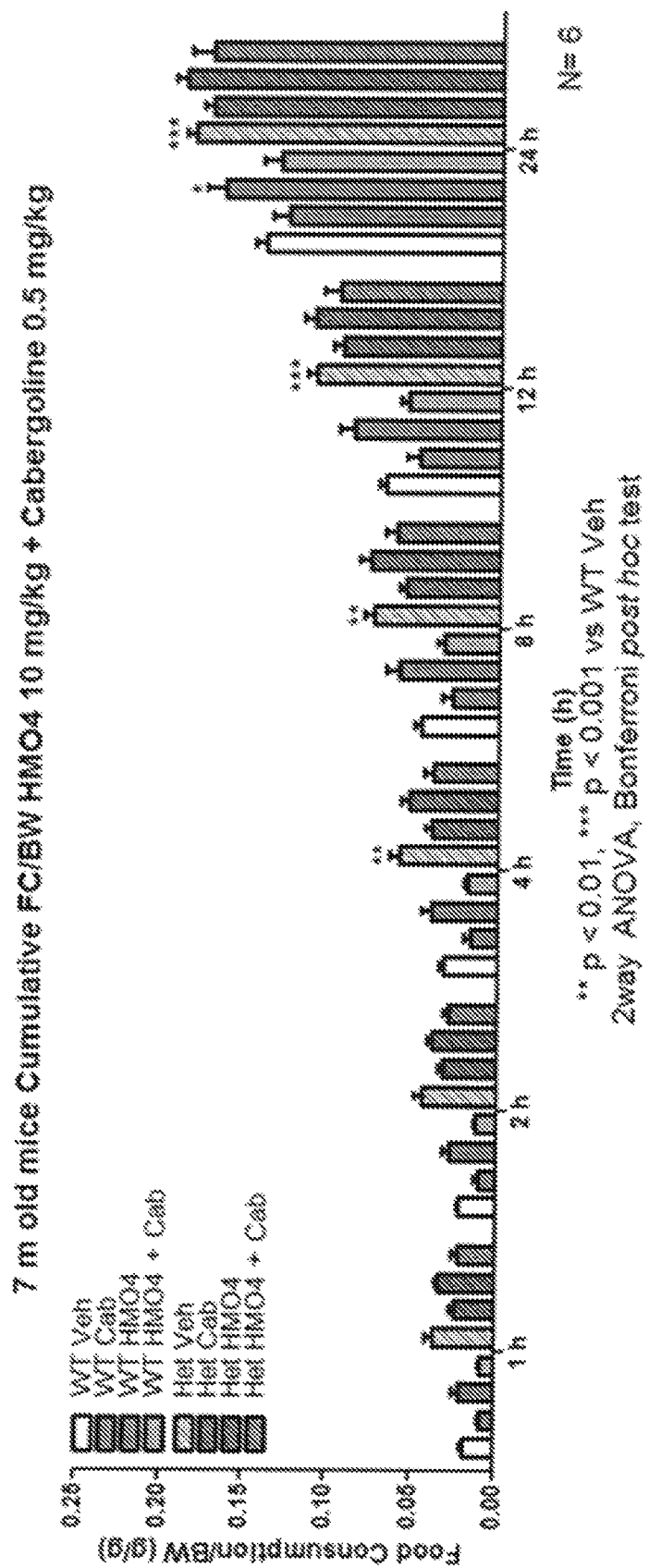
FIG. 23B shows food intake in 7-month-old Snord116+/− (Het) mice and 7-month-old wild-type (WT) littermates measured 1 hour, 2 hours, 4 hours, 8 hours, 12 hours, and 24 hours after a single intraperitoneal administration of 1) vehicle (n=6); 2) 10 mg/kg HM04 fumarate salt (based on the weight of the free base) (n=6); 3) 0.5 mg/kg cabergoline (n=6); or 4) 10 mg/kg HM04 fumarate salt (based on the weight of the free base) plus 0.5 mg/kg cabergoline (n=6). The mice were fasted for 16 hours prior to injection.

For the 7-month-old cohort, cumulative food intake was significantly elevated in vehicle-treated Het mice compared to vehicle-treated WT mice. Cabergoline inhibited food intake in both genotypes. By contrast, HM04 (10 mg/kg) did not inhibit food intake in either WT or Het mice, and failed to enhance suppressive effect of cabergoline on food consumption (FIGS. 23A and 23B).

Figure 24:
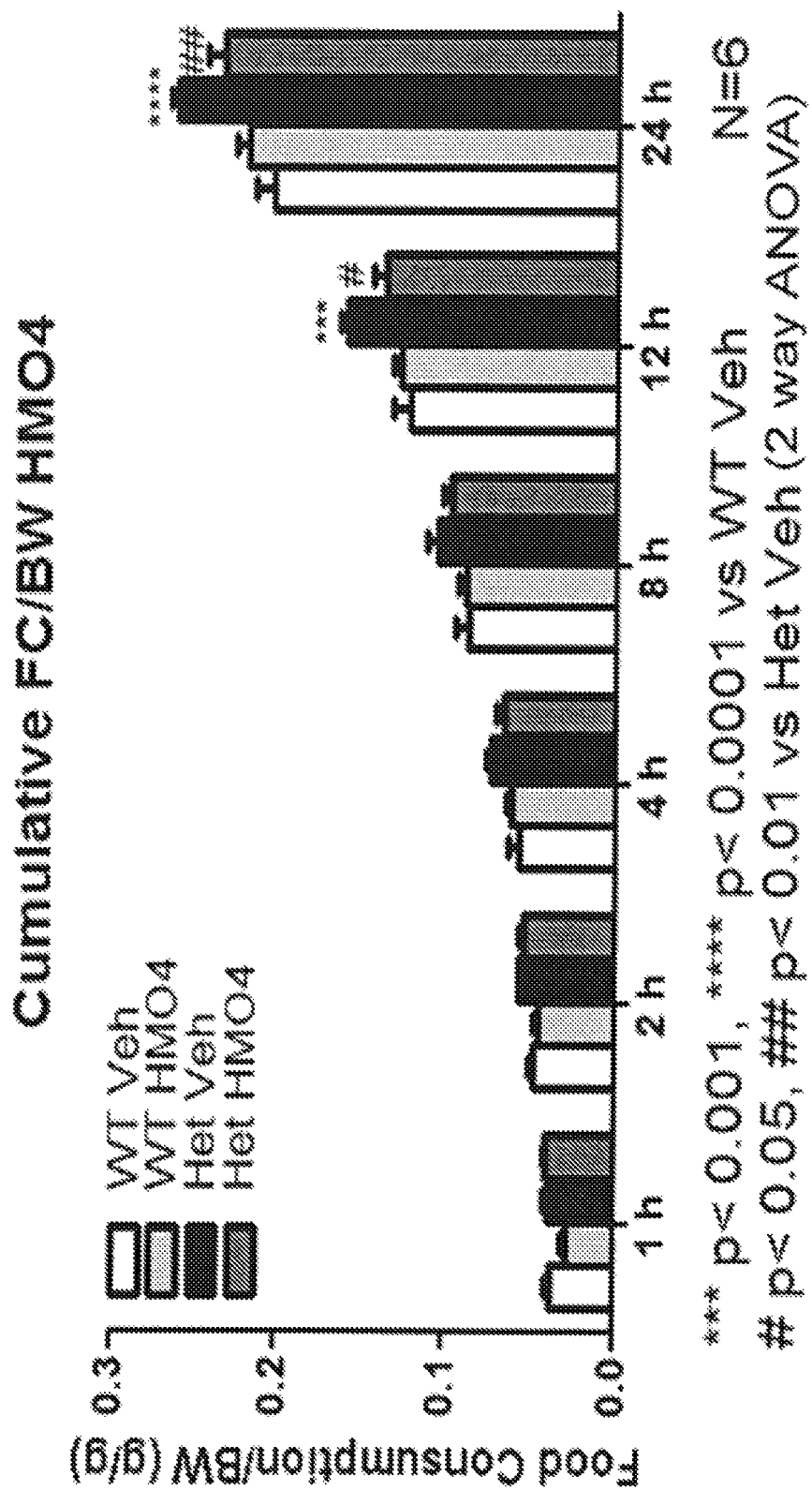
FIG. 24 shows food intake in 3-month-old Snord116+/− (Het) mice and 3-month-old wild-type (WT) littermates measured 1 hour, 2 hours, 4 hours, 8 hours, 12 hours, and 24 hours after a single intraperitoneal administration of 1) vehicle (n=6) or 2) 10 mg/kg HM04 fumarate salt (based on the weight of the free base) (n=6). The mice were fasted for 16 hours prior to injection and given free access to food after injection.

For the 3-month-old group, cumulative food intake was not significantly different in vehicle-treated mice for the first 8 hours. At 12 and 24 hours, Het mice had consumed more food than WT mice. Treatment with HM04 (10 mg/kg) significantly suppressed food intake at 12 and 24 hours post-dosing in Het mice (see FIG. 24). HM04 failed to inhibit food intake in WT mice.

In 12-month-old mice, food intake was significantly greater in vehicle-treated Het mice than in WT mice. HM04 (10 mg/kg) suppressed food intake in Het mice 1 hour after dosing (FIG. 25A); however, that level of inhibition was not maintained (FIG. 25B).

The group of 7-month-old Het and WT mice administered vehicle or HM04 at a higher dose of 30 mg/kg were also evaluated. HM04 (30 mg/kg) had no apparent effect on food intake in WT mice, but inhibited food intake for up to 8 hours in Het mice (FIG. 26).

Daily administration: To test if HM04 may be more effective if administered daily, 6-month-old mice were injected once daily at 07.00 hours for 10 days with vehicle, or vehicle containing HM04 (10 mg/kg ip), and 8-month-old mice were treated daily at 07.00 hours or 18.00 hours for 5 days by oral gavage with vehicle or vehicle containing HM04 at a higher dose of 30 mg/kg. A summary is provided in Table 9, below. Food intake and body weight were measured daily.

TABLE 9

| Strain | Age (months) | Number of animals | Hour of admin | Route of admin | Consecutive days of admin | Compound and dose (mg/kg) |
|---|---|---|---|---|---|---|
| Het | 6 | 10 | 07.00 | ip | 10 | HM04 (10) |
| Het | 6 | 10 | 07.00 | ip | 10 | vehicle |
| WT | 6 | 10 | 07.00 | ip | 10 | HM04 (10) |
| WT | 6 | 10 | 07.00 | ip | 10 | vehicle |
| Het | 8 | 5 | 07.00 | oral | 5 | HM04 (30) |
| Het | 8 | 5 | 07.00 | oral | 5 | vehicle |
| WT | 8 | 5 | 07.00 | oral | 5 | HM04 (30) |
| WT | 8 | 5 | 07.00 | oral | 5 | vehicle |
| Het | 8 | 5 | 18.00 | oral | 5 | HM04 (30) |
| Het | 8 | 5 | 18.00 | oral | 5 | vehicle |
| WT | 8 | 5 | 18.00 | oral | 5 | HM04 (30) |
| WT | 8 | 5 | 18.00 | oral | 5 | vehicle |

In the 6-month-old group, food consumption was not significantly different in vehicle-treated WT and Het mice. Daily treatment with HM04 (10 mg/kg i.p.) had no apparent effect on food intake (FIG. 27A) or body weight (FIG. 27B) in WT and Het mice.

Figure 28A:
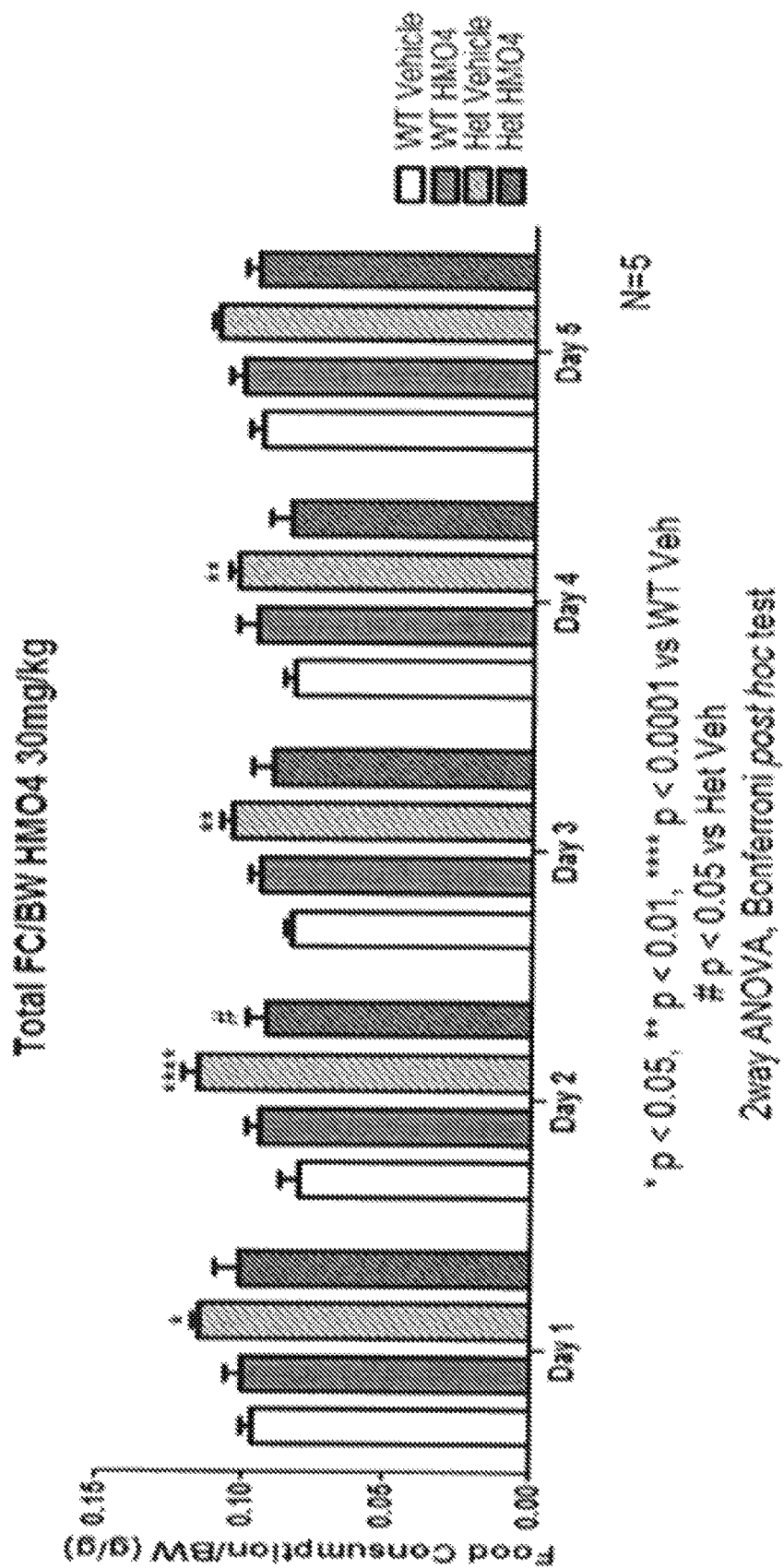
FIG. 28A shows food intake and FIG. 28B shows weight of 8-month-old Snord116+/− (Het) mice and 8-month-old wild-type (WT) littermates measured daily after 5 consecutive days of oral administration at 07.00 hours of 1) vehicle (n=5) or 2) 30 mg/kg HM04 fumarate salt (based on the weight of the free base) (n=5).
Figure 28B:
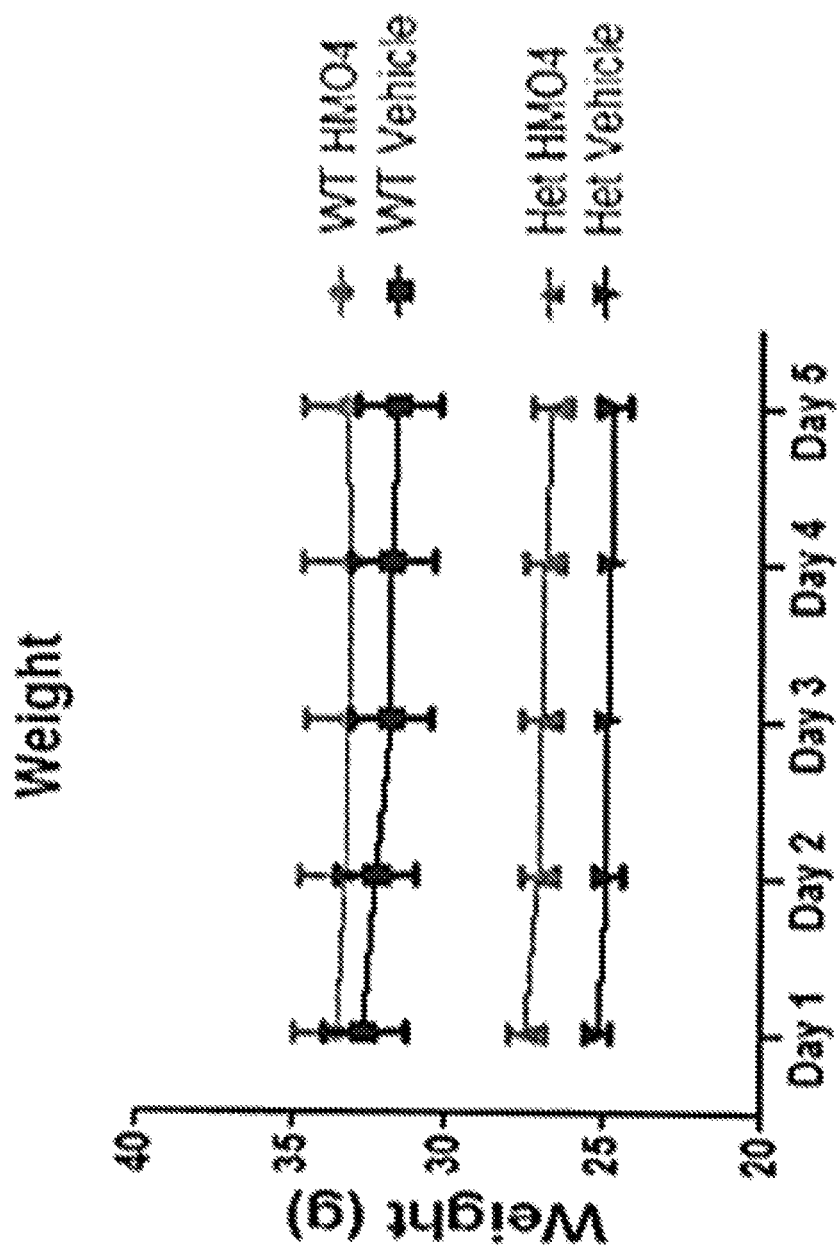

In the 8-month-old group treated at 07.00 hours during the light cycle, a significant decrease in food intake was observed by day 2, but not on subsequent days (FIG. 28A). Body weight was unaffected (FIG. 28B). No reduction in food intake or body weight was observed in HM04 WT mice (FIGS. 28A and 28B).

Figure 29A:
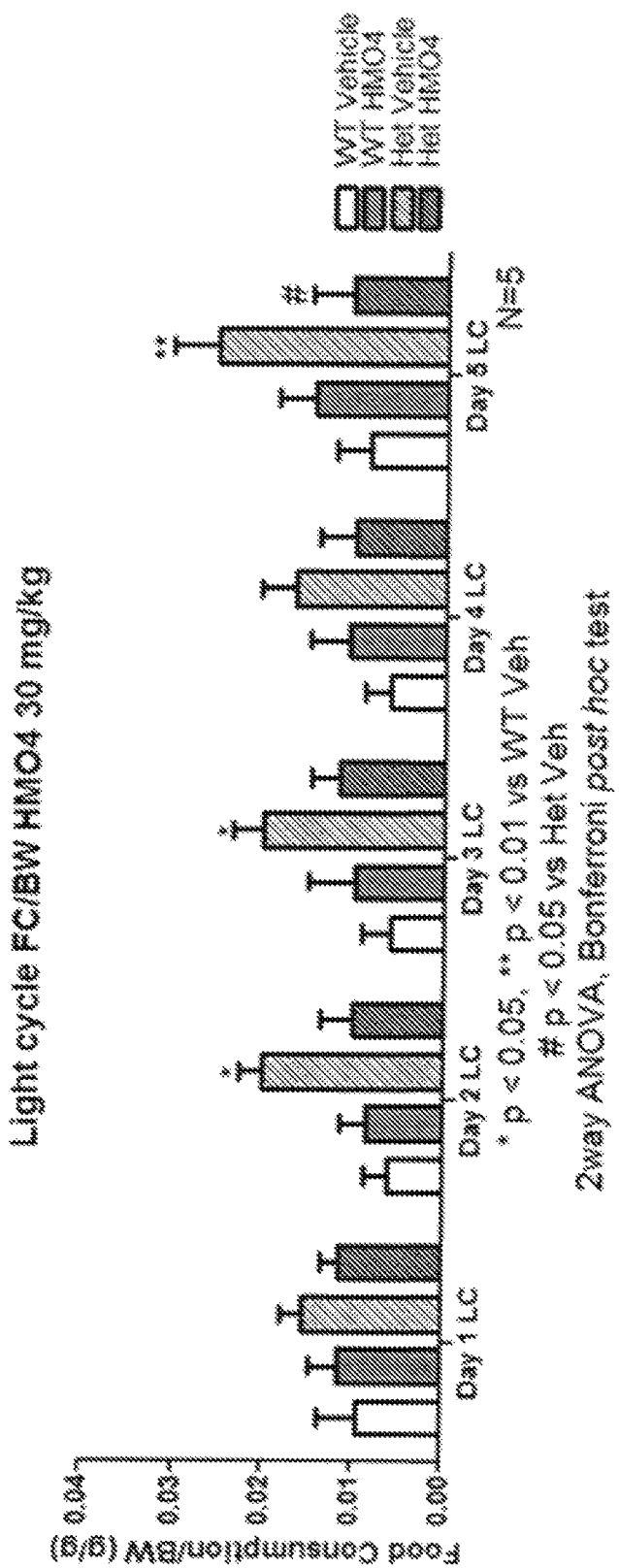
FIG. 29A shows food intake during the light cycle and FIG. 29B shows food intake during the dark cycle of 8-month-old Snord116+/− (Het) mice and 8-month-old wild-type (WT) littermates measured daily after 5 consecutive days of oral administration at 18.00 hours of 1) vehicle (n=5) or 2) 30 mg/kg HM04 fumarate salt (based on the weight of the free base) (n=5).
Figure 29B:
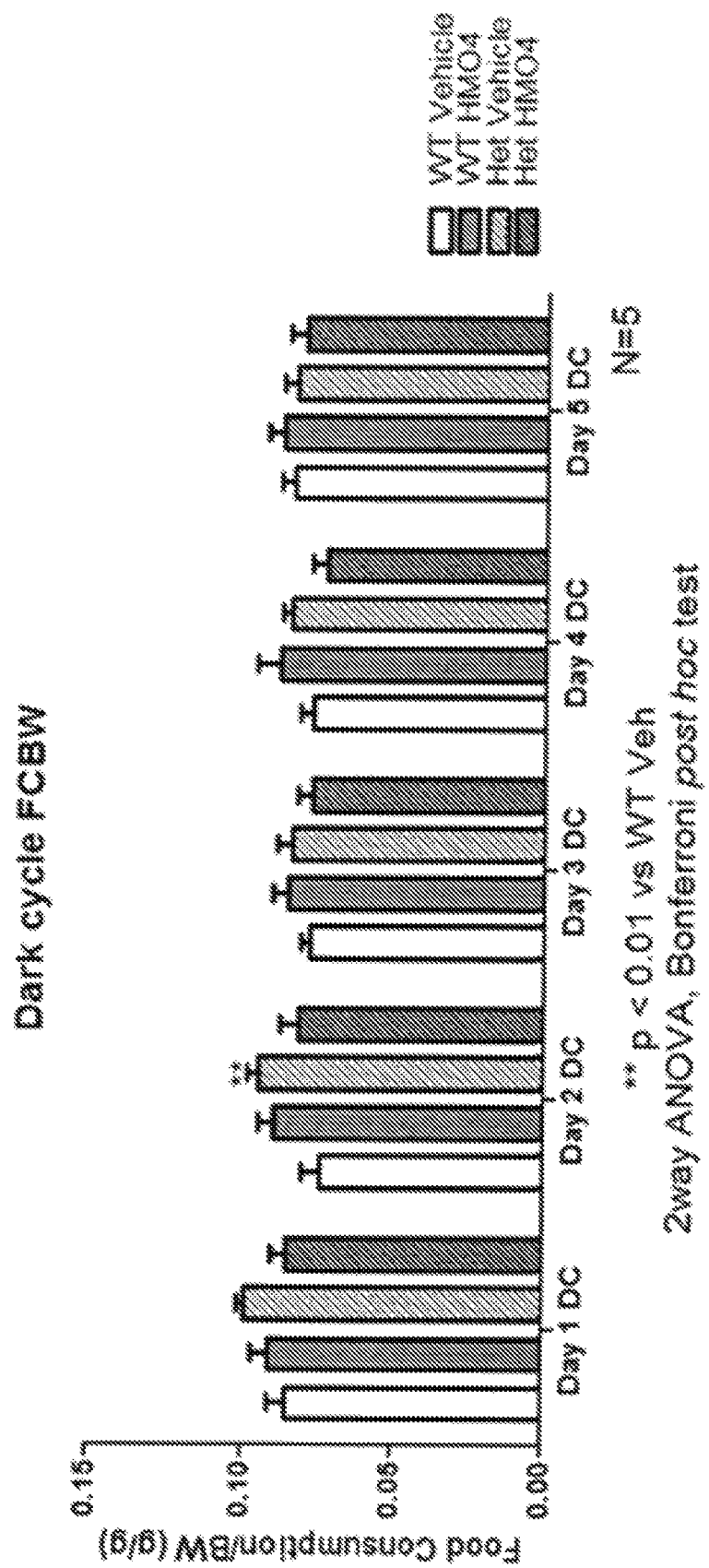

For the 8-month-old group treated at 18.00 hours during the dark cycle, food intake was measured during both the light and dark cycles. Despite treating mice with HM04 at the beginning of the dark cycle, suppression of food consumption was not observed during the dark cycle in either WT or Het mice (FIG. 29B). During the subsequent light cycle (06.00-18.00), food intake was lower in HM04-treated Het mice, but not WT mice on days 2, 3, 4, and 5 and reached significance on day 5 (FIG. 29A).

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A 1:1 (R)-3-(1-(2,3-dichloro-4-(pyrazin-2-yl)phenyl)-2,2,2-trifluoroethyl)-1-methyl-1-(1-methylpiperidin-4-yl)urea:fumarate salt, wherein the salt is at least 50%, at least 60%, at least 70%, at least 80%, at least 90%, at least 95%, at least 96%, at least 97%, at least 98%, at least 99%, or 100% in crystalline form, and wherein the salt comprises at least one crystalline form chosen from Form 1, Form 2, Form 3, and Form 4.

2. The salt of claim 1 comprising Form 1 having an XRPD pattern substantially similar to the XRPD pattern of FIG. 12 as determined by XRPD using Cu K alpha radiation.

3. The salt of claim 1 comprising Form 2 characterized by an XRPD pattern substantially similar to the XRPD pattern of FIG. 3 as determined by XRPD using Cu K alpha radiation.

4. The salt of claim 1, comprising Form 3 characterized by an XRPD pattern substantially similar to the XRPD pattern of FIG. 15 as determined by XRPD using Cu K alpha radiation.

5. The salt of claim 1, comprising Form 4 characterized by an XRPD pattern substantially similar to the XRPD pattern of FIG. 16 as determined by XRPD using Cu K alpha radiation.

6. The salt of claim 1, comprising Form 1 characterized by an XRPD pattern, using Cu K alpha radiation, comprising peaks at 7.8±0.2, 9.5±0.2, 14.3±0.2, 16.7±0.2, 17.2±0.2, 18.5±0.2, 18.8±0.2, 19.3±0.2, 20.0±0.2, 20.7±0.2, 22.4±0.2, 23.2±0.2, 25.6±0.2, 27.2±0.2, 31.7±0.2, and 32.4±0.2 degrees 2 theta.

7. The salt of claim 1, comprising Form 3 characterized by an XRPD pattern, using Cu K alpha radiation, comprising peaks at 7.2±0.2, 9.4±0.2, 9.7±0.2, 10.8±0.2, 14.3±0.2, 15.1±0.2, 16.2±0.2, 17.9±0.2, 18.7±0.2, 18.9±0.2, 19.6±0.2, 21.5±0.2, 22.7±0.2, 23.7±0.2, 24.3±0.2, 25.1±0.2, 27.4±0.2, 28.7±0.2, and 34.9±0.2 degrees 2 theta.

8. The salt of claim 1 comprising Form 4 characterized by an XRPD pattern, using Cu K alpha radiation, comprising peaks at 12.2±0.2, 13.2±0.2, 15.0±0.2, 15.4±0.2, 17.6±0.2, 18.1±0.2, 19.5±0.2, 20.2±0.2, 20.9±0.2, 21.4±0.2, 23.0±0.2, 23.4±0.2, 24.4±0.2, 24.8±0.2, 25.9±0.2, 27.9±0.2, 28.9±0.2, 29.6±0.2, 30.7±0.2 degrees 2 theta.

9. Crystalline (R)-3-(1-(2,3-dichloro-4-(pyrazin-2-yl)phenyl)-2,2,2-trifluoroethyl)-1-methyl-1-(1-methylpiperidin-4-yl)urea having an XRPD pattern substantially similar to the XRPD pattern of FIG. 1A as determined by XRPD using Cu K alpha radiation.

10. A drug product comprising the salt of claim 1.

11. A composition comprising the salt of claim 1.

12. A method of preparing the salt of claim 1 comprising combining (R)-3-(1-(2,3-dichloro-4-(pyrazin-2-yl)phenyl)-2,2,2-trifluoroethyl)-1-methyl-1-(1-methylpiperidin-4-yl) urea with fumaric acid.

13. The method of claim 12, wherein the (R)-3-(1-(2,3-dichloro-4-(pyrazin-2-yl)phenyl)-2,2,2-trifluoroethyl)-1-methyl-1-(1-methylpiperidin-4-yl)urea is in solid form when combined with fumaric acid.

14. The method of claim 12, wherein the (R)-3-(1-(2,3-dichloro-4-(pyrazin-2-yl)phenyl)-2,2,2-trifluoroethyl)-1-methyl-1-(1-methylpiperidin-4-yl)urea is in solution when combined with fumaric acid.

15. The method of claim 12, wherein the (R)-3-(1-(2,3-dichloro-4-(pyrazin-2-yl)phenyl)-2,2,2-trifluoroethyl)-1-methyl-1-(1-methylpiperidin-4-yl)urea is subjected to acid/base extraction prior to being combined with fumaric acid.

16. The method of claim 12, wherein the (R)-3-(1-(2,3-dichloro-4-(pyrazin-2-yl)phenyl)-2,2,2-trifluoroethyl)-1-methyl-1-(1-methylpiperidin-4-yl)urea is not subjected to an acid/base extraction prior to being combined with fumaric acid.

17. A method of reducing ghrelin signaling activity in a cell comprising exposing the cell to the salt of claim 1.

18. The method of claim 17, wherein the cell is exposed to the salt in vitro.

19. The method of claim 17, wherein the ghrelin signaling activity is measured by level of intracellular calcium as detected by fluorescence imaging plate reader (FLIPR) assay.

20. A method of reducing ghrelin signaling activity in a subject comprising administering to the subject the salt of claim 1.

21. A method of treating a subject having a condition or disorder associated with an increase in ghrelin level, comprising administering to the subject a therapeutically effective amount of the salt of claim 1, wherein the condition or disorder is chosen from food abuse, alcohol addiction, and Prader-Willi syndrome.

22. The method of claim 21, wherein the condition or disorder is chosen from binge eating, obesity, post-dieting body weight rebound, and hyperphagia.

* * * * *